US009080159B2

(12) United States Patent
Briles et al.

(10) Patent No.: US 9,080,159 B2
(45) Date of Patent: Jul. 14, 2015

(54) DETOXIFIED PNEUMOCOCCAL NEURAMINIDASE AND USES THEREOF

(71) Applicant: The UAB Research Foundation, Birmingham, AL (US)

(72) Inventors: David E. Briles, Birmingham, AL (US); Susan K. Hollingshead, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/670,839

(22) Filed: Nov. 7, 2012

(65) Prior Publication Data

US 2014/0004138 A1    Jan. 2, 2014

Related U.S. Application Data

(63) Continuation of application No. 12/601,233, filed as application No. PCT/US2007/069571 on May 23, 2007, now Pat. No. 8,329,195.

(51) Int. Cl.
| | |
|---|---|
| *A61K 39/09* | (2006.01) |
| *C07K 14/195* | (2006.01) |
| *C07K 14/315* | (2006.01) |
| *C12N 9/24* | (2006.01) |

(52) U.S. Cl.
CPC ............ *C12N 9/2402* (2013.01); *A61K 39/092* (2013.01); *C12Y 302/01018* (2013.01)

(58) Field of Classification Search
CPC ............... A61K 39/092; A61K 38/00; A61K 2039/543; A61K 2039/55544; A61K 2039/505; A61K 2039/507; A61K 38/164; A61K 39/09; C12N 9/2402; C07K 14/3156; C07K 16/1275; C07K 16/40; C07K 2319/21
See application file for complete search history.

(56) References Cited

U.S. PATENT DOCUMENTS

| | | | |
|---|---|---|---|
| 5,792,457 | A | 8/1998 | Tuomanen et al. |
| 6,027,734 | A | 2/2000 | Briles et al. |
| 6,500,613 | B1 | 12/2002 | Briles et al. |
| 6,514,503 | B1 | 2/2003 | Gizurarson et al. |
| 6,573,082 | B1 | 6/2003 | Choi et al. |
| 6,635,246 | B1 | 10/2003 | Barrett et al. |
| 6,699,703 | B1 | 3/2004 | Doucette-Stamm et al. |
| 7,202,056 | B2 | 4/2007 | Lee et al. |
| 7,635,487 | B2 | 12/2009 | Meinke et al. |
| 8,329,195 | B2 | 12/2012 | Briles et al. |
| 2006/0263846 | A1 | 11/2006 | Meinke et al. |

FOREIGN PATENT DOCUMENTS

| | | |
|---|---|---|
| WO | WO 00/06737 | 2/2000 |
| WO | WO 02/077021 | 10/2002 |
| WO | WO 02/083855 | 10/2002 |
| WO | 2004092209 | 10/2004 |
| WO | WO 2005/046721 | 5/2005 |

OTHER PUBLICATIONS

Alonsodevalasco et al., "*Streptococcus pneumoniae*: virulence factors, pathogenesis, and vaccines", Microbiological Reviews, vol. 59, No. 4, Dec. 1995, pp. 591-603.
Briles et al., "Mouse antibody to phosphocholine can protect mice from infection with mouse-virulent human isolates of *Streptococcus pneumoniae*", Infection and Immunity, vol. 60, No. 5, May 1992, pp. 1957-1962.
Broun et al., "Catalytic plasticity of fatty acid modification enzymes underlying chemical diversity of plant lipids.", Science, vol. 282, 1998, pp. 1315-1317.
Communication pursuant to Article 94(3) EPC for European Patent Application No. 07797691.8 mailed Jul. 22, 2014.
Devos et al., "Practical limits of function prediction", Proteins: Structure, Function, and Genetics, vol. 41, 2000, pp. 98-107.
Korean Patent Application No. 1020067009031, English Translation of Office Action, issued Feb. 29, 2012, 2 pages.
International Patent Application No. PCT/US2007/069571, International Search Report & Written Opinion, issued Jan. 24, 2008, 9 pages.
Seffernick et al., "Melamine deaminase and Atrazine chlorohydrolase: 98 percent identical but functionally different", J. Bacteriol., vol. 183, No. 8, 2001, pp. 2405-2410.
Trolle et al., "Intranasal immunization with protein-linked phosphorylcholine protects mice against a lethal intranasal challenge with *Streptococcus pneumoniae*", Vaccine, vol. 18, No. 26, Jul. 1, 2000, pp. 2991-2998.
Whisstock et al., "Prediction of Protein Function from Protein Sequence and Structure", Quarterly Review of Biophysics, vol. 36, No. 3, Aug. 2003, pp. 307-340.
Witkowski et al., "Conversion of b-ketoacyl synthase to a Malonyl Decarboxylase by replacement of the active cysteine with glutamine.", Biochemistry, vol. 38, 1999, pp. 11643-11650.
Wu et al., "Establishment of *Streptococcus pneumoniae* nasopharyngeal colonization model in adult mice", Microbial Pathogenesis, vol. 23, No. 3, 1997, pp. 127-137.
Yesilkaya et al., "Identification of amino acids essential for catalytic activity of pneumococcal neuraminidase A", Research in Microbiology, vol. 157, No. 6, 2006, pp. 569-574.

(Continued)

*Primary Examiner* — Padma V Baskar
(74) *Attorney, Agent, or Firm* — Kilpatrick Townsend & Stockton LLP

(57) ABSTRACT

Provided herein are compositions designed to reduce or prevent bacterial infections (for example pneuomococcal infections), nasal carriage, nasal colonization, and central nervous system invasion. Provided herein is a composition comprising a polypeptide comprising the amino acid sequence of SEQ ID NO:19 or a variant thereof that can elicit an anti-neuraminidase immune response. Further provided are methods of making and using the compositions disclosed herein. Specifically provided are methods of generating antibodies in a subject comprising administering to the subject an agent or composition taught herein. Also provided are methods of reducing or preventing nasal carriage or pneumococcal infection in a subject comprising administering to the subject a composition taught herein.

1 Claim, 15 Drawing Sheets

(56) References Cited

OTHER PUBLICATIONS

Yother et al., "Protection of Mice from Infection with *Streptococcus pneumoniae* by Anti-Phosphocholine Antibody", Infection and Immunity, vol. 36, No. 1, Apr. 1982, pp. 184-188.
Yother et al., "Transformation of encapsulated *Streptococcus pneumoniae*", Journal of Bacteriology, vol. 168, 1986, pp. 1463-1465.
Yother et al., "Truncated forms of PspA that are secreted from *Streptococcus pneumoniae* and their use in functional studies and cloning of the pspA gene", Journal of Bacteriology, vol. 174, No. 2, 1992, pp. 610-618.
Amsbaugh et al., "Genetic Control of the Antibody Response to Type III Pneumococcal Polysaccharide in Mice" *J. Exp. Med.* 136:931-949 (1972).
Avery et al., "Studies on the Chemical Nature of the Substance Inducing Transformation of Pneumococcal Types" *J. Exp. Med.* 149:297-326 (1979).
Balachandran et al., "Role of Pneumococcal Surface Protein C in Nashopharyngeal Carriage and Pneumonia and Its Ability to Elicit Protection against Carriage of *Streptococcus pneumoniae*" *Infection and Immunity* 70:2526-2534 (2002).
Berry et al., "Cloning and expression of the pneumococcal neuraminidase gene in *Escherichia coli*" *Gene* 71:299-305 (1988).
Berry et al., "Cloning and Characterization of nanB, a Second *Streptococcus pneumoniae* Neuraminidase Gene, and Purification of the NanB Enzyme from Recombinant *Escherichia coli*" *Journal of Bacteriology* 178(16):4854-4860 (1996).
Belly et al., "Additive Attenuation of Virulence of *Streptococcus pneumoniae* by Mutation of the Genes Encoding Pneumolysin and Other Putative Pneumococcal Virulence Proteins" *Infection and Immunity* 68:133-140 (2000).
Black et al., "Efficacy, safety and immunogenicity of heptavalent pneumococcal conjugate vaccine in children. Northern California Kaiser Permanente Vaccine Study Center Group" *Pediatr. Infect. Dis. J.* 19:187-195 (2000).
Briles et al., "Mouse Igg3 antibodies are highly protective against infection with *Streptococcus pneumoniae*" *Nature* 294(5836):88-90 (1981).
Briles et al., "Antiphosphocholone Antibodies Found in Normal Mouse Serum are Protective Against Intravenous Infection with Type 3 *Streptococcus pneumoniae*" *J. Exp. Med.* 153:694-705 (1981).
Briles et al., "The effects of idiotype on the ability of IgG1 anti-phosphorylcholine antibodies to protect mice from fatal infection with *Streptococcus pneumoniae*" *Eur. J. Immunol.* 14:1027-1030 (1984).
Briles et al., "The effects of subclass on the ability of anti-phosphocholine antibodies to protect mice from fatal infection with *Streptococcus pneumoniae*" *J. Mol. Cell. Immunol.* 1:305-309 (1984).
Briles et al., "Genetic control of the susceptibility to pneumococcal infection." *Curr. Top. Microbiol. Immunol.* 124:103-120 (1986).
Briles et al., "Antipneumococcal Effects of C-Reactive Protein and Monoclonal Antibodies to Penumococcal Cell Wall and Capsular Antigens" *Infection and Immunity* 57(5):1457-1464 (1989).
Briles et al., "Strong Association between Capsular Type and Virulence for mice among Human Isolates of *Streptococcus pneumoniae*" *Infection and Immunity* 60:111-116 (1992).
Briles et al., "Immunizations with Pneumococcal Surface Protein A and Pneumolysin are Protective against Pneumonia in a Murine Model of Pulmonary Infection with *Streptococcus pneumoniae*" *J. Infect. Dis.* 188:339-348 (2003).
Briles et al., "Nasal Colonization with *Streptococcus pneumoniae* Includes Subpopulations of Surface and Invasive Pneumococci" *Infection and Immunity* 73(10):6945-6951 (2005).
Brooks-Walter et al., "The pspC gene of *Streptococcus pneumoniae* encodes a polymorphic protein, PspC, which elicits cross-reactive antibodies to PspA and provides immunity to pneumococcal bacteremia" *Infection and Immunity* 67:6533-6542 (1999).

Camara et al., "A neuraminidase from *Streptococcus pneumoniae* has the features of a surface protein" *Infection and Immunity* 62(9):3688-3695 (1994).
Crennell et al., "Crystal structure of a bacterial sialidase (from *Salmonella typhimurium* LT2) shows the same fold as an influenza virus neuraminidase" *PNAS* 90(21):9852-9856 (1993).
Fischer et al., Teichoic acid and lipoteichoic acid of *Streptococcus pneumoniae* possess identical chain structures. A reinvestigation of teichoid acid (C polysaccharide). *Eur. J. Biochem.* 215(3):851-7 (1993).
Gray et al., "Epidemiologic studies of *Streptococcus pneumoniae* includes subpopulations of surface and invasive pneumococci" *J. Infect. Dis.* 142:923-33 (1980).
Hoskins et al., "Genome of the bacterium *Streptococcus pneumoniae* strain R6" *Journal of Bacteriology* 183(19):5709-5717 (2001).
Jedrzejas, "Pneumococcal virulence factors: structure and function" *Microbiol. Mol. Biol. Rev.* 65(2):187-207 (2001).
Kelly et al., "Neuraminidase activities of clinical isolates of *Diplococcus pneumoniae*" *J. Bacteriol.* 94:272-273 (1967).
King et al., "Phase variable desialylation of host proteins that bind to *Streptococcus pneumoniae* in vivo and protect the airway" *Mol. Microbiol.* 54:159-171 (2004).
King et al., "NanA, a neuraminidase from *Streptococcus pneumoniae* shows high levels of sequence diversity at least in part through recombination with *Streptococcus oralis*" *J. Bacteriol.* 187:5376-5386 (2005).
LaMarco et al., "Experimental alteration of *Chinchilla* middle ear mucosae by bacterial neuraminidase" *Ann. Otol. Rhinol. Laryngol.* 95:304-308 (1986).
Lock et al., "Purification and immunological characterization of neuraminidase produced by *Streptococcus pneumoniae*" *Microb. Pathog.* 4:33-43 (1988).
Lock et al., "Comparative efficacy of pneumococcal neuraminidase and pneumolysin as immunogens protective against *Streptococcus pneumoniae*" *Microb. Pathog.* 5(6):461-467 (1988).
Long et al., "Immunization with native or recombinant *Streptococcus pneumoniae* neuraminidase affords protection in the *Chinchilla* otitis media model" *Infection and Immunity* 72:4309-4313 (2004).
Madhi and Klugman, "A role for *Streptococcus pneumoniae* in virus-associated pneumonia" *Nat. Med.* 10:811-813 (2004).
Magee and Yother, "Requirement for capsule in colonization by *Streptococcus pneumoniae*" *Infection and Immunity* 69:3755-3761 (2001).
Martinot et al., "Haemolytic-Uraemic syndrome associated with *Streptococcus pneumoniae* meningitis" *European Journal of Pediatrics* 148(7):648-649 (1989).
Manco et al., "Pneumococcal neuraminidases A&B both have essential roles during infection of the respiratory trackt & sepsis" *Infection and Immunity* 74(7):4014-4020 (2006).
McCullers and Bartmess, "Role of neuraminidase in lethal synergism between influenza virus and *Streptococcus pneumoniae*" *J. Infect. Dis.* 187:1000-1009 (2003).
McDaniel et al., "A protective monoclonal antibody that reacts with a novel antigen of pneumococcal teichoic acid" *Microb. Pathog.* 3:249-260 (1987).
O'Toole et al., "Neuraminidase activity in bacterial meningitis" *J. Clin. Invest.* 50:979-985 (1971).
Paton et al., "Molecular analysis of the pathogenicity of *Streptococcus pneumoniae:* the role of pneumococcal proteins" *Annu. Rev. Microbiol.* 47:89-115 (1993).
Paton et al., "Molecular analysis of putative pneumococcal virulence proteins" *Microb. Drug Resist.* 3(1):1-10 (1997).
Potter et al., "BALB/c.CBA/N mice carrying the defective Btk[xid] gene are resistant to pristine-induced plasmacytomagenesis" *International Immunology* 11(7):1059-1064 (1999).
Scanlon et al., "Purification and properties of *Streptococcus pneumoniae* neuraminidase" *Enzyme* 41(3):143-150 (1989).
Shakhnovich et al., "Neuraminidase expressed by *Streptococcus pneumoniae* desialylates the lipopolysaccharide of *Neisseria meningitidis* and *Haemophilus influenzae:* a paradigm for interbacterial competition among pathogens of the human respiratory tract" *Infection and Immunity* 70:7161-7164 (2002).

(56) References Cited

OTHER PUBLICATIONS

Simell et al. "Serum antibodies to pneumococcal neuraminidase NanA in relation to pneumococcal carriage and acute otitis media" *Clinical and Vaccine Immunology* 13(10):1177-1179 (2006).

Tettelin et al., "Nasal lymphoid tissue (NALT) as a mucosal immune inductive site" *Science* 293:498-506 (2001).

Tettelin et al., "Complete genome sequence of a virulent isolate of *Streptococcus pneumoniae*" *Science* 293:498-506 (2001).

Tong et al., "Comparison of structural changes of cell surface carbohydrates in the eustachian tube epithelium of chinchillas infected with a *Streptococcus pneumoniae* neuraminidase-deficient mutant or its isogenic parent strain" *Microb. Pathog.* 31:309-317 (2001).

Tong et al., "Evaluation of the virulence of a *Streptococcus pneumoniae* neuraminidase-deficient mutant in nasopharyngeal colonization and development of otitis media in the chinchilla model" *Infection and Immunity* 68:921-924 (2000).

Van Ginkel et al., "Cutting edge: the mucosal adjuvant cholera toxin redirects vaccine proteins into olfactory tissues" *J. Immunol.* 165:4778-4782 (2000).

Van Ginkel et al., "Pneumococcal carriage results in ganglioside-mediated olfactory tissue infection" *PNAS* 100(24):14363-14367 (2003).

Wicker and Scher, "X-linked immune deficiency (xid) of CBA/N mice" *Curr. Top. Microbiol. Immunol.* 124:87-101 (1986).

Winter et al., "A role for pneumolysin but not neuraminidase in the hearing loss and cochlear damage induced by experimental pneumococcal meningitis in guinea pigs" *Infect. Immun.* 65:4411-4418 (1997).

Wu et al., "Nasal lymphoid tissue (NALT) as a mucosal immune inductive site" *Scand. J. Immunol.* 46:506-513 (1997).

Office Action for Canadian Application No. 2,688,009 mailed Sep. 5, 2014 (3 pages).

```
                              10        20        30        40        50
2sli       ( 277 )          ggnIFyag------------------------------------
1eur       (  47 )          geplytegdLavngre----------------------------
3sil       (   4 )          ekgvVFkaeggHhFtdqkgntiv6--------------------
1kit       ( 217 )          vIFrG---------------------------------------
QUERY TARG                  TAELPKGRVRLYVNGVLSRTSLKSGNFIKDMPDVTHVQIGATKRANNTVW 60        70        80        90       100
2sli       ( 285 )          --------------------------------------------
1eur       (  63 )          --------------------------------------------
3sil       (  27 )          --------------------------------------------
1kit       ( 222 )          --------------------------------------------
QUERY TARG                  GSNLQIKNLTVYNRALTPEEVQKRSQLFKRSDLEKKLPEGAALTEKTDIF 110       120       130       140       150
2sli       ( 285 )          ---------dvTeSnYFKIRLLitLst--gtVIgAADAKIGGThdsK--SS
1eur       (  63 )          ------------gfpnYi_IPALTVTpd--gdLLASYDGRptgidap---gp
3sil       (  27 )          --------sGsgqITkyFRIRANCTTsk--gTIVVFADNRntasdq---gf
1kit       ( 222 )          ---------------pDrIPSIVASsvtpqVVTAFAEKkvgggdpGalsRt
QUERY TARG                  ESGKNGNPNKDGIKSYRIPALLKTD--KGTLIAGADERKLHSSDWGD---
                                                      bbbbbbbb      bbbbbbbb 160       170       180       190       200
2sli       ( 323 )          INIAFAKstdgGntysePtipLk-FddYiaknidgpzdsvGknvgIgggA
1eur       (  97 )          NsILQrzStdgGrtYgegqVsa-Ggtts-----------------pik
3sil       (  66 )          IDTAAAKStdgGktY-nkkIAIyNdzvns----------------kls
1kit       ( 256 )          NdIIrtSzdgCityatslaITeqiSvs------------------def
QUERY TARG                  IGMVIRRSEDNGKTWSDRVTITNLRDNPKASDPS-----------IG
                            bbbbbbbb         bbbb 210       220       230       240       250
2sli       ( 372 )          SYldPVLLEDk---ltkrIFLFADLMP-AglGss--nAsvgSGfkevngkk
1eur       ( 126 )          GfsdPSYLVDy---etgtIFNFKVySq--rggfa--qSrp----------
3sil       (  97 )          EVNDPTQIVAnigqreYILVMVGkWNandktWg--ayrd-----------
1kit       ( 289 )          DFSdPRPIYdp--ssnkVlVSYARWp-tdAAqngdgikp-----------
QUERY TARG                  SPVNIDMVLVQDFETKRIFSIYDMFPE-GKGIFSNSSQKEBAYKKIDGKT
                            bbbbbbbbbb       bbbbbbbbb        3

260       270       280       290       300
2sli       ( 417 )          yLkLywbkdagraydyTIRekgvIynaatngptefrVdgeynLyqhdtnl
1eur       ( 161 )          --------------------------------------------------
3sil       ( 134 )          --------------------------------------------------
1kit       ( 325 )          --------------------------------------------------
QUERY TARG                  YQILYREGKKG---AYTIRENGTVYTPDGKATDYRVV-------------

310       320       330       340       350
2sli       ( 467 )          tckgydInfsgnnLiesktdvdvnmNIFYknSvFKAfpINYLANzyadde
1eur       ( 161 )          ------------------------gtdpa------dpnVLRAnVAtgtgg
3sil       ( 134 )          ------------------------kapdt------dadLvLykStdd
1kit       ( 325 )          ------------------------wmpngifySvtdVa
QUERY TARG                  VDPVKPAYSDKGDLYKGDQLLGNIYPTTNKTSPFRIAKDSYLWMSYSDDD
                                                                       bbbbbbb 360       370       380       390       400
2sli       ( 517 )          GaswsdLdI-vSsfKp--evRhfLVVSPGlGkgIstge-----nagRLLV
1eur       ( 181 )          Gltwshrt--ITadIipdpgwriRfAASGqgiQLrygp-----hagRLIQ
3sil       ( 151 )          GvtFskvetnIkdlVtkngtISAMLGSVCSGlgln--------dgkLVF
```

FIG. 25A

```
1kit        ( 339 )  sonwqaPi--------------vnPGPQHSitLtrQqnIsgSqnqRLIY
QUERY TARG           GKTNSAPQ--DITPMVKADWMKFLGVSPSTSIVLRNGP-----HKGRILI
                        bbbb        bbbb   bb bb              bbb 410       420       430       440       450
2sli        ( 559 )  PLySks-------sAELGFMySddXCdnHtyvsAdalt----------gG
1eur        ( 224 )  QYIIna----agafgAVSVYSddXStQrAgeAvg-------------v
3sil        ( 192 )  PVQMVrtkni-ttvlnTSFIyStd-GitMslps----------gyCeG
1kit        ( 571 )  PAIvLdr-----fflgVmgiySdSgGsngqtgstLpipfrwkssssilgtL
QUERY TARG           PVYTTNNVSHLDGSQSSRVIYSDDMQKTWHAGSEAVNDNRQVDGQKIHSST
                         bbbbb       bbbbbbbb      bb E647
                           ▼460      470       480       490       500
2sli        ( 592 )  -------atAEAQIVeMpdGsLKTYIIbtg----------sncIAeVTSigGG
1eur        ( 257 )  -------gMdSNKTVELSdgrVLNgrDsaI--------sgvEkvAvgtdSg
3sil        ( 228 )  -------fgSENKIIef-SsSLVMNIrns----------glBrgfeTkdfG
1kit        ( 616 )  -------ePSsADNVElqnGdLLLIArLdfnqiVngvnyapEQQFIskdGG
QUERY TARG           MNNRRAQNTESTVVQLNNGDVKLFMR----------GLTGDLQVATSKDGG
                         bbbbb     bbbbb              bbbbb 510       520       530       540       550
2sli        ( 637 )  stModrvpLq---gIstTsygTQLSVInks--qpid-----gkpAIILSS
1eur        ( 294 )  HsYgpvtid-----rdLpDPINNASIrsAfpdapaggarAk---vLLFSS
3sil        ( 261 )  ktWteFppMdkkV--dNrnhCVQSSTitIpgg---------nklVAAgSS
1kit        ( 660 )  itMslleannanvFsnistgtVDASIirFsgs--------dgs--hFLLFTW
QUERY TARG           VTMEKDIKRYPQ-------------VKDVYQMSAIHTMHEGKEYIILGN
                         bb                 bbbbbb          bbbbbbb 560       570       580       590       600
2sli        ( 687 )  Pnat-----ngGkncKIwIGLVudkgntgidkysVsWkysyaVdt---pqm
1eur        ( 336 )  AAgg-----tsQsQGTIrngcdGg----------tSpvskvFqpgs---
3sil        ( 300 )  AqNk--nndytgSdISLyAHNLyeg---------svklIdgFypkvgnas
1kit        ( 702 )  PgGnpagtngtqnLGLMFgfdeGv---------twkgpigLvnga----
QUERY TARG           AGGPK-----RENGMVHLA--------RVEENGELTWLKHNPIQKGE----
                         b         bbbbbb          bbbbb Y752
                           ▼      610       620       630       640       650
2sli        ( 710 )  gYSYSCLAsLpd---qqVGLLYEkYdswarnelHIkdiLkFekys-igeL
1eur        ( 368 )  -MsySTLtaLp---dgtYGLLYEP-g----------tGIrYAnFg-lawL
3sil        ( 339 )  gAGYSCLsygknVdketLYVVYSA-n----------GsIefDdL--eghL
1kit        ( 738 )  -SayEDIygLd---sepAIVIVEtdn---------SnMrilrmpIttllk
QUERY TARG           -FAYNSLQELG---NGEYGILYSH------TEKGQNAYTLSFRKFNWEPLS
                         bbbbb      bbbbbb       bbbbbb    aaaa 660
2sli        ( 756 )  tqqa
1eur        ( 402 )  gg--icap
3sil        ( 376 )  pvIksyn
1kit        ( 774 )  gkltlsqn
QUERY TARG           KNLISPTEAN
```

FIG. 25B

DETOXIFIED PNEUMOCOCCAL NEURAMINIDASE AND USES THEREOF

STATEMENT REGARDING FEDERALLY FUNDED RESEARCH

This invention was made with government support under Grants DC 04976, AI 21548, and P30 DK 54781 from the National Institutes of Health and under contract NO1 AI 65299 from the National Institute of Allergy and Infectious Diseases. The government may have certain rights in the invention.

BACKGROUND

*Streptococcus pneumoniae* is a rather ubiquitous human pathogen, which can infect several organs including lungs, the central nervous system (CNS), the middle ear, and the nasal tract. Infection of these tissues results in various symptoms such as bronchitis, pneumonia, meningitis, and sinus infection. *S. pneumoniae* is a major cause of bacterial meningitis in humans and is associated with significant mortality and morbidity despite antibiotic treatment. Quagliarello et al., (1992) N. Eng. J. Med. 327: 869-872. *S. pneumoniae* meningitis can cause persistent neurological sequelae. The incidence of *S. pneumoniae* meningitis in developed versus developing countries are 1-2 and 20 per 100,000 population, respectively. Anon, (2000) CDSC European Bacterial Meningitis Surveillance Project. The fatality rate of pneumococcal meningitis in the USA is approximately 18%. Fedson et al., (1994) Arch. Intern. Med. 154:2531-2535. The highest incidence of pneumococcal meningitis occurs in children between 1-4 years of age (30% of all bacterial meningitis), followed by 15-19 year olds (14%) and 1-11 month old infants (13%). Anon, (2000) CDSC European Bacterial Meningitis Surveillance Project. The elderly are also seriously affected by streptococcal meningitis in both developed and developing countries. Butler et al., (1999) Drugs Aging 15 (Suppl. 1): 11-19; Fedson et al., (1999) Vaccine 17 Suppl. 1: S11-18.

The major reservoir of pneumococci in the world resides in human nasal carriage. Acquisition of infection is generally from a carrier and infection is always preceded by nasal carriage. The colonization of the nasopharynx is considered a prerequisite for the spread of pneumococci to the lower respiratory tract, the nasal sinuses, and the middle ear. Thus, any medical intervention that prevented carriage would not only eliminate the risk of disease in the treated individuals but would also result in herd immunity and greatly lower the risk of infection even in untreated members of the community. Although *S. pneumoniae* is an important human pathogen, relative little is known about the mechanisms by which *S. pneumoniae* causes either nasal carriage or meningitis.

SUMMARY OF THE INVENTION

Provided herein are compositions designed to reduce or prevent bacterial infections (for example pneumococcal infections), nasal carriage, nasal colonization, and CNS invasion. Optionally, the compositions can be designed for mucosal administration. Provided herein are compositions comprising a polypeptide comprising the amino acid sequence of SEQ ID NO:19. The compositions, including, for example, SEQ ID NO:19 and variants thereof, can be detoxified. The compositions can also comprise a variant of SEQ ID NO:19 that can elicit an anti-neuraminidase immune response.

Also provided are methods of generating in a subject an immune response and/or antibodies to pneumococcal neuraminidase comprising administering to the subject a composition comprising a described agent. For example antibodies can be generated in a subject by administering a polypeptide comprising the amino acid sequence of SEQ ID NO:19 or a variant thereof that can elicit an anti-neuraminidase immune response to the subject. The compositions, including, for example, SEQ ID NO:19 and variants thereof, can be detoxified. Optionally, the composition can be suitable for administration to a mucosal surface or for systemic administration.

Further provided is a composition comprising antibodies to a pneumococcal neuraminidase, or an antigenic portion thereof, along with a pharmaceutically acceptable carrier. Optionally, the composition can be suitable for administration to a mucosal surface or for systemic administration.

Further provided are methods of reducing or preventing nasal carriage, nasal colonization, or bacterial infection (for example pneumococcal infection) in a subject comprising contacting the nasal mucosa of the subject with a composition taught herein.

BRIEF DESCRIPTION OF THE DRAWINGS

The accompanying drawings, which are incorporated in and constitute a part of this specification, illustrate several aspects described below.

FIGS. 25 A and B show an exemplary Fugue alignment between SEQ ID NO:41, which is SEQ ID NO:19 minus the first amino acid, and leech (*Macrobdella decora*) intramolecular trans-sialidase complexed with 22, 7-Anhydro-Neu5AC (2sli) (SEQ ID NO:37), *Vibrio cholerae* Neuraminidase (1kit) (SEQ ID NO:40), *Micromonospora viridifaciens* sialidase (1eur) (SEQ ID NO:38) and *Salmonella typhimurium* sialidase (3sil) (SEQ ID NO:39).

DETAILED DESCRIPTION

Figure 1:
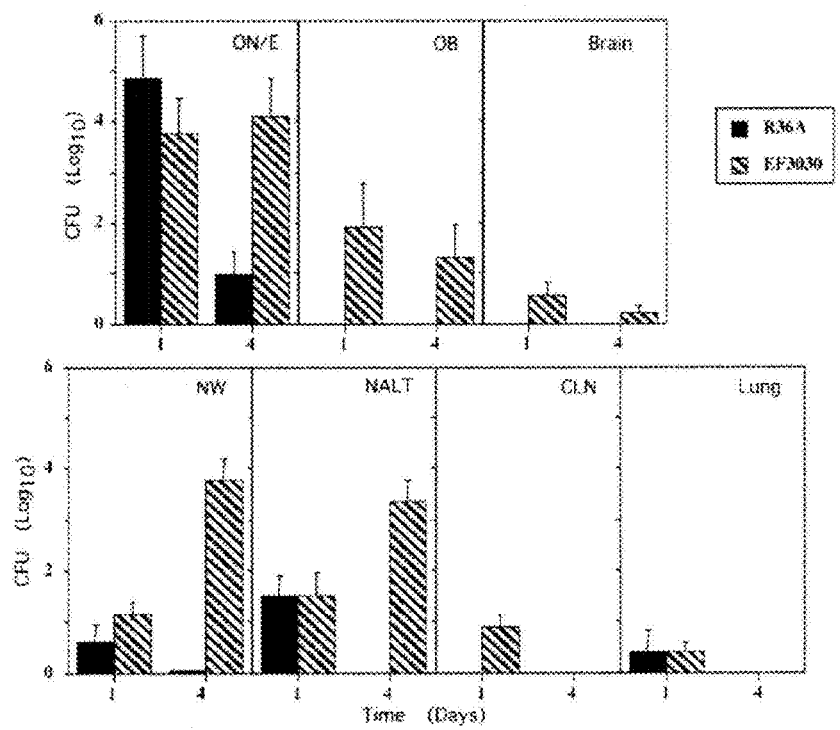
FIG. 1 shows nasal delivery of $3 \times 10^6$ CFU of either the nonencapsulated R36A strain or the virulent EF3030 strain of *S. pneumoniae* to xid mice. The neuronal tissues, nasal olfactory nerves and epithelium (ON/E), olfactory bulb (OB), and brain, and the lymphoid tissues (NR, NALT, CLN and lungs) were collected, minced, and analyzed for the presence of live pneumococci at 1 and 4 days after nasal challenge. Indicated is the mean of $\log_{10}$ colony forming units (CFUs)+one standard error (SE). The 0 value on the Y-axis represents the absence of detectable CFUs. Indicated are the mean CFUs+ SE of 5 mice per group, each mean being representative of three different experiments.

Some data exist to suggest that neuraminidases are unique virulence factors for the nasal tract. One such observation comes from the study of the NanA-deficient, *S. pneumoniae* strain D39, which is eliminated faster from the nasopharynx than is its parent strain. Tong et al., (2002) Infect. Immun. 68: 921-924. Neuraminidase cleaves terminal sialic acid residues from a wide variety of glycolipids, glycoproteins, and oligosaccharides on the host cell surfaces and in body fluids. Elevated levels of free sialic acid in the cerebrospinal fluid (CSF) of patients with pneumococcal meningitis are associated with a poor prognosis. O'Toole et al., (1971) J. Clin. Invest. 50: 979-985. The importance of this enzyme for *S. pneumoniae* virulence in humans is further illustrated by the findings of two independent studies where every new clinical isolate of *S. pneumoniae* had neuraminidase activity. O'Toole et al., (1971) J. Clin. Invest. 50: 979-985; Kelly et al., J. Bacteriol. 94: 272-273. Moreover, mouse passage of isolates of pneumococci, which frequently increases their virulence, has been reported to also result in 2-5-fold increase of neuraminidase activity. Vishniakova et al., (1992) Zhurnal Mikrobiologii, Epidemiologii i Immunobiologii 9-10: 26-9. Pneumococcal C-polysaccharide, also known as teichoic acid, is structurally identical to the polysaccharide portion of pneumococcal F-antigen, also known as lipoteichoic acid. Fischer et al., (1993) Eur. J. Biochem 215: 851-857. These molecules are unique features of *S. pneumoniae* among gram-positive bacteria. The immunodominant determinants on these molecules are the phosphorylcholine (PC) residues and Abs to PC are protective against intraperitoneal, intravenous, or nasal pneumococcal challenge. Briles et al., (1984) Eur. J. Immunol. 14: 1027-1030; Briles et al., (1981) Nature 294: 88-90; Yother et al., (1982) Infect. Immun. 36: 184-188; Briles et al., (1984) J. Mol. Cell. Immunol. 1:305-309. However, as all of these studies assessed protection against systemic infection mediated by serum, no information is available regarding the ability of these Abs to protect against nasal colonization. Surface phosphocholine residues are, however, common on the surface of respiratory bacteria. Lysenko, et al., (2000) Infect. Immun. 68:1664-71.

The mechanisms by which *S. pneumoniae* causes nasal carriage and subsequent disease are relatively unknown. No studies to date have determined a mechanism by which nasal carriage is reduced or prevented. Since colonization of the nasopharynx is considered a prerequisite for the spread of pneumococci to the lower respiratory tract, to the nasal sinus, to the circulation, and to the brain, what is needed in the art is a means of providing mucosal immunity at the site of initial pneumococcal colonization. Preventing initial pneumococcal colonization in the nasopharynx, prevents nasal carriage and reduces spread of *S. pneumoniae* between individuals. Moreover, providing immunity at the mucosal surfaces of the nasopharynx prevents or reduces subsequent disease caused by *S. pneumoniae*.

Provided herein are compositions and methods designed to reduce or prevent bacterial infections (for example pneuomococcal infections), nasal carriage, nasal colonization, and CNS invasion. *S. pneumoniae* colonizes the nasal tract in part by crossing the epithelial barrier through C-polysaccharide-ganglioside interactions with subsequent endocytosis into epithelial cells. C-polysaccharide binds to asialo-GM1, asialo-GM2, and fucosyl-asialo-GM1 through binding to a terminal or internal GalNAcβ1-4Gal sequence in the ganglioside.

The abundancy of these asialogangliosides in the plasma membrane of cells is normally low, with the exception of the human lungs, which can be colonized by S. pneumoniae. Also, S. pneumoniae has its own two neuraminidases NanA and NanB (Berry et al., (1996) J. Bacteriol. 178: 4854-4860), which can each cleave α-2,3- and α-2,6-linkages of N-acetylneuraminic acid to galactose, and α-2,6-linkage to N-acetylgalactosamine to remove sialic acid from intact gangliosides. Scanlon et al., (1989) Enzyme 41: 143-150. Sialic acid residues on gangliosides are a 2,3 linked to galactose. Neuraminidases of S. pneumoniae remove end-terminal sialic acid residues, which are present on all monosialogangliosides, and galactose-linked multiple sialic acid residues, as seen in the di- and trisialogangliosides. Thus, they should be able to expose the GalNAcβ1-4Gal sequence found in the most common mammalian cell surface gangliosides. These residues are the presumed C-polysaccharide binding site on the cell surface.

Using its NanA, which is normally more cell wall associated, and NanB, which is thought to be secreted, S. pneumoniae generates its own attachment sites on epithelial cells in the respiratory tract. Thus, pneumococcal C-polysaccharide binds to asialogangliosides, in particular asialo-GM1, and the neuraminidases, which can convert the rather abundant GM1 into asialo-GM1, may create abundant binding sites on ON/E for the C-polysaccharide. This mechanism facilitates nasal carriage and provides access for S. pneumoniae to the CNS through the nasal olfactory nerves and epithelium covering the nasal turbinates (ON/E), olfactory bulbs (OB). Similarly, otitis media and other infections involving S. pneumoniae can similarly gain access to the CNS through nerves innervating the middle ear. Other bacteria in addition to S. pneumoniae have comparable neuraminidases, thus the same mechanism occurs in other bacteria as well. Thus disclosed herein are compositions and methods targeting this mechanism in a variety of bacteria. The agents, compositions, and methods taught herein are directed to interrupting this mechanism to reduce carriage and to prevent CNS invasion.

Provided herein are compositions including a pneumococcal neuraminidase or an antigenic portion thereof comprising the amino acid sequence of SEQ ID NO:19 or a variant thereof that can elicit an anti-neuraminidase immune response. Further provided are compositions comprising a polypeptide having the amino acid sequence of SEQ ID NO:19 or a variant thereof that can elicit an anti-neuraminidase immune response and a pharmaceutically acceptable carrier. Suitable variants of SEQ ID NO:19 include, but are not limited to E647T (SEQ ID NO:35), R663H, E647Q and Y752F (SEQ ID NO:36). The compositions and polypeptides, including, for example, SEQ ID NO:19 and variants thereof, can be detoxified. Thus, for example, provided are compositions comprising a detoxified pneumococcal neuraminidase or an antigenic portion thereof comprising the amino acid sequence of SEQ ID NO:19 or a variant thereof that can elicit an anti-neuraminidase immune response. In some forms, the pneumococcal neuraminidase or an antigenic portion thereof or detoxified pneumococcal neuraminidase or an antigenic portion thereof does not consist of SEQ ID NO:15 or SEQ ID NO:16.

Optionally, the compositions can be designed for mucosal administration. For example, provided herein is a composition comprising a pneumococcal neuraminidase or an antigenic portion thereof and a pharmaceutically acceptable carrier, wherein the composition is suitable for administration to a mucosal surface. Optionally, the composition can comprise a polypeptide comprising the amino acid sequence of SEQ ID NO:19 or a variant thereof that can elicit an anti-neuraminidase immune response.

Optionally, the composition can be in the form of an aerosol, nasal mist, nasal spray, nasal drops, a nebulizer solution, an aerosol inhalant, a suppository, or any form appropriate for mucosal administration (including oral administration). Optionally, the compositions can be in microspheres or in liposomes for delivery.

By administration to a mucosal surface is meant administration to any mucosal surface including the respiratory system, the gastrointestinal system, or the urogenital system. Examples of mucosal surfaces include but are not limited to the nasal cavity (including to the olfactory neuroepithelium), the nasopharynx, the rectum, the vagina, the larynx, the mouth, the Eustachian tube, the trachea, the bronchi and other airways, and the intestinal mucosa.

For administration to a mucosal surface, a mucosal adjuvant can be used. The adjuvant can be administered concomitantly with the composition of the invention, immediately prior to, or after administration of the composition. Optionally, the composition further comprises the adjuvant. Mucosal adjuvant formulations include, for example, an agent that targets mucosal inductive sites. The adjuvant can optionally be selected from the group including, but not limited to, cytokines, chemokines, growth factors, angiogenic factors, apoptosis inhibitors, and combinations thereof. When a cytokine is chosen as an adjuvant, the cytokine can be selected from the group including, but not limited to, interleukins including IL-1, IL-1γ, IL-1β, IL-2, IL-5, IL-6, IL-12, IL-15 and IL-18; transforming growth factor-beta (TGF-β); granulocyte macrophage colony stimulating factor (GM-CSF); interferon-gamma (IFN-γ); or other cytokine which has adjuvant activity. Portions of cytokines, or mutants or mimics of cytokines (or combinations thereof), having adjuvant activity or other biological activity can also be used in the compositions and methods of the present invention.

When a chemokine is chosen as an adjuvant, the chemokine can optionally be selected from a group including, but not limited to, Lymphotactin, RANTES, LARC, PARC, MDC, TARC, SLC and FKN. When an apoptosis inhibitor is chosen as an adjuvant, the apoptosis inhibitor can optionally be selected from the group including, but not limited to, inhibitors of caspase-8, and combinations thereof. When an angiogenic factor is chosen as an adjuvant, the angiogenic factor can optionally be selected from the group including, but not limited to, a basic fibroblast growth factor (FGF), a vascular endothelial growth factor (VEGF), a hyaluronan (HA) fragment, and combinations thereof. Indeed, plus (+) and minus (−) angiogenic factors can be chosen as adjuvants.

Other examples of substantially non-toxic, biologically active mucosal adjuvants of the present invention include hormones, enzymes, growth factors, or biologically active portions thereof. Such hormones, enzymes, growth factors, or biologically active portions thereof can be of human, bovine, porcine, ovine, canine, feline, equine, or avian origin, for example, and can be tumor necrosis factor (TNF), prolactin, epidermal growth factor (EGF), granulocyte colony stimulating factor (GCSF), insulin-like growth factor (IGF-1), somatotropin (growth hormone) or insulin, or any other hormone or growth factor whose receptor is expressed on cells of the immune system.

Adjuvants for mucosal administration also include bacterial toxins, e.g., the cholera toxin (CT), the E. coli heat-labile toxin (LT), the Clostridium difficile toxin A and the pertussis toxin (PT), or combinations, subunits, toxoids, chimera, or mutants thereof. For example, a purified preparation of native cholera toxin subunit B (CTB) can be used. Fragments, homologs, derivatives, and fusions to any of these toxins are also suitable, provided that they retain adjuvant activity. Preferably, a mutant having reduced toxicity can be used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110-Asp, and Glu-112-Asp mutants. Other adjuvants, such as RH3-ligand; CpG-motif oligonucleotide; a bacterial monophosphoryl lipid A (MPLA) of, e.g., *E. coli, Salmonella minnesota, Salmonella typhimurium*, or *Shigella flexneri*; saponins (e.g., QS21), or polylactide glycolide (PLGA) microspheres, can also be used in mucosal administration. Possible other mucosal adjuvants are defensins and CpG motifs containing oligonucleotides.

As used throughout, a pharmaceutically acceptable carrier is meant as a material that is not biologically or otherwise undesirable, i.e., the material can be administered to an individual along with the selected compound without causing any undesirable biological effects or interacting in a deleterious manner with any of the other components of the pharmaceutical composition in which it is contained.

Any of the compositions described herein can be used therapeutically with a pharmaceutically acceptable carrier. The compounds described herein can be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

By a pneumococcal neuraminidase is meant any neuraminidase molecule found in pneumococcal bacteria. By a pneumococcal neuraminidase fragment is meant a fragment of any neuraminidase molecule found in pneumococcal bacteria. Variants thereof include non-naturally occurring polypeptides that retain sequence similarity and one or more functional similarities to these naturally occurring neuraminidases or fragments thereof.

Table 1 shows the alignment of neuraminidases from several species including TIGR4 and R6. Neuraminidase molecules also include, for example, SP1326. The SP1326 amino acid sequence can be accessed via GenBank Acession No. AAK75424. Tettelin, H., et al., (2001) Science 293: 498-506. All of the information, including any amino acid and nucleic acid sequences provided for SP1326 under GenBank Accession No. AAK75424 is hereby incorporated in its entirety by this reference. As identified throughout, unless otherwise noted, the amino acid residues for all amino acid sequences are numbered in accordance with the amino acid sequence of pneumococcal strain R6 as shown in Table 1. From the numbering given for R6, the corresponding numbering for strain TIGR4 can be readily determined from Table 1, which shows alignment of TIGR4 with R6. For example, residue 35 of TIGR4 NanA corresponds to residue 50 of R6 NanA. Similarly, residue 186 of TIGR4 NanA corresponds to residue 200 of R6 NanA.

TABLE 1

```
                    ClustalW (v1.4) multiple sequence alignment

3 Sequences Aligned             Alignment Score = 6332
Gaps Inserted = 32              Conserved Identities = 105
Pairwise Alignment Mode: Slow
Pairwise Alignment Parameters:

Open Gap Penalty = 10.0         Extend Gap Penalty = 0.1
Similarity Matrix: blosum
Multiple Alignment Parameters:

Open Gap Penalty = 10.0         Extend Gap Penalty = 0.1
Delay Divergent = 40%           Gap Distance = 8
Similarity Matrix: blosum
Processing time: 3.5 seconds R6 NanA                   1  MSYFRNRDIDIERNSMNRSVQERKCRYSIRKLSVGAVSMIVGAVVFGTSP    50
TIGR4 NanA                1              MNRSVQERKCRYSIRKLSVGAVSMIVGAVVNGTSP    35
S. typhimirium            1                                                    0

R6 NanA                  51  VLAQEGASEQPLANETQLSGESSTLTDTEKSQPSSETELSGNKQEQERKD   100
TIGR4 NanA               36  VLAQEGASEQPLANETQLSGESSTLTDTEKSQPSSETELSGNKQEQERKD    85
S. typhimirium            1                                                    0

R6 NanA                 101  KQEEKIPRDYYARDLENVETVIEKEDVETNASNGQRVDLSSELDKLKKLE   150
TIGR4 NanA               86  KQEEKIPRDYYARDLENVETVIEKEDVETNASNGQRVDLSSELDKLKKLE   135
S. typhimirium            1                                                    0

R6 NanA                 151  NATVHMEFKPDAKAPAFYNLFSVSSATKKDEYFTMAVYNNTATLEGRGSD   200
TIGR4 NanA              136  NATVHMENKPDAKAPAFYNLNSVSSATKKDEYFTMAVYNNTATLEGRGSD   185
S. typhimirium            1                                                    0
```

TABLE 1-continued

ClustalW (v1.4) multiple sequence alignment

| | | | |
|---|---|---|---|
| R6 NanA | 201 | GKQFYNNYNDAPLKVKPGQWNSVTFTVEKPTAELPKGRVRLYVNGVLSRT | 250 |
| TIGR4 NanA | 186 | GKQNYNNYNDAPLKVKPGQWNSVTFTVEKPTAELPKGRVRLYVNGVLSRT | 235 |
| S. typhimirium | 1 | MTVEKSVVFKAEG----------EHF | 16 |
| | | ****        *            * | |
| | | | |
| R6 NanA | 251 | SLRSGNFIKDMPDVTHVQIGATKRANNTVWGSNLQIRNLTVYNRALTPEE | 300 |
| TIGR4 NanA | 236 | SLRSGNFIKDMPDVTHVQIGATKRANNTVWGSNLQIRNLTVYNRALTPEE | 285 |
| S. typhimirium | 17 | TDQKG--------------------NTIVGS------------------ | 27 |
| | | . *                        **. ** | |
| | | | |
| R6 NanA | 301 | VQKRSQLFKRSDLEKKLPEGAALTEKTDIFESGRNGKPNKDGIKSYRIPA | 350 |
| TIGR4 NanA | 286 | VQKRSQLNKRSDLEKKLPEGAALTEKTDIFESGRNGNPNKDGIKSYRIPA | 335 |
| S. typhimirium | 28 | -------------------------------GSGG-----TTKYFRIPA | 40 |
| | | * .*         * .**** | |
| | | | |
| R6 NanA | 351 | LLKTDKGTLIAGADERRLHSSDWGDIGMVIRRSEDNGKTWGDRVTITNLR | 400 |
| TIGR4 NanA | 336 | LLKTDKGTLIAGADERRLHSSDWGDIGMVIRRSEDNGKTWGDRVTITNLR | 385 |
| S. typhimirium | 41 | MCTTSKGTIVVFADARHNTASDQSFIDTAAARSTDGGKTWNKKIAIYNDR | 90 |
| | | .  * ***.. ** *. .**   *      ** *.****....* * * | |
| | | | |
| R6 NanA | 401 | DNPKASDPSIGSPVNIDMVLVQDPETKRIFSIYDMFPEGKGIFGMSSQKE | 450 |
| TIGR4 NanA | 386 | DNPKASDPSIGSPVNIDMVLVQDPETKRINSIYDMFPEGKGINGMSSQKE | 435 |
| S. typhimirium | 91 | VNSKLSR-------------VMDP------------------------- | 101 |
| | | * * *           * ** | |
| | | | |
| R6 NanA | 451 | EAYKKIDGKTYQILYREGEKGAYTIRENGTVYTPDGKATDYRVVVDPVKP | 500 |
| TIGR4 NanA | 436 | EAYKKIDGKTYQILYREGEKGAYTIRENGTVYTPDGKATDYRVVVDPVKP | 485 |
| S. typhimirium | 102 | ---------TCIVANIQG-------RE--TILVMVGKWNNN----DKTWG | 129 |
| | | *   .*       ** *. **. *      * | |
| | | | |
| R6 NanA | 501 | AYSDKGDLYKGNQLLGNIYFTTNKTSPFRIAKDSYLWMSYSDDDGKTWSA | 550 |
| TIGR4 NanA | 486 | AYSDKGDLYKGDQLLGNIYFTTNKTSPNRIAKDSYLWMSYSDDDGKTWSA | 535 |
| S. typhimirium | 130 | AYRDK-------------------AP---DTDWDLVLYKSTDDGVTFSK | 156 |
| | | ** **                        .*     *   * .  *** ** * | |
| | | | |
| R6 NanA | 551 | PQDITPMVKADWMKFLGVGPGTGIVLRNGPHKGRILIPVYTTNNVSHLNG | 600 |
| TIGR4 NanA | 536 | PQDITPMVKADWMKFLGVGPGTGIVLRNGPHKGRILIPVYTTNNVSHLDG | 585 |
| S. typhimirium | 157 | VETNIHDIVTKNGTISAMLGGVGSGLQLN--DGKLVPPVQMVR-TKNITT | 203 |
| | | .     ..      . * * *..  *... **         .. | |
| | | | |
| R6 NanA | 601 | SQSSRIIYSDDHGKTWHAGEAVNDNRQVDGQKIHSSTMNNRRAQNTESTV | 650 |
| TIGR4 NanA | 586 | SQSSRVIYSDDHGKTWHAGEAVNDNRQVDGQKIHSSTMNNRRAQNTESTV | 635 |
| S. typhimirium | 204 | VLNTSFIYSTD-GITWSLPSGYCEGFGSE---------NN---------I | 234 |
| | | .  *** * * **           ..   .          **            . | |
| | | | |
| R6 NanA | 651 | VQLNNNGDVKLFMRGLTGDLQVATSKDGGVTWEKDIKRYPQVKDVYVQMSA | 700 |
| TIGR4 NanA | 636 | VQLNNNGDVKLNMRGLTGDLQVATSKDGGVTWEKDIKRYPQVKDVYVQMSA | 685 |
| S. typhimirium | 235 | IEFN-ASLVNNIR-NSGLRRSFETKDFGKTWTEFPPMDKKVDNR------ | 276 |
| | | .. *      . *     .*    .* .   ** * **         .* | |
| | | | |
| R6 NanA | 701 | IHTMHEGKEYIILSNAGGPKRENGMVHLARVEENGELTWLKHNPIQKGEF | 750 |
| TIGR4 NanA | 686 | IHTMHEGKEYIILSNAGGPKRENGMVHLARVEENGELTWLKHNPIQKGEN | 735 |
| S. typhimirium | 277 | ----NHGVQGSTITIPSG----NKLVAAHSSAQNKNNDYTRSDISLYAHN | 318 |
| | | . *   ..   *     * .*       .* | |
| | | | |
| R6 NanA | 751 | AYNSLQELGNGEYGILYEHTEKGQNAYTLSFRKFNWDFLSKDLISPTEAK | 800 |
| TIGR4 NanA | 736 | AYNSLQELGNGEYGILYEHTEKGQNAYTLSNRKNNWENLSKNLISPTEAN | 785 |
| S. typhimirium | 319 | LYSGEVKLIDDFYPKVGNAS--GAGYSCLSYRKN---VDKETLYVVYEAN | 363 |
| | |  *       *    *    . *   .** **        *     ** | |
| | | | |
| R6 NanA | 801 | VKRTREMGKGVIGLEFDSEVLVNKAPTLQLANGKTARFMTQYDTKTLLFT | 850 |
| TIGR4 NanA | 786 | NRDGQRR---------------DGQRSYWLGVRLRSIGQQGSNPSIGK | 818 |
| S. typhimirium | 364 | ----------------------------------------------GS | 365 |
| | | | |
| R6 NanA | 851 | VDSEDMGQKVTGLAEGAIESMHNLPVSVAGTKLSNGMNGSEAAVHEVPEY | 900 |
| TIGR4 NanA | 819 | WNNSDNPNPVN---------NQDLVVCSRNGRYRTGNYWYSNRKHRKYAN | 859 |
| S. typhimirium | 366 | IEFQDLSRHLP-------------VIKSYN (SEQ ID NO: 17) | 382 |
| | | *       . | |
| | | | |
| R6 NanA | 901 | TGPLGTSGEEPAPTVEKPEYTGPLGTSGEEPAPTVEKPEYTGPLGTAGEE | 950 |
| TIGR4 NanA | 860 | SSCKSSR----CQSSWRSKWNQSSGANSSR----IYR-------GSNWYR | 894 |
| S. typhimirium | 383 | | 382 |
| | | | |
| R6 NanA | 951 | AAPTVEKPEFTGGVNGTEPAVHEIAEYKGSDSLVTLTTKEDYTYKAPLAQ | 1000 |
| TIGR4 NanA | 895 | ASCSNNR--RVNGINFACNSYYKKRLYLQSSSCSAGTSNNRK-------Q | 935 |
| S. typhimirium | 383 | | 382 |

TABLE 1-continued

ClustalW (v1.4) multiple sequence alignment

```
R6 NanA           1001 QALPETGNKESDLLASLGLTAFFLGLFTLGKKREQ (SEQ ID NO: 15) 1035
TIGR4 NanA         936 GENPPSFTRTN--------SNLPWSVYAREKERTI (SEQ ID NO: 16)  962
S. typhimirium     383                                                      382
```

Any antigenic variant of neuraminidase or of a neuraminidase fragment can also be used in the compositions or methods taught herein. Thus, the naturally occurring neuraminidase or fragments thereof can be modified by substitution, deletion, and/or alteration of amino acid residues in accordance with the methods taught herein. Optionally, such modifications will be designed to detoxify the neuraminidase or neuraminidase fragment. For example, SEQ ID NO:19 can be detoxified. The neuraminidase or neuraminidase fragment can also comprise a variant of SEQ ID NO:19 that can elicit an anti-neuraminidase immune response.

By detoxification is meant a reduction or elimination in enzymatic activity, preferably while maintaining antigenicity or immunogenicity. This can be accomplished by substitution, deletion, or alteration of amino acids in the active site of the neuraminidase using site specific mutagenesis. Each substitution, deletion, or alteration of amino acids can be made at one or more amino acid residue positions. Unless otherwise noted, the amino acid position numbering corresponds to the R6 strain shown in Table 1. Based on the R6 strain positions, however, one can readily determine the corresponding residue position for other strains including the TIGR4 strain also shown in Table 1.

One substitution that can optionally be made includes the substitution the Tyrosine residue 752 of R6 (737 of TIGR4), as shown in Table 1, with a Phenylalanine A second optional substitution that can be made includes substituting the Glutamic Acid residue at position 647 of R6 (632 of TIGR4) as shown in Table 1, with Threonine. Mutagenesis, including these two optional substitutions, can be performed using, for example, the QuickChange® mutagenesis method from Stratagene (La Jolla, Calif.). Using this method, oligonucleotide primers containing the desired change can be used in PCR on template comprising the existing rNanA571 plasmid. DpnI can be used to deplete any unmodified template remaining at the end of the PCR cycles. The PCR product can be used to transform high-efficiency competent cells of an *E. Coli* host strain. The transformants can be sequenced to verify the mutation. The primer used can be:

```
Mutant E647T:
                                          SEQ ID. NO: 31
Sense: 5'-cgcaaaatacaacctcaacggtggtac-3'

SEQ ID. NO: 32
Antisense: 5'-gtaccaccgttgaggttgtattttgcg-3'

Mutant Y752F:
                                          SEQ ID. NO: 33
Sense: 5'-aaggagagtttgcctttaattcgctccaag-3'

Seq ID. NO: 34
Antisense: 5'-cttggagcgaattaaaggcaaactctcctt-3'
```

Crennell et al., (1993) demonstrates that the enzyme active site in the sialidase of *Salmonella typhimurium* contains a key tyrosine and glutamic acid, as well as an arginine triad and a hydrophobic pocket. Crennell et al., PNAS 90:9852-9856, is incorporated herein by reference in its entirety for the neuraminidase structure taught therein. The two key active site tyrosine and glutamic acid amino acids correspond to Y752 and E647 in the *S. pneumoniae* neuraminidase. (Numbers given here relative to NanA_R6 or SEQ ID NO:15). In Kleineidam et al., alteration of the equivalent key amino acids in the small sialidase of *C. perfringens* A99 resulted in the inactivation of the sialidase. See, Kleineidam et al., Biol Chem 382:313-319 (2001), which is incorporated herein by reference for the structures taught therein.

Alternatively, substitutions, deletions, or alterations can be within other amino acids that appear to be conserved amino acid residues and also conserved in their relative structural location when observed in an alignment run by Fugue, a program for alignment of sequences using structural information. See, Shi, J. et al., FUGUE: sequence-structure homology recognition using environment-specific substitution tables and structure-dependent gap penalties. J Mol Biol 310:243-257 (2001), which is incorporated by reference for the methods taught therein. An exemplary Fugue alignment between SEQ ID NO:19 and leech (*Macrobdella decora*) intramolecular trans-sialidase complexed with 22, 7-Anhydro-Neu5AC (2sli), *Vibrio cholerae* Neuraminidase (1kit), *Micromonospora viridifaciens* sialidase (1eur) and *Salmonella typhimurium* sialidase (3sil) is shown in FIGS. 25 A and B.

Some of these additional conserved amino acids outside of the two key active site tyrosine and glutamic acid amino acids include R347, I348, P349, D362, R364, Y608, R663, 5714, R721, W739, Y767, and E768. (Numbers given here relative to NanA_R6 or SEQ ID NO:15) Arginine R347, I348 and P349 are conserved between bacterial, human and viral neuraminidases. R364R663 and R721 are homologous to the three arginines that form the active site triad in the *Salmonella* enzyme. Some of the others participate in the hydrophobic pocket that is part of the active site.

Substitutions, deletions, or alterations can also occur within the Asp boxes within amino acid residues 383-390, 541-548, 609-616 or 674-681. The aromatic residues within the Asp box end up in the hydrophobic core (serine and tryptophan), and can dampen or abolish enzymatic activity, while the aspartic residues themselves are pointed out toward solvent and, as such, can also be used for detoxification purposes. Alterations in the Asp boxes can include replacement of aspartic acid with glutamic acid or threonine, for example. Other conservative or non-conservative amino acid replacements can also be used at the aspartic acid residue or any other residue in the Asp boxes to reduce toxicity. Other regions of the neuraminidase are optionally targeted for site-specific mutagenesis.

Also disclosed are neuraminidases or fragments thereof with modifications in the regions corresponding to residues 750-760, and more specifically the tyrosine at position 752. Conservative amino acid substitutions for the tyrosine residue include, for example, serine or threonine, while a non-conservative substitution can be phenylalanine. Also provided are neuraminidases with modifications in the regions corresponding to amino acid residues 340-350, 600-610, or 360-370. More specifically, the arginines at positions 347, 364, 663, or 721 can be substituted with lysine or glutamine, or any other conservative or non-conservative amino acids. The various modifications taught herein can be used in combination. Thus, one or more conservative or non-conservative amino acid substitutions can be optionally present in the same neuraminidase.

The decreased activity of a detoxified neuraminidase or a neuraminidase fragment as compared to non-detoxified neuraminidase can be measured by the assay of Lock, et al. (Microb. Pathog. 4: 33-43, 1988). Using the Lock assay, NanA activity in lysates, serum, or blood can be measured using 2'-(4-methyl-umbelliferyl)-α-D-N-acetylneuraminic acid as the substrate in a enzyme assay (Lock et al. 1988). Ten microliters of substrate are combined with 10 µL of serum and incubated for 5 minutes at 37° C. The reaction is stopped using 0.5M sodium carbonate. Neuraminidase activity is measured in terms of the amount of 4-methylumbelliferone (MU) released per minute. MU has an excitation wavelength of 366 nM and an emission wavelength of 445 nm. It is preferred that the detoxified neuraminidase retain antigenicity or immunogenicity comparable to that of non-detoxified neuraminidase, such that it can be combined with a pharmaceutically acceptable carrier to form an immunological composition. For purposes of comparison, non-detoxified neuraminidase includes, but is not limited to, R6 NanA as shown in Table 1. In preferred embodiments, detoxified neuraminidase or fragments thereof exhibit less than 1%, 10%, 20%, 30%, 40%, 50%, 60%, 70%, 80%, or 90% of the enzymatic activity of a non-detoxified neuraminidase. Thus the detoxified neuraminidase or fragments thereof can exhibit less than 1% of the activity of a non-detoxified neuraminidase. Thus, the detoxified neuraminidase or fragment thereof can have no measurable enzymatic activity as compared to the enzymatic activity of a non-detoxified neuraminidase. Further, the detoxified neuraminidase can have protective antibody eliciting activity similar to the non-detoxified neuraminidase.

Detoxified neuraminidase or detoxified neuraminidase fragments can include alterations (i.e., substitutions, modifications, or deletions) in its amino acid sequence as compared to non-detoxified neuraminidase or fragments. In preferred embodiments, detoxified neuraminidase includes alteration of approximately 7%, 10%, 15% or 20% of the amino acids found within non-detoxified neuraminidase. Preferred amino acid deletions include the deletion of approximately 5, 10, 15 or more amino acids from the N-terminus of non-detoxified neuraminidase. Other preferred embodiments include the deletion of approximately 60, 50, 40, 30, 20, 10, 5 or more amino acids of the C-terminus of non-detoxified neuraminidase (for the purposes of this application, the C-terminus begins at amino acid 800 of R6 NanA as shown in Table 1). In yet other preferred embodiments, detoxified neuraminidase includes deletion of 17, 9, 8, 7, 4 or 2 amino acids of the C-terminus of non-detoxified neuraminidase. Certain exemplary preferred deletions are illustrated in Table 1 (i.e., the TIGR4 NanA amino acid sequence). Any of these alterations can be combined with one or more other alterations. It is preferred that such detoxified neuraminidase species exhibit approximately less than 1%, 10%, 20%, 30%, 40%, 50%, 60%, 70%, 80%, or 90% of the enzymatic activity of a non-detoxified neuraminidase.

Other conservative and non-conservative substitutions in neuraminidase or fragments thereof, in such as, for example, SEQ ID NO:19 or variants thereof that can elicit an anti-neuraminidase immune response, can be used. It is preferred that the neuraminidase or its fragment maintains its antigenicity or immunogenicity. These conservative substitutions are such that a naturally occurring amino acid is replaced by one having similar properties. Such conservative and nonconservative substitutions optionally alter the enzymatic function of the polypeptide. For example, conservative substitutions can be made according to Table 2.

TABLE 2

Amino Acid Substitutions

| Original Residue | Exemplary Substitutions |
|---|---|
| Arg | Lys |
| Asn | Gln |
| Asp | Glu |
| Cys | Ser |
| Gln | Asn |
| Glu | Asp |
| Gly | Pro |
| His | Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

It is understood that, where desired, modifications and changes can be made in the nucleic acid encoding the polypeptides of this invention and/or amino acid sequence of the polypeptides of the present invention and still obtain a polypeptide having like or otherwise desirable characteristics (e.g., antigenicity or immunogenicity). Such changes can occur in natural isolates or can be synthetically introduced using site-specific mutagenesis, the procedures, such as mismatch polymerase chain reaction (PCR), are well known in the art. For example, certain amino acids can be substituted for other amino acids in a polypeptide without appreciable loss of functional activity. It is thus contemplated that various changes can be made in the amino acid sequence of the polypeptides of the present invention (or underlying nucleic acid sequence) to result in a loss or reduction of enzymatic activity and the maintenance of antigenicity or immunogenicity.

Deletions of the nanA gene or any portion of the nanA gene can be carried out using the method described by Sung et al., (2001) Appl Environ Microbiol 67: 5190-5196, which is incorporated herein by reference in its entirety for the methods taught therein. The reagent 2, 3 butadione, which specifically reacts with Arg residues of proteins, is used to assess the importance of Arg residues to the folding of the NanA molecule. Site-directed mutagenesis can be used to alter specific amino-acids.

The neuraminidase can also be detoxified by chemical treatment, including for example denaturation. Chemical treatment can also be combined with site-specific mutagenesis to further reduce negative side effects and improves antigenicity or immunogenicity. The detoxified neuraminidase can be treated with an agent such as formalin, glutaraldehyde, heat, or with other agents known to those skilled in the art, prior to immunization of a subject with the detoxified neuraminidase.

Provided herein is a pneumococcal neuraminidase or an antigenic or immunogenic portion thereof. For example, a polypeptide comprising the amino acid sequence of SEQ ID NO:19 is provided. Optionally the neuraminidase or fragment, including polypeptides comprising SEQ ID NO:19, can be detoxified. The polypeptide can also comprise a variant of SEQ ID NO:19, optimally a detoxified variant, that can elicit an anti-neuraminidase immune response.

Also provided are compositions comprising the detoxified pneumococcal neuraminidase or fragments thereof and a pharmaceutically acceptable carrier. For example, the composition can comprise a polypeptide comprising the amino acid sequence of SEQ ID NO:19. SEQ ID NO:19 can be detoxified as described herein. Optionally, the composition further comprises an adjuvant (including, for example, a mucosal adjuvant). The polypeptide can also comprise a variant of SEQ ID NO:19 that can elicit an anti-neuraminidase immune response.

Additional amino acid residues can be added to SEQ ID NO:19 or the variant thereof that can elicit an anti-neuraminidase immune response so long as the fragment maintains its antigencity or immunogenicity. For example, SEQ ID NO:18 comprises SEQ ID NO:19 and additional residues from a cloning vector as described in Example 10.

Furthermore, other moieties can be added to the neuraminidase or fragment thereof, including to SEQ ID NO:19 or to a variant thereof that can elicit an anti-neuraminidase immune response. For example, moieties that increase antigenicity or immunogenicity can be added. Such moieties include, for example, cytokines, chemokines, growth factors, angiogenic factors, apoptosis inhibitors, hormones, toxins, or other moieties discussed herein for use as adjuvants. The moieties can optionally be modified or truncated for use in the altered molecules. Thus, provided herein is a pneumococcal neuraminidase chimera comprising the neuraminidase or an antigenic or immunogenic fragment thereof, such as, for example, SEQ ID NO:19 or a variant thereof that can elicit an anti-neuraminidase immune response, and a moiety that enhances antigenicity or immunogenicity. Also provided are compositions comprising the pneumococcal neuraminidase derivatives, such as, for example, SEQ ID NO:19 or a variant thereof that can elicit an anti-neuraminidase immune response, and a pharmaceutically acceptable carrier. Optionally the composition further comprises an adjuvant (including, for example, a mucosal adjuvant).

Optionally the modified neuraminidase fragment or portion thereof of the invention has an amino acid sequence with at least about 70% homology with a naturally occurring pneumococcal neuraminidase or fragment thereof. For example, the amino acid sequence can have at least about 70% homology with SEQ ID NO:19.

Further provided are nucleic acids that encode the modified neuraminidases or fragments thereof. It is understood that one way to define any known variants and derivatives or those that might arise, of the disclosed nucleic acids and proteins herein is through defining the variants and derivatives in terms of homology to specific known sequences. For example, the amino acid sequence encoded by the nanA gene of the R6 pneumococcal strain as shown in Table 1 sets forth a particular sequence of a pneumococcal neuraminidase and sets forth a particular amino acid sequence of the protein. Moreover, the amino acid sequence encoded by the nanA gene of the R6 or TIGR4 pneumococcal strain corresponding to SEQ ID NO:19 sets forth a particular sequence of a pneumococcal neuraminidase and sets forth a particular amino acid sequence of the protein. Specifically disclosed are variants of this sequence herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

By an antigenic portion thereof or an immunogenic portion thereof is meant any epitope of a molecule or compound (e.g., neuraminidase, phosphocholine, a pneumococcal teichoic acid, a pneumococcal lipoteichoic acid) that elicits an immune response, such as a humoral immune response, a cellular immune response, or antibody production, wherein the immune response is directed to the molecule. Preferably, the antigenic portion elicits immunity to the molecule or to *S. pneumoniae*. Preferably the antibodies can be directed to or interfere with active sites of the neuraminidase.

One form of immune response that can be elicited by the disclosed neuraminidases and compositions can be an anti-neuraminidase immune response. By anti-neuraminidase immune response is meant an immune response that is directed to one or more neuraminidases, such as, for example, bacterial neuraminidases, pneumonococcal neuraminidases, *S. pneumoniae* neuraminidases, NanA and NanB. Preferred anti-neuraminidase immune responses are those that neutralize one or more neuraminidases. For example, an anti-neuraminidase immune response that neutralizes a neuraminidase can reduce or eliminate the enzymatic activity of the neuraminidase. A neutralizing anti-neuraminidase immune response can be assessed in any suitable way. The immune response can be the generation of antibodies that can bind to one or more neuraminidases. It is preferred that the immune response not be directed to or against a neuraminidase of the animal, such as, for example, a mouse or human, in which the immune response is generated. Thus, for example, it is preferred that the immune response is directed to one or more neuraminidases, such as, for example, bacterial neuraminidases, pneumonococcal neuraminidases, *S. pneumoniae* neuraminidases, NanA and NanB, but not to human neuraminidases.

A useful way to assess and determine that a given detoxified, modified or variant neuramindase or fragment thereof can elicit an anti-neuraminidase immune response is to administer the detoxified, modified or variant neuramindase or fragment thereof to an animal such as a mouse or immunize an animal such as a mouse with the detoxified, modified or variant neuramindase or fragment thereof, collect antibodies produced, and test the antibodies for their ability reduce or eliminate enzymatic activity of a neuraminidase of interest, such as for example, a bacterial neuraminidase, a pneumococcal neuraminidase, a *S. pneumoniae* neuraminidase, NanA or NanB. A useful way to measure enzymatic activity of the neuraminidase of interest is by the method of Lock et al. (Microb. Pathog. 4: 33-43, 1988).

Other ways to assess and determine that a given detoxified, modified or variant neuramindase or fragment thereof can elicit an anti-neuraminidase immune response is to administer the detoxified, modified variant neuramindase or fragment thereof to an animal such as a mouse or immunize an animal such as a mouse with the detoxified, modified or variant neuramindase or fragment thereof, challenge the animal with *S. pneumoniae* and assess colony forming units that can be recovered from or found in the animal, such from or in nasal washes, nasal tissue, olfactory bulbs, blood, lung, and brain from the animal, or assess nasal carriage in any suitable way.

The antigenic portions described herein have amino acid residues numbered according to the R6 strain NanA shown in Table 1. Each antigenic portion described in relation to the numbering of R6 NanA has corresponding NanA amino acids from other strains, including TIGR4 NanA, which is also shown in Table 1. To elicit protection against nasal colonization, the peptide portion of NanA used for immunization can be large enough to maintain its overall conformational structure. Thus, modifications of SEQ ID NO:19 can be made wherein its overall conformational structure is maintained.

Examples of antigenic fragments include, but are not limited to, residues corresponding to residues 63-361 of the nanA-R6 amino acid sequence, in the presence or absence of conservative amino acid substitutions or modifications. Other examples include the Asp regions of neuraminidase (corresponding to residues 383-390, 541-548, 609-616 and 674-681 of the NanA-R6 amino acid sequence) and regions corresponding to 340-350, 360-370, 568-578, 600-610, 760-770 of the NanA-R6 amino acid sequence, in the presence or absence of conservative amino acid substitutions or modifications. Optionally, the antibodies directed to interfere with active sites of neuraminidase can bind to or prevent binding to arginine residues of NanA located at residue 347, 364, 663 or 721 of SEQ ID NO:15, or to Asp-boxes of NanA located at residues 383-390, 541-548, 609-616 and 674-681 of SEQ ID NO:15. Moreover, the antibodies can also bind or prevent binding to valine located at residue 575 of SEQ ID NO:15 or tyrosine located at residue 752 of SEQ ID NO:15. The antibody can also bind to or prevent binding to any combination of the above listed residues of SEQ ID NO:15.

Other examples of NanA fragments include amino acids 1 to 340, 330 to 630, 620 to 800, 700 to 1030 and 330 to 800 of R6 NanA. Further provided are fragments that are fusions of two or more of these fragments. Fused fragments include, but are not limited to, regions 1 to 340 fused with regions 620-680. Fused fragments can be expressed as a recombinant protein. Fragments that encode these fragments can be cloned into an expression vector (pET Vectors; Novagen, Inc.) and the protein is purified.

Another example of NanA fragments can include SEQ ID NO:19 in the presence or absence of conservative amino acid substitutions or modifications. SEQ ID NO:19 is a 571 amino acid residue fragment corresponding to amino acid residues 230-800 of SEQ ID NO:15 (R6 NanA) and to amino acid residues 215-785 of SEQ ID NO:16. Substitutions, mutations or deletions of SEQ ID NO:19 can be made as described above. One substitution that can optionally be made includes the substitution the Tyrosine residue 752 of R6 (737 of TIGR4), as shown in Table 1, with a Phenylalanine. A second optional substitution that can be made includes substituting the Glutamic Acid residue at position 647 of R6 (632 of TIGR4) as shown in Table 1, with Threonine. Any of the various modifications mentioned herein can be combined in one neuraminidase or fragment thereof.

Fragments can be generated as a synthetic polypeptide from a vector. Fragments can be used to immunize animals to generate antibodies and to crystallize in order to assess three-dimensional structures. Further provided are nucleic acids encoding the fragments in the presence or absence of conservative or non-conservative amino acid modifications, or substitutions, as described herein. Also provided are vectors or expression systems comprising the nucleic acids.

Provided herein are compositions comprising isolated antibodies that specifically bind pneumococcal neuraminidase or fragments thereof including SEQ ID NO:19. Such antibodies are useful in developing passive immunity to *S. pneumoniae*. The antibody compositions further comprise a pharmaceutically acceptable carrier. Optionally, the composition can be suitable for administration to a mucosal surface, but other routes of administration are disclosed, including systemic administration as described herein.

Also disclosed herein are methods of generating antibodies specific to pneumococcal neuraminidase, or any epitope of pneumococcal neuraminidase, including SEQ ID NO:19, or any epitope of SEQ ID NO:19. Optionally, the antibodies can be generated in a subject (i.e., in vivo) by contacting the nasal mucosa of the subject with an effective amount of a composition disclosed herein. Also, disclosed is a method of generating antibodies specific to any combination of pneumococcal neuraminidase, including SEQ ID NO:19, by contacting the nasal mucosa of the subject with an effective amount of a composition comprising a combination of neuraminidases and/or fragments thereof.

Optionally, the agents described herein, whether naturally occurring, detoxified or otherwise modified, can optionally be administered as a nucleic acid, for example, within a vector. Expression of the nucleic acid would then result in contacting the subject with the desired polypeptide expressed thereby. Thus, for example, if a nucleic acid encoding pneumococcal neuraminidase or SEQ ID NO:19, is administered to a subject in a form that can be expressed within the subject, then the subject is contacted with the neuraminidase.

In the methods described herein, which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by gene gun or other delivery methods such as electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., Proc. Natl. Acad. Sci. U.S.A. 85:4486, 1988; Miller et al., Mol. Cell. Biol. 6:2895, 1986). The recombinant retrovirus can then be used to infect and thereby deliver to the infected cells nucleic acid encoding for example pneumococcal neuraminidase or a broadly neutralizing antibody (or active fragment thereof). The exact method of introducing the nucleic acid into mammalian cells is, of course, not limited to the use of retroviral vectors. Other techniques are widely available for this procedure including the use of adenoviral vectors (Mitani et al., Hum. Gene Ther. 5:941-948, 1994), adeno-associated viral (AAV) vectors (Goodman et al., Blood 84:1492-1500, 1994), lentiviral vectors (Naidini et al., Science 272:263-267, 1996), pseudotyped retroviral vectors (Agrawal et al., Exper. Hematol. 24:738-747, 1996). Physical transduction techniques can also be used, such as liposome delivery and receptor-mediated and other endocytosis mechanisms (see, for example, Schwartzenberger et al., Blood 87:472-478, 1996). This disclosed compositions and methods can be used in conjunction with any of these or other commonly used gene transfer methods.

As one example, if the antibody-encoding nucleic acid is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, Hum. Gene Ther. 8:985-1001, 1997; Alvarez and Curiel, Hum. Gene Ther. 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., Remington: The Science and Practice of Pharmacy (19th ed.) ed. A.R. Gennaro, Mack Publishing Company, Easton, Pa. 1995.

Also disclosed is a method of reducing or preventing pneumococcal nasal carriage in a subject comprising contact of the nasal mucosa of the subject with an effective amount of a composition disclosed herein. Such administration can be useful in generating active or passive immunity to or protection against pneumococcal infection or nasal carriage.

Further provided is a method of reducing or preventing pneumococcal infection in a subject comprising contact of a mucosal surface of the subject with an effective amount of a composition disclosed herein. For example, the method can prevent pneumococcal meningitis, otitis media, pneumonia, or hemolytic uremia. Prevention or reduction can occur by reducing nasal carriage and or preventing CNS invasion, systemic invasion, or invasion of the Eustachian tubes or lower airways.

By the term effective amount of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact effective amount. However, an appropriate effective amount can be determined by one of ordinary skill in the art.

The dosages or amounts of the compositions described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied. Preferred dosages include for nasal applications of antigen between about 1-1000 µg per immunization or any amount in between, including for example 10-100 µg.

The efficacy of administration of a particular dose of the compounds or compositions according to the methods described herein can be determined by evaluating the particular aspects of the medical history, signs, symptoms, and objective laboratory tests that are known to be useful in evaluating the status of a subject with pneomococcal infection or who is a pneumococcal carrier. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: 1) a subject's physical condition is shown to be improved (e.g., nasal carriage is reduced or eliminated), 2) the progression of the disease, infection, or nasal carriage is shown to be stabilized, slowed, or reversed, or 3) the need for other medications for treating the disease or condition is lessened or obviated, then a particular treatment regimen will be considered efficacious. For example, reducing or preventing nasal carriage in a subject or in a population, avoiding or reducing the occurrence of CNS invasion or other secondary pneumococcal infections would indicate efficacy. Such effects could be determined in a single subject (e.g., by reducing the number of bacteria detected with a traditional swab of the mucosal surface) or in a population (e.g., using epidemiological studies).

The compounds and pharmaceutical compositions described herein can be administered to the subject in a number of ways depending on whether local or systemic treatment is desired, and on the area to be treated. Thus, for example, a compound or pharmaceutical composition described herein can be administered intravenously, subcutaneously, intramuscularly, encapsulated in liposomes or microspheres, as an ophthalmic solution and/or ointment to the surface of the eye, as a nasal spray, as a nebulized solution, or as an aerosol to the nasal cavities or airways. Moreover, a compound or pharmaceutical composition can be administered to a subject vaginally, rectally, intranasally, orally, by inhalation, orally, or by intubation. Optionally, the composition can be administered by intravenous, subcutaneous, intramuscular, or intraperitoneal injection. The composition can be prepared in conventional forms, either as liquid solutions or suspensions, solid forms suitable for solution or suspension in liquid, or as emulsions. Optionally, administration can be by slow release or sustained release system such that a constant dosage is maintained. See, e.g., U.S. Pat. No. 3,610,795, which is incorporated by reference herein for the methods taught therein.

The compositions taught herein include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's, or fixed oils. Preservatives and other additives can also be present such as, for example, antimicrobials, anti-oxidants, chelating agents, and inert gases and the like.

Formulations for local administration can include ointments, lotions, creams, gels, drops, suppositories, sprays, liquids, aerosols, nebulizer solutions and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

Provided herein are methods of reducing or preventing nasal carriage or pneumococcal infection in a subject comprising administering to a subject an effective amount of a neuraminidase inhibitor. Preferably, the neuraminidase inhibitor inhibits pneumococcal neuraminidase activity without significantly reducing the subject's endogenous neuraminidase. Thus, for example, if the neuraminidase is administered to a human, the inhibitor will preferably inhibit pneumococcal neuraminidase without reducing the human neuraminidase activity, or without reducing human neuraminidase activity such that negative side-effects result in the human. Examples of known neuraminidase inhibitors include DANA, NANA, zanamivir and oseltamivir.

Provided herein is a method of reducing or preventing nasal carriage or pneumococcal infection in a subject comprising administering to a subject an effective amount of a composition comprising antibodies or fragments thereof against pneumococcal neuraminidase or antibodies against a portion of any neuraminidases. For example, an antibody against SEQ ID NO:19 can be administered. Optionally, this administration comprises contacting a mucosal surface of the subject with the composition. Also provided are compositions and containers containing the antibodies.

Antibodies of the invention can also preferentially bind to antigenic portions of a neuraminidase or a fragment thereof. For example, antibodies of the invention can preferentially bind to antigenic portions of SEQ ID NO:19.

The term antibodies is used herein in a broad sense and includes both polyclonal and monoclonal antibodies. Chimeric antibodies, and hybrid antibodies, with dual or multiple antigen or epitope specificities, and fragments, such as F(ab')2, Fab', Fab, scFv, and the like, including hybrid fragments can also be used in the compositions and methods described herein. Thus, fragments of the antibodies that retain the ability to bind their specific antigens are provided. For example, fragments of antibodies which maintain neuraminidase binding activity are included within the meaning of the term antibody fragment. Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Conjugates of antibody fragments and antigen binding proteins (single chain antibodies) can be used in the composition of the invention. Such conjugates are described, for example, in U.S. Pat. No. 4,704,692, the contents of which are hereby incorporated by reference. The antibodies can be tested for their desired activity using in vitro assays, or by analogous methods, after which their in vivo therapeutic and/or prophylactic activities can be tested according to known clinical testing methods.

The term monoclonal antibody as used herein refers to an antibody obtained from a substantially homogeneous population of antibodies, i.e., the individual antibodies within the population are identical except for possible naturally occurring mutations that may be present in a small subset of the antibody molecules. The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes can be immunized in vitro, e.g., using the HIV Env-CD4-co-receptor complexes described herein.

The monoclonal antibodies can also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross linking antigen.

The antibody fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term antibody or antibodies can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response. Thus, the compositions comprising antibodies optionally comprise humanized or fully human antibodies. Antibody humanization techniques generally involve the use of recombinant DNA technology to manipulate the DNA sequence encoding one or more polypeptide chains of an antibody molecule. Accordingly, a humanized form of a non human antibody (or a fragment thereof) is a chimeric antibody or antibody chain (or a fragment thereof, such as an Fv, Fab, Fab', or other antigen binding portion of an antibody) which contains a portion of an antigen binding site from a non-human (donor) antibody integrated into the framework of a human (recipient) antibody.

The disclosed human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1): δ 95, 1991). Human antibodies (and fragments thereof) can also be produced using phage display libraries (Hoogenboom et al., J. Mol. Biol., 227:381, 1991; Marks et al., J. Mol. Biol., 222: 581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551 255 (1993); Jakobovits et al., Nature, 362:255 258 (1993); Bruggermann et al., Year in Immunol., 7:33 (1993)). Specifically, the homozygous deletion of the antibody heavy chain joining region (J(H)) gene in these chimeric and germ line mutant mice results in complete inhibition of endogenous antibody production, and the successful transfer of the human germ line antibody gene array into such germ line mutant mice results in the production of human antibodies upon antigen challenge. Antibodies having the desired activity can be selected using Env-CD4-co-receptor complexes as described herein.

To generate a humanized antibody, residues from one or more complementarity determining regions (CDRs) of a recipient (human) antibody molecule are replaced by residues from one or more CDRs of a donor (non human) antibody molecule that is known to have desired antigen binding characteristics (e.g., a certain level of specificity and affinity for the target antigen). In some instances, Fv framework (FR) residues of the human antibody are replaced by corresponding non human residues. Humanized antibodies can also contain residues which are found neither in the recipient antibody nor in the imported CDR or framework sequences. Generally, a humanized antibody has one or more amino acid residues introduced into it from a source which is non human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522 525 (1986), Reichmann et al., Nature, 332:323 327 (1988), and Presta, Curr. Opin. Struct. Biol., 2:593 596 (1992)).

Methods for humanizing non human antibodies are well known in the art. For example, humanized antibodies can be generated according to the methods of Winter and co workers (Jones et al., Nature, 321:522 525 (1986), Riechmann et al., Nature, 332:323 327 (1988), Verhoeyen et al., Science, 239: 1534 1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Administration of the antibodies can be done as disclosed herein. Nucleic acid approaches for antibody delivery also exist. The antibodies and antibody fragments can also be administered to patients or subjects as a nucleic acid preparation (e.g., DNA or RNA) that encodes the antibody or antibody fragment, such that the subject's own cells take up the nucleic acid and produce and secrete the encoded antibody or antibody fragment. The delivery of the nucleic acid can be by any means known in the art.

Also disclosed herein are containers comprising the agents and compositions taught herein. Specifically, the container can be a nasal sprayer, a nebulizer, an inhaler, a bottle, or any other means of containing the composition in a form for administration to a mucosal surface. Optionally, the container can deliver a metered dose of the composition.

It is to be understood that the aspects described herein are not limited to specific synthetic methods or specific administration methods, as such may, of course, vary. It is also to be understood that the terminology used herein is for the purpose of describing particular aspects only and is not intended to be limiting.

It must be noted that, as used in the specification and the appended claims, the singular forms a, an and the include plural referents unless the context clearly dictates otherwise. Thus, for example, reference to an antigenic fragment includes mixtures of antigenic fragments, reference to a pharmaceutical carrier or adjuvant includes mixtures of two or more such carriers or adjuvants, and the like.

As used throughout, by a subject is meant an individual. Thus, the subject can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about, it will be understood that the particular value forms another aspect. It will be further understood that the endpoints of each of the ranges are significant both in relation to the other endpoint, and independently of the other endpoint.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an inhibitor is disclosed and discussed and a number of modifications that can be made to a number of molecules including the inhibitor are discussed, each and every combination and permutation of the inhibitor and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Nasal Pneumococci Penetrate Olfactory Tissues During Carriage

Materials and Methods
Pneumococcal Strains

The studies employed two encapsulated strains of *S. pneumoniae* EF3030, serotype 19F, and TIGR4 strain, serotype 4 and the avirulent, non-capsular strain R36A derived from the parent strain D39, serotype 2. Avery et al., (1944) J. Exp. Med. 79: 137-158. The EF3030 strain was chosen since it readily colonizes the respiratory tract in the absence of bacteremia (Briles et al., (1992) Infect. Immun. 60: 111-116) and is incapable of sustained bacteremia following intravenous inoculation. The TIGR4 strain was more virulent, but with a modest nasal inoculum colonizes without bacteremia.

Mice

The CBA/CAHN/xid (xid) mouse strain was obtained from the Jackson Laboratory (Bar Harbor, Me.). The mutation in the Bruton's tyrosine kinase gene of these mice results in an inability to respond to thymus-independent type II antigens (Amsbaugh et al., (1972) J. Exp. Med. 136: 931-949; Berning et al., (1980) J. Immunol. 46: 506-513), but permits relatively normal T cell-dependent immune responses. These mice fail to respond to capsular polysaccharides and are reproducibly susceptible to pneumococcal infection. The xid mice were maintained under pathogen-free conditions and were used at 7-12 weeks of age.

Tissue Collection

The blood was collected into a heparinized capillary tube from the retroorbital plexus. Mice were disinfected with 70% ethanol prior to collection of nasal wash (NW), kidney, spleen, and lungs. To prevent blood contamination of the NW an incision was made into the trachea and a 2.0 cm long Tygon tube with an outer diameter of 0.075 cm (Cole-Parmer, Vernon Hills, Ill.) was inserted into the nasopharynx while attached to a syringe filled with Ringer's solution. Fluid from the syringe was expelled through the nose and three drops were collected.

The nasopharyngeal-associated lymphoreticular tissue (NALT), ON/E, OBs and remainder of the brain were obtained as described. van Ginkel et al., (2000) J. Immunol. 165: 4778-4782; Wu et al., (1997) Scand. J. Immunol. 46: 506-513. The trigeminal ganglia were carefully excised from the brain with a dissection microscope. The ON/E, OBs, trigeminal ganglia, NALT and cervical lymph nodes CLNs were each homogenized in 0.5 ml Ringer's solution and the brain and kidney each homogenized in 1.0 ml of Ringer's solution.

Quantity of Pneumococci in Tissue Minces/Blood/External Excretions

Eight serial, three-fold dilutions were made of tissues and body fluids in sterile Ringer's solution and plated on blood agar plates containing 4 µg/ml of gentamicin sulfate. The CFU were enumerated 24 hr after plating and incubation in a candle jar. The results were expressed as CFUs/organ, per NW or per ml of blood.

GLS Preincubation of *S. pneumoniae* Strain EF3030

To block GLS binding sites, $3 \times 10^7$ CFU of *S. pneumoniae* strain EF3030 were incubated for 30 min on ice with either 20 µg asialo-GM1 from human brain or 125 µg of mixed GLSs (18% GM1, 55% GD1a, 15% GD1b, 10% GT1b, 2% other GLSs) from bovine brain (Calbiochem-Novabiochem Corporation, Inc., La Jolla, Calif.). GLSs were dissolved in PBS and extensively mixed a day prior to use. The amphiphilic GLSs formed micelles in PBS allowing interaction of pneumococci with the carbohydrate moiety. Following incubation, 5 µl per nare was applied nasally to xid mice without further washing. Tissues were analyzed for CFUs four days later.

Detection of *S. Pneumoniae* Pneumolysin Gene by PCR

To detect *S. pneumoniae* by PCR, tissues were lysed in 1% SDS with 0.1% deoxycholic acid by freeze-thawing, and incubated at 37° C. for 1 hr. Proteins were removed using the cetyltrimethylammoniumbromide/NaCl precipitation method (Ausubel et al., (1987) Current Protocols in Molecular Biology, $2^{nd}$: 2.4.4, which is incorporated herein by reference for teaching of the cetyltrimethylammoniumbromide/NaCl precipitation method). Ten µg of DNA was used for PCR amplification. The pneumolysin(ply)-specific primers Ply1 5'-ATTTCTGTAACAGCTACCAACGA-3' (SEQ ID NO:1) and Ply2 5'-GAATTCCCTGTCTTTTCAAAGTC-3'

(SEQ ID NO:2) were added to the PCR mixture to amplify a 400 bp fragment. The PCR reaction involved a 5 min denaturation step at 94° C. followed by the amplification cycle: 94° C. (1 min), 55° C. (1 min), and 72° C. (1 min) for 30 cycles. Images of the ethidium bromide stained PCR fragments were collected on an Alpha Imager TM IS-3400 (Alpha Innotech Corporation, San Leandro, Calif.).

Immunofluorescent Staining of OBs with PspA-Specific Abs

Mice were nasally challenged with $5 \times 10^5$ CFU of the TIGR4 strain. The OBs were fixed in 10% buffered formalin. Four μm paraffin sections (van Ginkel (2000) J. Immunol. 165: 4778-4782) were stained for PspA family 2 Abs (1:100) by incubating them for 4 hr at room temperature in a humidified chamber. Slides were washed in PBS, stained with biotinylated goat F(ab')2 anti-rabbit IgG (1:200) (Southern Biotechnology Associates, Inc., Birmingham, Ala.), washed and stained with streptavidin-FITC (1:100) (BD-PharMingen, San Diego, Calif.). Fluorescent images were collected with a Nikon microscope using a DEI-750 CE digital color video camera (Optronics, Goleta, Calif.) and processed with the Scion Image software (Scion Corporation, Frederick, Md.).

Statistics

The data are expressed as the mean±one standard error and the results were compared by statistical analysis to determine significant differences in CFUs using the unpaired Mann Whitney two sample rank test or student t-test.

Results

The Role of the Pneumococcal Capsule in Nasal Colonization and CNS Invasion

To examine the up-take of pneumococci through primary sensory olfactory neurons, the ability of EF3030 and a non-encapsulated strain R36A to colonize the nasal tract and enter the CNS were measured at days 1 and 4 (FIG. 1). Although high CFU for both strains were observed in the ON/E on day 1, the R36A were largely absent by day 4 from the ON/E and all other tissues, consistent with earlier results indicating that some capsule is required for prolonged colonization. Magee and Yother (2001) Infect. Immun. 69: 3755-3761. EF3030 showed a clear presence in the OB and brain on both days and were present in high numbers in the NWs and NALT on day 4. These findings were consistent with axonal transport of EF3030 pneumococci into the OBs and brain after nasal challenge.

Kinetics of Nasal Colonization and CNS Invasion

Figure 2:
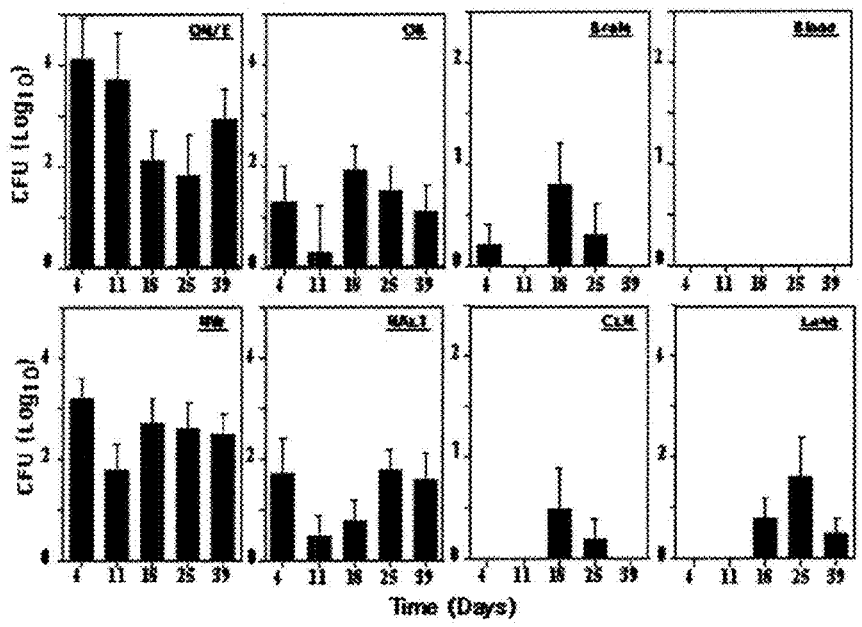
FIG. 2 shows the kinetics of organ distribution of *S. pneumoniae* strain EF3030 CFUs after nasal challenge. The ON/E, OBs, brain, blood, NR, NALT, CLN, and lung tissues were collected on days 4, 11, 18, 25, and 39 and were analyzed for the presence of *S. pneumoniae*. An aliquot of $3 \times 10^6$ CFU of *S. pneumoniae* resulted in the colonization of the nasal tract and a subsequent infection of the OBs. The 0 value on the Y-axis represents the absence of detectable CFUs. Indicated are the mean CFU+SE of three separate experiments. Each time point represents 10 mice with the exception of day 39, which represents 5 mice.

EF3030 was maintained in the ON/E, OBs, NWs, and NALT at all time points over the 39 days of observation (FIG. 2). Much lower numbers of CFU were seen in the brain and CLN, and those CFU present were generally seen at 18 and 25 days. Interestingly, the lungs did not exhibit pneumococci except at day 1 (FIG. 1) and at days 18, 25 and 39 (FIG. 2). Bacteremia did not contribute to the neuronal tissue distribution, since no CFU were detected in the bloodstream of mice during any of the experiments performed with strain EF3030 at the nasal dose used (FIG. 2). Blood was monitored for bacteremia at 1, 3, 6, 12 and 24 hr after nasal application and every subsequent day for one week. No bacteria were detected in the blood.

S. pneumoniae Infection of Trigeminal Ganglia

The trigeminal neurons innervate the nasopharynx and thus, S. pneumoniae would be expected in the trigeminal ganglia after infection of the nasal mucosa. To test this, various tissues and blood were isolated four days after inoculation and analyzed for the presence of EF3030 in new experiments. The EF3030 strain was detected in ON/E and OBs and in trigeminal ganglia (Table 3). This finding further supported that asialo-GM1 function as receptors for neuronal targeting by S. pneumoniae. Other GLSs likely play a role as well.

Table 3 shows the distribution of S. pneumoniae strain EF3030 in various tissues after nasal delivery. Tissues were isolated on day 4 after nasal application of $1 \times 10^7$ CFUs of strain EF3030. Blood (50 μl), ON/E, OBs, and brain tissue minces were diluted and then plated on blood agar. The trigeminal ganglia were pooled, homogenized and then plated on this medium. Indicated are the mean pneumococcal CFUs±SE of 5 mice and are representative of three separate experiments. In the brain and blood no pneumococci were detected.

TABLE 3

| Tissue | Mean CFU ($Log_{10}$) | SE |
| --- | --- | --- |
| Brain | 0 | |
| Olfactory bulbs | 1.38 | 0.61 |
| ON/E | 4.93 | 0.42 |
| Blood | 0 | |
| Trigeminal ganglia | 2.08 | (pooled) |

Gangliosides Inhibit Pneumococcal Colonization

The EF3030 strain was incubated with asialo-GM1 or mixed GLSs micelles in PBS prior to nasal application. The GLS mixture displayed the strongest inhibitory effect and reduced CFU in NW by 10 fold (P=0.0365) when assessed four days after nasal application. The largest decline in CFU as a result of mixed GLS preincubation was seen in the ON/E (617-fold decline; P=0.0134). Just as striking were the differences in the lungs (P=0.0320) (FIG. 3) and CNS tissue (P=0.0078) (FIG. 3), where an average of 204 and 166 CFU were present in the controls, while pneumococci were undetectable (detection limit=3 CFU) when incubated with GLSs. The asialo-GM1 preincubation was less efficient than mixed GLSs but still reduced colonization 25- and 63-fold in CNS (FIG. 3) and lungs (FIG. 3), respectively. The lungs were infected by inhaled pneumococci and their attachment to asialo-GM1, relatively abundantly present in lungs, was apparently inhibited by GLSs. This indicates that GLSs play a role in the initial attachment to epithelial cells. GLS treatments did not change pneumococcal viability. No pneumococci were detected in the blood during these experiments. Thus, GLSs constitute an important target for pneumococcal attachment to neuro-epithelium of the nasal tract and infection of lungs and CNS.

Detection of S. pneumoniae Accumulation in the OBs Following Nasal Challenge

Figure 3:
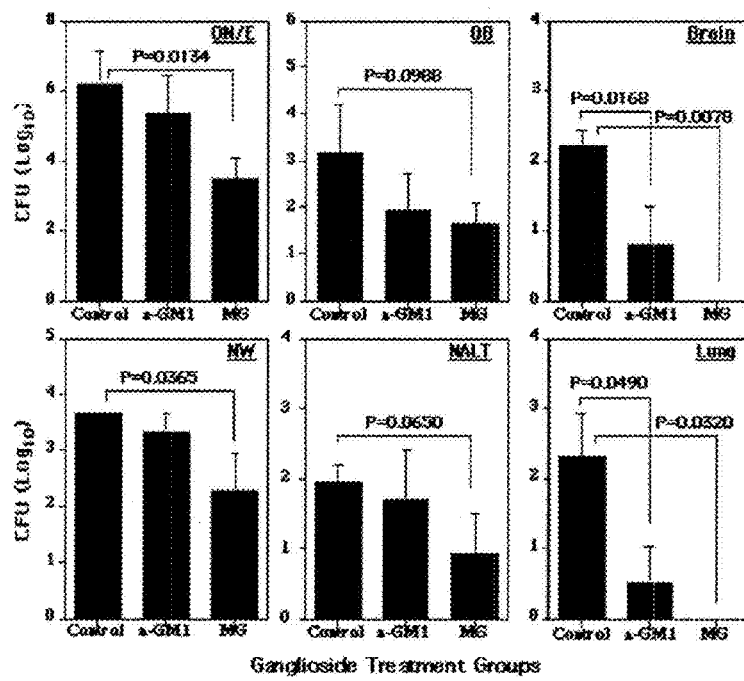
FIG. 3 shows the distribution of *S. pneumoniae* strain EF3030 following preincubation with gangliosides (GLSs). Aliquots ($3 \times 10^7$ CFUs) of *S. pneumoniae* were incubated for 30 minutes with 20 μg asialo-GM1 (a-GM1) or 125 μg of mixed GLSs (MG) prior to nasal application. The ON/E, OBs, brain and NR, NALT and lungs were collected four days later and analyzed for numbers of *S. pneumoniae*. The 0 value on the Y-axis represents the absence of detectable CFUs. Indicated are the mean+one SE of 5 mice and the P-values were obtained following statistical analysis with the Student's t-test or the Mann-Whitney two sample rank test, as appropriate for the data examined. The data are representative of two separate experiments.
Figures 4A, 4B, 4C:
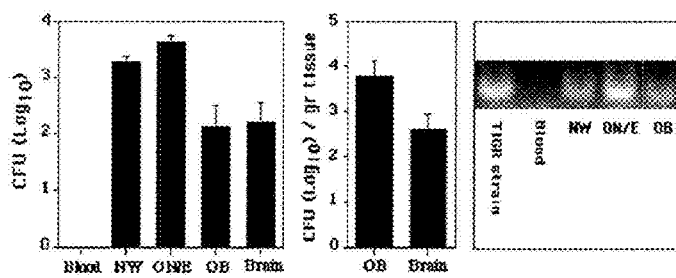
FIGS. 4A-F show detection of the TIGR4 strain of *S. pneumoniae* in the OBs following nasal challenge. An aliquot of $5 \times 10^5$ CFU was given nasally and the blood, NWs, ON/E, OBs and brain tissues were analyzed for colonization one week after challenge (FIGS. 4A and 4B). These tissues (10 µg DNA) were also analyzed for the presence of the pneumolysin gene by PCR (FIG. 4C). In addition, the *S. pneumoniae* were visualized by immunofluorescence with PspA-specific Abs in the OBs of control (D) or *S. pneumoniae* challenged mice (panels E and F). Indicated are the mean+one SE. The data are representative of three separate experiments.
Figures 4D, 4E, 4F:
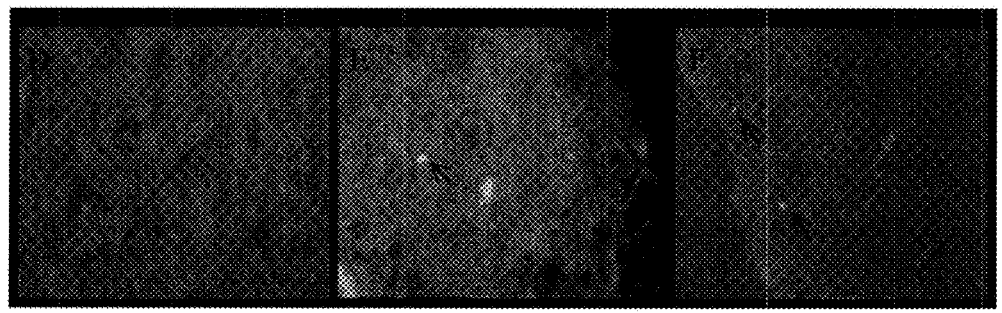

The numbers of EF3030 in OBs were generally too low to make visualization of bacteria by microscopy feasible. To visualize S. pneumoniae in the OBs after nasal application, a more virulent strain, TIGR4, was used. Blood samples were tested from representative mice at 1, 3, 6, 12 or 24 hrs after challenge and on every subsequent day. No bacteremia was observed. The mice were sacrificed one week after challenge and tissues were analyzed for CFU (FIGS. 4A and 4B). A dose of only $5 \times 10^5$ TIGR4CFU resulted in ~300 CFU in the OBs (FIG. 3). The pneumococci were visualized by staining with PspA-specific Abs in the OBs (FIG. 4D-F). Pneumococci were detected in the OBs, i.e., the glomerular layer (FIG. 4F) and the external plexiform layer (FIG. 4E) of challenged mice. Pneumococci were absent in the OBs of control mice (FIG. 4D).

The TIGR4 strain was also detected by PCR amplification of the pneumolysin gene from the NWs, ON/E and OBs 6 days after nasal administration (FIG. 4C). No PCR-detectable pneumococci were present in the bloodstream taken at this interval, or in any samples from non-infected mice.

Example 2

The Role of Pneumococcal-NanA in Nasopharyngeal Carriage and Targeting of the CNS NanA mutants were generated in three strains of *S. pneumoniae* differing both in genetic background and localization of NanA. Strains EF3030 (type 19F) and D39 (type 2) both express a NanA that is covalently attached to the cell wall whereas the TIGR4 strain (type 4) expresses a truncated NanA that is secreted into the environment.

The role of NanB in colonization was also assessed.
Bacterial Strains and Growth Conditions.
Strains used in this study are listed in Table 4.

niques taught therein) (Table 4). Strains TIGR4 and EF3030 were used as recipients for the transformation of donor chromosomal DNA prepared from the isogenic nanA strain D39 (Berry et al. (2000) Infect. Immun. 68:133-140). In each case, the mutants were backcrossed three times into the parental strain. The D39 mutant was also backcrossed three times into our D39 parental strain to make sure it was isogenic with the parental strain used in these studies. The mutation of D39 was made by insertion duplication mutagenesis allowed the deletion of all but an N-terminal fragment of about 650 amino acids of the mature protein (Berry et al. (2000) Infect. Immun. 68:133-140). A TIGR4/nanB isogenic mutant was constructed using insertion duplication mutagenesis techniques (Balachandran et al (2002) Infect. Immun. 70:2536-2534;

TABLE 4

| Strains, plasmids, and primers | genotypes or primer sequences |
|---|---|
| *E. coli* strains | |
| TOP 10F' | |
| *S. pneumoniae* strains | |
| TIGR4 | capsular serotype 4* |
| EF3030 | capsular serotype 19F† |
| D39 | capsular serotype‡ |
| JPC001 | D39/NanA- (insertion duplication)§ |
| JW001 | TIGR4/nanA- (insertion-duplication mutant) |
| JW002 | TIGR4:nanA deletion |
| JW003 | TIGR4 nanB- (insertion-duplication mutant) |
| JW004 | TIGR4 nanAB- (insertion-duplication double mutant) |
| SAM001 | EF3030 nanA- (insertion-duplication mutant) |
| SAM003 | EF3030 nanAB-(insertion-duplication double mutant) |
| Plasmids | |
| pSF152 | Suicide vector for deletion of nanB; spectinomycin resistance |
| pCR4-TOPO | Cloning vector; ampicillin and kanamycin resistance |
| Primers | |
| NAF1 | 5- CGCGGATCCTCATACTGGGTTAGGAAAGTCGTCG-3 (SEQ ID NO: 6) |
| NAF 1.1 | 5- GGAATTCCATATGCCGACAGCAGAACTACCTAAAGGC-3 (SEQ ID NO: 7) |
| NAW 1.1 | 5- GGAATTCCATATGCTGGCAAATGAAACTCAACTTTCGGGGG-3 (SEQI NO: 8) |
| NAP1.1 | 5- CGCGGATCCATCGGCTTTGACCATCGGAG-3 (SEQ ID NO: 9) |
| NAP1.2 | 5- GGAATTCCATATGCGTATTCCAGCACTTCTCAAGACAG-3 (SEQ ID NO: 10) |
| nanBF | 5- GGAACATTACCTCGCAAAAGG-3 (SEQ ID NO: 11) |
| nanBR | 5- TACCCGCAGGCATAACATC-3 (SEQ ID NO: 12) |

*Tettelin et al. (2001) Science 293: 498-506.
†Briles et al. (2003) J Infect Dis 188: 339-348
‡Avery et al. (1979) J. Exp. Med 149: 297-326; McDaniel et al. (1987) Microb. Pathog. 3: 249-260.
§Berry et al. (2000) Infect. Immun. 68: 133-140.

All pneumococcal strains were stored at −80° C. in 10% glycerol and cultured by transfer to blood agar plates and incubated at 37° C. in a 5% CO2 atmosphere overnight. Cultures of pneumococci were grown in Todd-Hewitt Medium containing 0.5% yeast extract to an OD660 of 0.5 and stored frozen in aliquots at −80° C. in the same broth supplement to 10% with sterile glycerol. Mutants carrying antibiotic resistant inserts were grown in the appropriate antibiotics to insure stability of the mutations.

Construction of nanA Mutants.

NanA mutant strains JW001, SAM001, and JCP001 of parental backgrounds TIGR4, EF3030 and D39, respectively, were derived through insertion duplication mutagenesis techniques (Yother (1992) J. Bact. 174:610-618, which is incorporated by reference herein in its entirety for the tech- Yother et al. (1992) J. Bact. 174:610-618). A 461-bp internal portion of nanB was amplified using the primers: nanBF and nanBR (Table 4), PCR was carried out using Taq PCR Mastermix (Invitrogen) and 30 cycles at 95° C. 1 min., 45° C. 1 min., 72° C. 1 min. The fragment was cloned into pSF152. Transformation of the TIGR4 strain with the plasmid DNA were as before (Balachandran et al. (2002) Infect. Immun. 70:2526-2534). A nanA/nanB-TIGR4 double mutant was derived by transformation of the nanB/TIGR4 mutant with chromosomal DNA prepared from strain JW001.

Mouse Virulence Assays.

Female 6-12 week old CBA/CaHN-XID/J (CBA/N) mice were obtained from The Jackson Laboratory (Bar Harbor, Mass.). The mutation in the Bruton's tyrosine kinase gene of these mice results in an inability to respond to thymus-independent type II antigens but permits relatively normal T cell-dependent immune responses (Amsbaugh et al. 1972 J Exp Med. 136:931-949; Briles et al. 1986 Curr. Top. Microbiol. Immunol. 124:103-120; Potter et al. 1999 Int. Immunol. 11:1059-64; Wicker and Scher 1986 Curr. Top. Microbiol. Immunol. 124). These mice fail to respond to capsular polysaccharides and are reproducibly susceptible to pneumococcal infection (Briles et al. 1986 Curr Top. Microbiol. Immunol. 124:103-120; Briles et al. 1981 j. Exp. Med. 153: 694-705). The x-linked immunodeficient (xid) mice were maintained under pathogen-free conditions and were used at 7-12 weeks of age. Frozen infection stocks containing a known concentration of viable cells were diluted in lactated Ringer's solution. Mice were then infected intranasally (I.N.) with approximately $5\times10^5$-$1\times10^6$ cells in a volume of 10 µl as described (Wu et al. 1997b Microb. Pathog 23:127-137).

Tissue Collection.

All mice were euthanized prior to performing nasal washes and tissue collection. The blood was collected into a heparinized capillary tube from the retroorbital plexus. Mice were disinfected with 70% ethanol before collection of nasal wash (NW), nasal tissue (including the olfactory epithelium (NT) olfactory bulbs (OB), and brain. These fluid and tissues were obtained as described above. To prevent blood contamination of the NR, an incision was made into the trachea and a 2.0-cm-long Tygon tube with an outer diameter of 0.075 cm (Cole-Parmer, Vernon Hills, Ill.) was inserted into the nasopharynx while attached to a syringe filled with Ringer's solution. Fluid from the syringe was expelled through the nose, and three drops were collected. The ON/E and OB were each homogenized in 0.5 ml of Ringer's solution while the remainder of the brain was homogenized in 1.0 ml of Ringer's injection solution.

Quantitation of Viable Pneumococci

Eight serial, 3-fold dilutions were made of tissues and body fluids in sterile Ringer's solution and plated on blood agar plates containing 4 µg/ml gentamicin sulfate. The colony forming units (CFU) were enumerated 24 h after plating and incubation at 37° C. in a candle jar. The assay used for neuraminidase activity has been previously described (Lock et al 1988 Microb Pathog 4:33-43, which is incorporated herein by reference in its entirety for the assay methods). Significance of results was assessed by analysis with a two sample Mann-Whitney rank test making comparisons between wild type pneumococci and mutant pneumococci.

In Vitro Studies

The ability of the TIGR4, and its nanA and nanB mutants to bind to specific gangliosides is measured. The gangliosides used include mixed gangliosides, asialo-GM1, GM1, GD1a, GD1b, GT1 (Calbiochem) and the GM3 ganglioside (Sigma). The GM3 ganglioside lacks the terminal or internal GalNAcβ1-4Gal sequence involved in pneumococcal binding and is used as a negative control. These mixed, mono-, di- or tri-sialic acid containing gangliosides bind readily to ELISA plates. Initial data following short-term incubation with the TIGR4 strain indicates that pneumococci bind to asialo-GM1-coated plates but not to BSA-, GM-3, or GM1-coated plates. Using ganglioside-coated plates, the ability to attach to these plates by wildtype TIGR4 strain, the stable opaque and transparent phase variants of the TIGR4 strain, the nanA, nanB, and nanA/nanB mutant strains is compared. These analyses include short-term incubation (1 hr) and extended incubations (24 hrs) on ganglioside-coated plates. Attached pneumococci are removed from the ganglioside plates by short incubation (10-15 min.) in Todd Hewitt medium containing 0.5% yeast extract followed by repeated pipetting and plating the released bacteria on blood agar plates. Alternatively 41° C. Todd Hewitt broth agar containing 0.5% yeast extract is poured on top of the attached pneumococci and the colonies are counted through the bottom of the plate. Controls include plates with no pneumococci and plates with no gangliosides but with pneumococci.

Subsequent to testing ganglioside binding, different cell lines are tested for their ability to attach pneumococci to their cell surface and internalize them. These studies focus on the rat neuronal pheochromocytoma cell line PC12 (ATCC) and the macrophage cell line P388D1. These two cell lines were chosen because of their specific attributes. The P388D1 cell line expresses high affinity PAF-R (Valone (1988) J. Immunol. 140: 2389-2394), which has been reported to be present on microglia. The PC12 cell line does not express detectable PAF-R. Brewer et al., (2002) J. NeuroChem 82: 1502-1511. Between $10^2$-$10^5$ pneumococcal CFU are added to these cell lines grown in 6 well or 24 well tissue culture plates and are incubated at 37° C. for between 15 min. to 6 hrs after which the cells are extensively washed and adherent pneumococci analyzed. To determine internalization into the cells a 2 hr wash with penicillin and gentamicin is performed prior to plating the cells on blood agar or over-laying them with 41° C. Todd Hewitt broth agar containing 0.5% yeast extract. The two cell lines used reflect in vivo expression of the PAF-R normally observed in the CNS. While activated microglia abundantly express this receptor as does the P388D1 cell line, the PAF-R receptor is either absent on neuronal cells, such as the PC12 cell line, or is only expressed at low levels by discrete neuronal subpopulations. Mori et al., (1996) J. Neurosci 16: 3590-3600; Bennett et al., (1998) Cell Dath Differ. 5: 867-875. Adherence of pneumococci to both cell lines would indicate that the PAF-R is not essential for adherence and alternative receptor exist. The TIGR4 opaque and transparent variants and the nanA-, nanB-mutants and nanA/nanB double mutant are tested for adherence to these cell lines relative to that observed with the wildtype TIGR4 strain. To further analyze the role of PAF-R versus gangliosides in pneumococcal adherence, the COS-7 cell line (Gerard and Gerard (1994) J. Immunol. 152: 793-800; Honda et al., (1992) J. Lipid Med. 5: 105-107), which lack PAF-R, are transfected with the human PAFR open reading frame of 1029 bp using the pcDNA3.1/GS plasmid as previously reported (Brewer et al., (2002) J. Neuro Chem 82: 1502-1511, which is incorporated herein by reference in its entirety for the methods taught therein) and tranfected using Transfast reagent (Promega). The plasmid alone is used as a control and the parameters influencing pneumococcal adherence are analyzed in the presence or absence of PAF-R. This experiment provides unequivocal data regarding the importance of PAF-R in adherence. Any adherence in PAF-R deficient cell lines is mediated by gangliosides and is subsequently blocked by preincubation with gangliosides. To further address the ability of pneumococci to attach to and penetrate epithelial cells the Detroit 562 human pharyngeal epithelial cell line (ATCC) and A549 human pulmonary epithelial cell line (ATCC) is employed using a transwell system. The Millicell®-PCF Culture (Millipore, Billerica, Mass.) plate inserts are used to grow the epithelial cell lines to confluency. Confluency is determined by measuring the transepithelial resistance using a Millipore Millicell® electrical resistance system. A resistance of at least 500Ω per $cm^2$ indicates that a fully confluent epithelial monolayer is achieved. These cells are exposed to pneumococci to test their ability to attach to, enter into and penetrate this epithelial layer. To distinguish attachment versus internalization the epithelial cells are washed and incubated for 2 hrs with medium containing penicillin and gentamycin. The initial focus is on the TIGR4 strain, its nanA and nanB mutants, and the double mutant. Stable transparent and opaque variants of the TIGR4 strain have been generated by sequential passages until stable variants were obtained that did not reverse following in vivo challenge. These TIGR4 variants are compared for their ability to adhere to, enter and tranverse epithelial cells. Wells are loaded with $10^3$-$10^6$ CFU/well in EMEM media. At 0.5, 1, 2, 4, 8, and 24 hrs cultures are harvested both above and below the epithelial layer and analyzed for CFU. The cell layers are washed 5-6 times prior to overlaying the cells with Todd-Hewitt broth supplemented with 0.5% yeast extract and 0.5% agar cooled to 41° C. to determine the pneumococcal CFUs associated with the monolayer. The plates are incubated overnight at 37° C. and 5% CO2 after which the CFU are counted. The cell lines are analyzed for expression of the PAF-R. Total RNA derived from these cell lines are analyzed by RT-PCR using the two primers, PAF-1 (5'-CCGATACACTCTCTTC-CCGA-3' (SEQ ID NO:3); nucleotides 151 to 170) and PAF-2 (5'-ACAGTTGGTGCTAAGGAGGC-3' (SEQ ID NO:4); nucleotides 970 to 951) resulting in a 838 bp PCR product (Stengel et al., (1997) Arterioscler. Thromb. Vasc. Biol. 17: 954-962, which is incorporated herein in its entirety for the methods taught therein). If the PAF receptor is present PAF receptor inhibitors such as octylonium bromide (Biomol Research Laboratories, Inc. Plymouth meeting, PA) or PAF (Biomol) are added to the cultures to determine the contribution of the PAF-R on epithelial adhesion and penetration. The octylonium bromide binds with high affinity to the PAF-R. Alternatively the above mentioned COS7 cells are used for this purpose and compare pneumococcal adherence in the presence and absence of PAF-R.

The degree of invasiveness of the different pneumococcal strains is correlated with production of inflammatory cytokines in both the apical and basolateral compartment of the Transwell system. The culture supernatants are collected at the various timepoints in both the upper and lower compartment and analyzed by ELISA (BD PharMingen) to determine the concentration of the inflammatory cytokines IL-1β, IL-6, IL-8, IL-10 and TNF-α. The epithelial monolayers are fixed in acetic alcohol and analyzed for the intracellular presence of pneumococci using PspA-specific immunofluorescent staining as previously used for visualization of pneumococci in OBs. Fluorescent images are visualized with a Leica/Leitz DMRB microscope equipped with appropriate filter cubes (Chromtechnology, Battleboro, Vt.) as previously described (Martin et al., (1998) J. Immunol. 160: 3748-3758, which is incorporated herein by reference for the methods taught therein). Images are collected with a C5810 digital color camera (Mamamatsu Photonic System) and processed with Adobe photoshop and IP LAB Spectrum software.

Results

Colonization of NanA and NanB Mutants.

Figure 5:
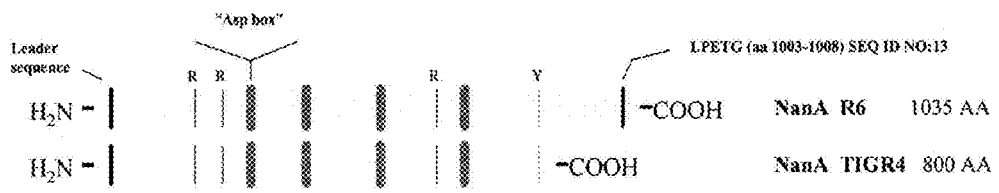
FIG. 5 shows a comparison in the motifs for secreted NanA, TIGR4, and for a R6 (type 2), which has the LPXTG (SEQ ID NO:14) motif for attachment to the cell wall. The TIGR4 gene includes a stop-codon prior to the sequence encoding the LPETG (SEQ ID NO:13) motif. Without this motif, NanA is secreted into the environment by TIGR4.

The effects of NanA mutations on the ability of *S. pneumoniae* to colonize the nasopharynx of CBA/N mice was assessed by comparing the numbers of pneumococcal cells isolated from nasal washes of mice that had been infected intranasally (i.n.) with those infected with NanA mutant-strains. Three different pneumococcal strains were included, thus, allowing for the effects of NanA mutations to be investigated on strains differing in capsular serotype and genetic background. TIGR4/NanA- (JW001), EF3030/NanA- (SAM001) and D39/NanA- (JCP001) are capsular type 4, 19F and 2, respectively (Table 4). In the case of the capsular type 4 clinical isolate, TIGR4, there is a stop-codon prior to the sequence encoding the LPETG (SEQ ID NO:13) motif. Without this motif, NanA is expected to be secreted into the environment by TIGR4. Examination of the other four pneumococcal-NanA sequences currently available, G54 (type19F), R6 (type 2), Spanish 23F and 670 (type 6B) (Berry et al. Gene 71:299-305; Hoskins et al. 2001 J. Bacteriol 183:5709-17; Tettelin et al. 2001 Science 293:498-506) indicated that they have the LPXTG (SEQ ID NO:14) motif for covalent attached to the cell wall (FIG. 5). Therefore, strains included here provided a comparison for mutations in strains where NanA is secreted and where it is surface bound.

Figure 6A:
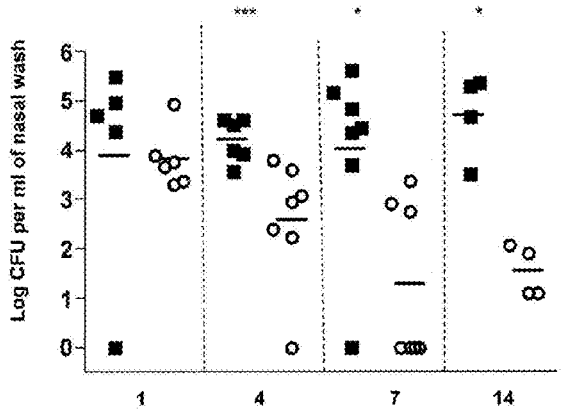
FIG. 6A shows the kinetics of viable pneumococci in the nasal wash of CBA/N mice infected i.n. with the *S. pneumoniae* parental strain TIGR4 (■) or the NanA isogenic mutant TIGR4/nanA- (○). Each point represents the total number of bacteria per ml of nasal wash fluid from each mouse. *$P<0.05$; $P<0.01$; *$P<0.005$ represent statistical significance compared with mice inoculated with TIGR4.
Figure 6B:
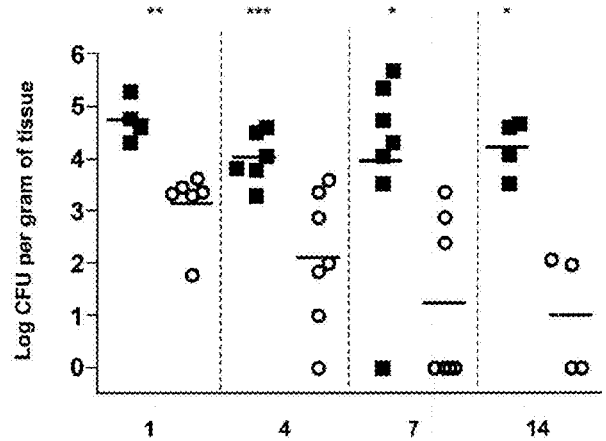
FIG. 6B shows nasal colonization kinetics in CBA/N mice infected i.n. with the *S. pneumoniae* parental strain TIGR4 (■) or the NanA isogenic mutant TIGR4/nanA- (○). Each point represents the total number of bacteria per gram of tissue from each mouse. *$P<0.05$; $P<0.01$; *$P<0.005$ represent statistical significance compared with mice inoculated with TIGR4.
Figure 6C:
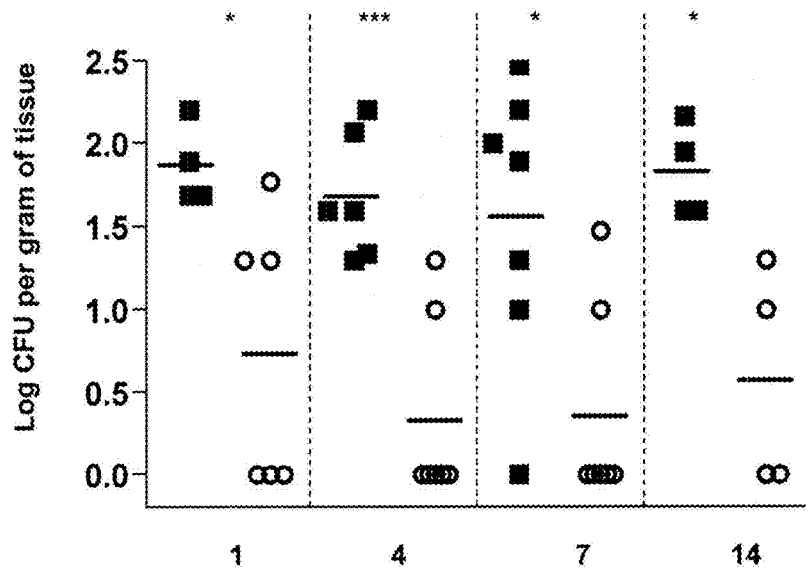
FIG. 6C shows the kinetics of CFU in the olfactory bulb of CBA/N mice infected i.n. with the *S. pneumoniae* parental strain TIGR4 (■) or TIGR4/nanA- (○). Each point represents the total number of bacteria per gram of tissue from each mouse. *$P<0.05$; $P<0.01$; *$P<0.005$ indicate statistical significance compared with mice inoculated with TIGR4.
Figure 7A:
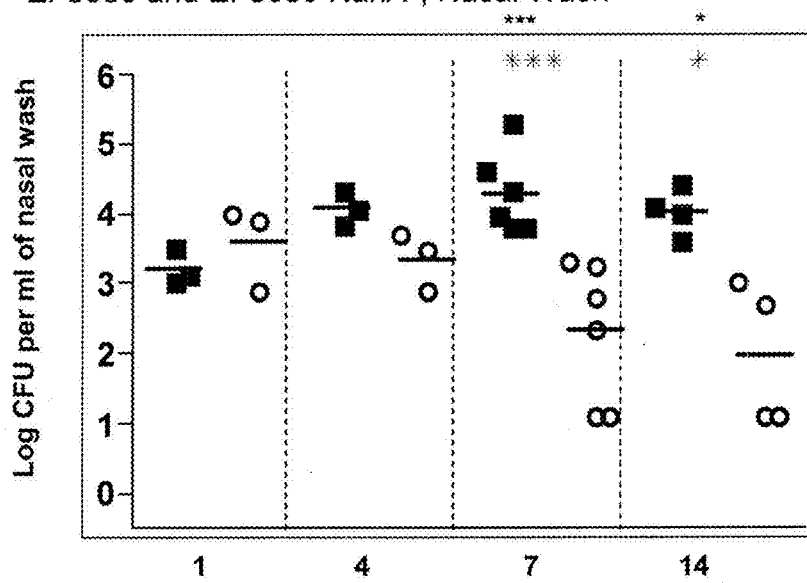
FIG. 7A shows nasal colonization kinetics in CBA/N mice infected i.n. with the *S. pneumoniae* parental strain EF3030 (■) or EF3030/nanA- (○). Each point represents the total number of bacteria per ml of nasal wash from each mouse. *$P<0.05$; $P<0.01$; * $P<0.005$ indicate statistical significance compared with mice inoculated with EF3030.
Figure 7B:
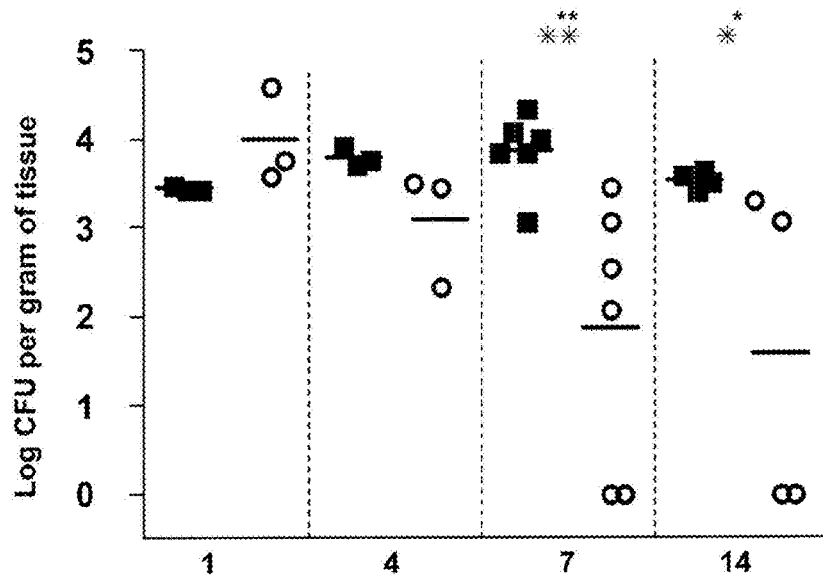
FIG. 7B shows nasal colonization kinetics in CBA/N mice infected i.n. with the *S. pneumoniae* parental strain EF3030 (■) or EF3030/nanA- (○). Each point represents the total number of bacteria per gram of tissue from each mouse. *$P<0.05$; $P<0.01$; *$P<0.005$ represent statistical significance compared with mice inoculated with EF3030.
Figure 7C:
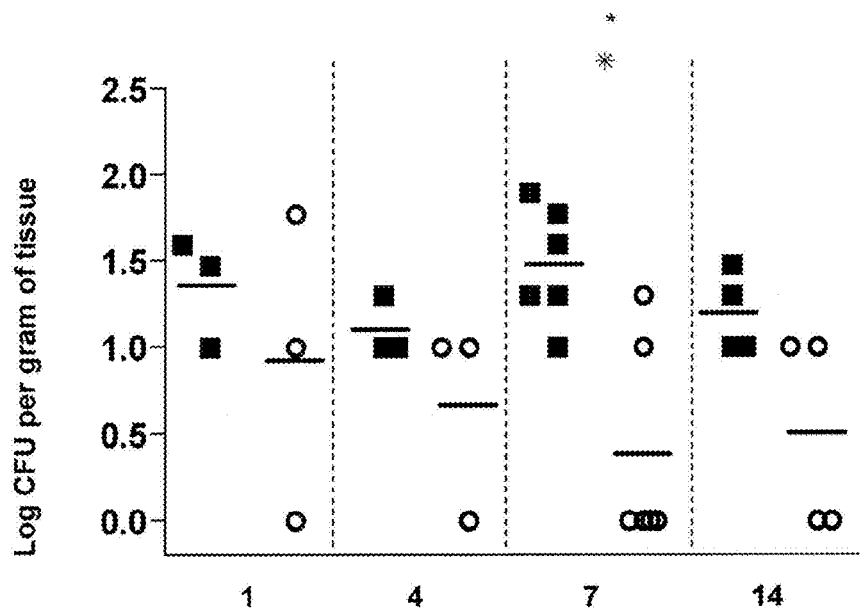
FIG. 7C shows nasal colonization kinetics in CBA/N mice infected i.n. with the *S. pneumoniae* parental strain EF3030 (■) or the NanA isogenic mutant EF3030/nanA- (○). Each point represents the total number of bacteria per gram of tissue from each mouse. * $P<0.05$; $P<0.01$; *$P<0.005$ represent statistical significance compared with mice inoculated with EF3030. When wild type and mutant data are pooled for all time points the comparison between EF3030 and EF3030 NanB- was statistically significant at $P=0.001$.

A dramatic decrease in colonization was observed in the NanA mutants of both TIGR4 and EF3030 (FIGS. 6 and 7).

Figure 8:
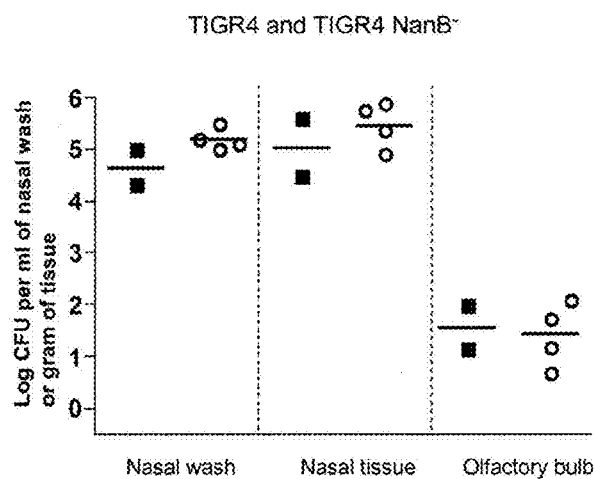
FIG. 8 shows nasal colonization kinetics in CBA/N mice infected i.n. with the *S. pneumoniae* parental strain TIGR4 (■) or TIGR4/nanB- (○) at 4 days post inoculation. Each point represents the total number of bacteria per ml of nasal wash or gram of tissue from each mouse. In no case was the difference between TIGR4 and TIGR4/nanB- statistically significant.
Figure 9:
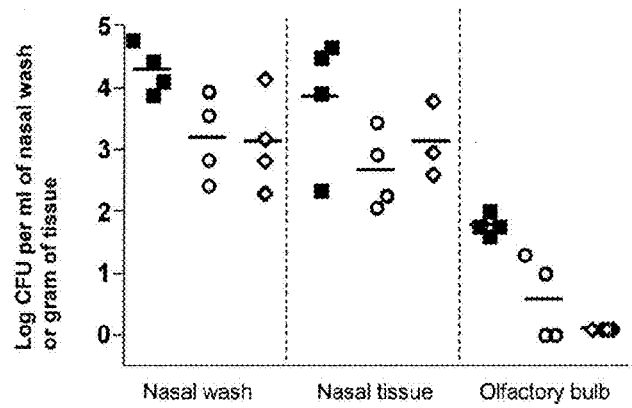
FIG. 9 shows nasal colonization kinetics in CBA/N mice infected i.n. with the *S. pneumoniae* parental strain TIGR4 (■) TIGR4/nanA- (○) or TIGR4/AB- at 4 days post inoculation. Each point represents the total number of bacteria per ml of nasal wash or gram of tissue from each mouse. In no case was the difference between TIGR4/nanA- and the double mutant TIGR4/nanAB- statistically significant.

*S. pneumoniae* expresses another neuraminidase, NanB. A similar degree of homology is shared between NanB relative to NanA. NanB shares 43% homology (24% identity) with NanA. Shared residues between the proteins have suggested that it is a sialidase (Berry et al. 1996 J. Bacteriol. 178:4854-4860). NanB has been found to have a pH optimum of 4.5 as compared to the pH optimum of NanA between 6.5 and 7. Even at its optimal pH, NanB is about 1/100th as active as a sialidase as is NanA at its pH optimum. Even so, to see if there is a requirement of NanB for colonization and direct invasion of the CNS, strains TIGR4/NanB- (JW002), a mutant was constructed in the TIGR4 genetic background deficient in NanB as well as strain TIGR4/NanAB- (JW003), which is deficient in both NanA and NanB expression. Infection of mice with JW002 resulted in a level of colonization nearly identical to the TIGR4 strain (FIG. 8). Moreover, no significant reduction in colonization occurred in the double mutant (JW003) relative to the NanA mutant (FIG. 9).

Entrance of Pneumococci into the CNS.

In order to track the movement of *S. pneumoniae* to the nasal tissue (including the olfactory nerves) the olfactory bulb and the remainder of the brain were tested for the presence of *S. pneumoniae*. NanA mutants, regardless of genetic background, were found in significantly reduced numbers relative to wild type strains in the nasal tissue and olfactory bulb. At the time of sacrifice, all mice were bled and none exhibited detectable pneumococci in the blood (<12 CFU/ml blood), indicating that pneumococci move directly into the CNS tissue from the nasal cavity. The NanB mutant had no effect on the entry of the pneumococci into the nasal tissue or the olfactory bulb (FIG. 8).

NanA mutants are clearly attenuated in their ability to colonize and persist in the nasopharynx and the CNS. This was observed in strains differing in both capsular serotype and attachment of NanA to the surface. Although NanA is but one of many surface structures that influence the intimacy between the bacterial cell surface and the host, its involvement is essential in nasal carriage as well as targeting of pneumococci to the CNS. Disruption of NanA significantly reduced colonization and targeting to the CNS. This result was observed in both TIGR4 and EF3030.

Strain EF3030 (type 19F) colonizes the nasopharynx with great efficiency for over a month. However, despite the ability of EF3030 to persist, mutations in NanA significantly reduced numbers of pneumococcal cells in the nose. Attenuation was even more dramatic in the TIGR4/NanA-strain where numbers of cells isolated from the nasal wash fell to close to the detectable limit after 14 days.

In the natural setting the pneumococcus co-exists with other bacterial species. Thus NanA's other functions may include altering the function of host proteins and contributing to the long term stability of carriage. NanA may also enhance pneumococci's ability to compete with other oral microbes including *N. meningitidis* and *H. influenzae* or by making host glycoproteins available as a carbon source.

Although the major result of these studies has been the demonstration that NanA expression was required for optimal carriage in mice, these data also demonstrated that pneumococci lacking NanA were found in much lower numbers in the olfactory bulbs. It is difficult at this point to know if an active NanA is important for survival of *S. pneumoniae* in CNS tissues. Although the numbers of NanA mutants recovered from these tissues are much less than the parental strain, their very presence in neuronal tissues argues an additional virulence effect of NanA once the pneumococci enter the brain. The decreased level of neuraminidase-mutants in the OB is very likely to be the result of diminished carriage. This finding underscores the principle that carriage is a prerequisite for more invasive diseases and that interventions capable of reducing carriage, such as immunization with NanA, will offer protection against *pneumoniae*, meningitis, otitis-media and sepsis.

Of the known sequences for nanA, the TIGR sequence is the only one that does not contain a surface anchor. In this strain, a frame shift results in truncation of the molecule prior to the LPETG (SEQ ID NO:13) motif (Tettelin et al. 2001 Science 293:498-506). For most strains a significant portion of the NanA is expected to be covalently attached to the cell wall by sortase (Mazmanian et al. 1999 Science 285:760-63) where it has been detected in electron micrographs (Camara et al. Infect. Immun. 62:3688-95). In these studies, TIGR4 as well as EF3030 exhibited NanA dependent carriage and presence in the olfactory bulbs. From studies of the localization of NanA activity in the supernatant or bacterial pellet, it was shown that, unlike TIGR4, the NanA activity of EF3030 is cell associated. Thus, NanA can facilitate colonization whether it is surface bound or whether it is secreted.

Example 3

The Role of Gangliosides in *S. pneumoniae* Pathogenesis

Purified neuraminidase, NanA (Calbiochem), is administered at 1, 10 and 50 µg in 10 µl PBS nasally 15, 30 and 60 minutes prior to isolating the ON/E. The tissues are fixed in 4% paraformaldehyde, and paraffin sections made. GM1 is stained for using biotinylated-CT-B followed by Streptavidin-FITC and the intensity of staining is analyzed. The section is also stained by asialo-GM1-specific Abs conjugated to rodamine to confirm a decrease of GM1 staining coincident with increase of asialo-GM1 staining in these tissues. Parallel groups of mice undergoing the same treatment are analyzed for colonization by *S. pneumoniae* strain TIGR4 and EF3030 at days 1 and 4, to assure that neuraminidase treatment resulted in elevated levels of nasal colonization. Mice are given a high dose of strain EF3030 ($1\times10^8$ CFU) nasally and the ON/E is isolated at the following intervals: 1, 3, 6, and 12 hrs, 1 and 4 days after nasal challenge. The ON/E is stained as outlined above and analyzed for GM1 and asialo-GM1 expression. If decreased GM1 and elevated asialo-GM1 expression are observed in the nasal tissues, then the NanA- and NanB-deficient strains are also tested since they would be expected not to alter GM1 expression in the nasal tract. The removal of sialic acid residues exposes the subterminal dissaccharide, β-D-galactopyranosyl-(1-3)N-acetyl-D-galactosamine, which represents an immunodominant group of the Thompson-Friedenreich antigen, for which PNA has high affinity. Thus, changes in the PNA-binding sites in the ON/E is another measure of neuraminidase activity. Frozen sections made from these tissues are readily stained with PNA-FITC or PNA-HRP (Medac, Hamburg, Germany) to determine if an increase in PNA-binding sites occurs based on microscopy (Black et al., (2000) Pediatr. Infect. Dis J. 19: 187-195; Klein et al. (1978) Klin. Wochenschr. 56: 761-765, which are incorporated herein by reference in their entirety for the methods taught therein).

The GM1 site is specifically blocked prior to nasal administration of strain TIGR4 or EF3030. This is approached in three ways by using: 1) CT-B versus a non-ganglioside control protein e.g. ovalbumin, 2) Abs to GM1 (Calbiochem) versus normal rabbit immunoglobulins, or 3) GM1-specific peptides synthesized in the UAB Protein Analysis and Peptide Synthesis Core Facility. The inhibition with the GM1-specific peptide is the best approach since CT-B and possibly Abs to GM1 is expected to cause concomitant inflammation. In these experiments the ON/E and OBs are analyzed 1 and 4 days after application for pneumococcal CFU. An alternative approach of blocking GM1 is the use of a GM1-binding peptide that was discovered by use of a phage-display pentadecapeptide library selecting for GM1-binding peptides. This GM1-binding peptide VWRLLAPPFSNRLLP (SEQ ID NO:5) has high affinity ($10^{10}$ M$^{-1}$) for GM1 and an IC$_{50}$ of 1.0 µM. Matsubura et al., (1999) FEBS Letters 456: 253-256. A peptide of the same length and composed of the same amino acids in a randomly selected sequence is used as control. The GM1-binding ability of both peptides is confirmed by ELISA prior to use in vivo. Initially, 100 µg of these two peptides is administered nasally in 10 µl Ringer's solution or PBS, 10 minutes prior to applying $3\times10^6$ CFU of strain EF3030. The ON/E is analyzed for CFU on days 1 and 4 after application for numbers of CFU relative to untreated CBA/N mice.

Blocking experiments are performed with PAF (Biomol Research Laboratories, Inc. Plymouth meeting, PA) and the PAF-R antagonist octylonium bromide (Biomol). This compound binds with high affinity to the PAF-R. Each ganglioside is tested individually. Besides mixed gangliosides, asialo-GM1, GM1, GD1a, GD1b, GT1 (Calbiochem) and the GM3 (Sigma) are tested for their ability to inhibit nasal colonization as assessed on day 1 and 4 after challenge. Various gangliosides are able to block this process. The GM3 ganglioside functions as a negative control since it lacks the published C-polysaccharide binding motif. Based on the data presented on colonization with EF3030 following ganglioside preincubation, mixed gangliosides are more effective than asialo-GM1 at blocking colonization. This indicates that other gangliosides besides asialo-GM1 are involved in the process of pneumococcal colonization of the nasal tract, lungs and brain. These ganglioside inhibition studies focus on the TIGR4 strain and its neuraminidase mutants. Short term in vitro incubation with the TIGR4 strain on ganglioside-coated ELISA plates demonstrated attachment of the TIGR4 strain to the asialo-GM1. Enterotoxins provide another means of differentially blocking pneumococci-ganglioside interactions in the nasal tract. Both CT and LTh-1 are both serogroup I heat-labile enterotoxins (Pickett et al., (1986) J. Bacteriol 165: 348-352) and display similar, although slightly different, ganglioside binding specificities. Fukuta et al., (1988) Infect Immun. 56: 1748-1753. CT (List Biological Laboratories, Inc., Campbell, Calif.) binds to GM1 and to a lesser extent to GD1b. LTh-1 displays preferential binding to GM1 and GD1b and binds weakly to GM2 and asialo-GM1. Fukuta et al., (1988) Infect Immun. 56: 1748-1753. If GM1 is the main ganglioside interacting with *S. pneumoniae*, the use of LTh-1 would not only block the GM1 ganglioside but might also block asialo-GM1, which could represent a natural low frequency binding site not requiring neuraminidase activity. The heat-labile enterotoxins from serogroup II display different ganglioside binding specificities, in particular the heat-labile enterotoxin LT-IIb. This toxin binds to GD1a and to a lesser extent to GT1b and showed no affinity for GM1. Fukuta et al., (1988) Infect Immun. 56: 1748-1753. The LT-IIa binds with high affinity to GD1b and with a lower affinity to GM1, GT1b, GQ1b, GD2, GD1a, and GM2. Fukuta et al., (1988) Infect Immun. 56: 1748-1753. The LT-II toxins have been kindly provided by Dr. T. D. Connell. To optimize the nasal dose and the optimal time period to observe inhibition of pneumococcal attachment to ON/E, a dose response study (1.0 or 10 μg) is initially performed on a selected enterotoxin, which is given during nasal application of S. pneumoniae. If inhibition of nasal colonization is observed on day 4 the observations are extended to day 11 during which enterotoxin is given every other day. The CFU in ON/E and OBs of CBA/N mice are measured.

Example 4

The Role of C-Polysaccharide-Specific Antibodies in Pneumococcal Colonization

Pneumococcal C-polysaccharide, also known as teichoic acid, is structurally identical to the pneumococcal F-antigen, also known as lipoteichoic acid. Fischer et al. (1993) Eur. J. Biochem 215: 851-857. This is a unique feature of S. pneumoniae among gram-positive bacteria. The immunodominant determinants on these molecules are the phosphorylcholine (PC) residues and Abs to PC are protective against i.p. or nasal pneumococcal challenge. Briles et al., (1984) Eur. J. Immunol. 14: 1027-1030; Briles et al., (1981) Nature 294: 88-90; Yother et al., (1982) Infect. Immun. 36: 184-188; Briles et al., (1984) J. Mol. Cell. Immunol. 1:305-309. Thus, the role of PC-specific Abs, either obtained by passive transfer or active nasal immunization, is explored. For passive transfer of protective PC-specific Abs, i.e., T15 idiotypic monoclonal Abs (mAbs) of both the IgG3 (59.6C5) and IgM (22.1A4) isotypes are used. Briles et al., (1981) Nature 294: 88-90. The T15 idiotype has been shown to be more protective than the M603 or 511 idiotypes against pneumococcal infection in mice (Briles et al., (1984) Eur. J. Immunol. 14: 1027-1030), presumably by more efficiently binding the C-polysaccharide. Passive Ab transfer involves the direct application of T15 Abs (100 μg) with nasally applied pneumococci and is compared to i.v. or i.p. administered Abs for reducing nasal colonization. Colonization is monitored over time (day 4, 11, 18) and, if no significant difference is observed between the different groups in these experiments, mAbs (20 μg) are applied nasally every other day. CBA/N mice do not produce T15 idiotypic anti-PC Abs. Passive transfer of anti-PC-specific Abs is not expected to induce mucosal IgA or other isotypes of PC-specific Abs in the nasal tract. In order to induce nasal Abs, two different approaches are taken. One is the direct nasal application of the protease treated R36A strain, which is known to induce Ab responses to C-polysaccharide. Although protective immunity of anti-PC Abs has been studied, no data is available on their role at mucosal surfaces such as the nasal tract. The CBA/N mice X-chromosome-linked immunodeficiency results in an inability to generate anti-PC Abs of the T15-idiotype. To determine the importance of this inability CBA/N mice are compared to their wildtype counterpart the CBA/J mice (Jackson Laboratories, Bar Harbor, Me.). Immunization with strain R36A for induction of anti-PC Abs involves proteolytic removal of surface protein (Krause (1970) Adv. Immunol. 12: 1-56). The alternative approach for nasal immunization is coupling of PC to the protein keyhole limpet hemocyanin (KLH) as previously described (Krause (1970) Adv. Immunol 12: 1-56; Chesebro and Metzger (1972) Biochemistry 11: 766-771, which are incorporated herein by reference for the methods taught therein). Nasal immunization with PC-KLH is performed with the mucosal adjuvant CT to optimize mucosal immune responses. The mice are challenged 2-3 weeks after the last immunization to prevent effects of CT on colonization. Three nasal immunizations are performed at one week intervals. The serum Ab titers are monitored using a C-polysaccharide and PC-specific ELISA as routinely performed by those skilled in the art. For the PC-specific ELISA, PC is coupled to BSA as described previously (Chesebro and Metzger (1972) Biochemistry 11: 766-771, which is incorporated herein by reference for the methods taught therein). In addition to serum, the Ab titers in nasal washes, saliva, and bronchial lavages are measured. These analyses include IgA, IgM, IgG, and IgG-subclass distribution in both mucosal secretions and serum. The protocol that induces the most optimal mucosal Ab titers is used to perform mucosal challenge studies with the TIGR4 strain, which is administered nasally at ~5×10$^6$ CFU to mice after which colonization is monitored on day 4 and 11. In the immunization studies, normal and fully immunocompetent mice (CBA/J strain) were compared to CBA/N mice, as in previous studies. Wallick et al., (1983) J. Immunol. 130: 2871-2875.

Example 5

The Role of Neuraminidase-Specific Immunity in S. pneumoniae Pathogenesis

To nasally immunize the mice prior to nasal challenge commercially available S. pneumoniae-derived neuraminidase was used (Calbiochem, Darmstadt, Germany). However, the nanA gene was cloned and expressed in E. coli using a histidine-tag containing expression vector (Invitrogen, Carlsbad, Calif.) in order to obtain sufficient amounts of protein for the proposed studies. Nasal immunization of 3.4% formaldehyde-treated neuraminidase is compared versus-untreated neuraminidase in the presence or absence of CT in order to optimize the mucosal immune responses. These immunizations are performed in both CBA/N and CBA/J mice. Three nasal immunizations are given one week apart during which serum and saliva Abs titers are monitored by ELISA. The immune mice are challenged with the TIGR4 strain and the colonization of ON/E, OB, brain, blood, spleen, and lungs is compared on days 4 and 11. To block host interaction, both neuraminidase and C-polysaccharide-specific Abs are induced simultaneously. A combined regimen of nasal immunization with neuraminidase and passive immune protection by transfer of T15 idiotypic mAbs is used.

Example 6

The Efficacy of Neuraminidase-PC Conjugate to Protect Against Nasal Challenge with S. pneumoniae Mice are immunized with neuraminidase and PC-KLH in combination with CT as nasal adjuvant to assess enhancement of protection and decrease nasal colonization by the EF3030 and TIGR4 strains on day 11 compared to each antigen used alone. In addition, Ab titers in nasal washes, saliva, and serum are analyzed as indicated above to correlate immune parameters with degree of protection to pneumococci in the nasal tract. To generate a more optimal immune response phosphocholine is directly coupled to neuraminidase. This construct is tested for immunogenicity when delivered with or without CT as adjuvant after nasal and systemic immunization in both CBA/N and CBA/J mice. The Ab titers in nasal washes, saliva, and plasma are measured by ELISA.

Challenge studies are performed with 10⁷ CFU of strains EF3030 or 10⁶ TIGR4. The mice are sacrificed on day 11 after challenge and analyzed for CFUs observed in blood, nasal washes, ON/E, OB, and brain. Immunization with neuraminidase coupled to PC enhances protection by increasing mucosal and systemic Ab levels to these two virulence components. The antigen-specific IgG subclass distribution are altered by using other mucosal adjuvants. CT generates a Th2-, LT a mixed Th2/Th1-, and CpG motifs such as the DNA oligonucleotide (ODN) 1826 a Th1-type response with associated changes in IgG subclass distribution.

Different adjuvants further enhance the ability of neuraminidase-C-polysaccharide-specific immunity to protect against nasal colonization by *S. pneumoniae* and lead to the formulation of new pneumococcal vaccine approaches.

Example 7

Figure 10:
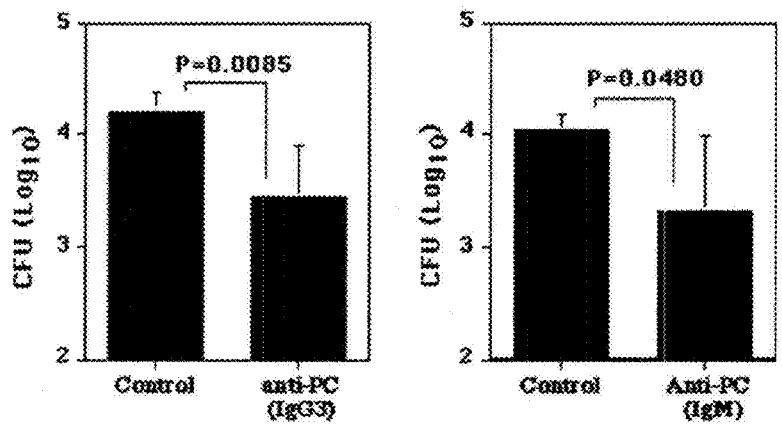
FIG. 10 shows inhibition of nasal colonization of *S. pneumoniae* by anti-phosphocholine-specific monoclonal antibodies after nasal challenge. Inhibition of nasal colonization of *S. pneumoniae* by anti-PC-specific mAbs after nasal challenge. A total of $1\times10^6$ CFU of the TIGR4 strain were incubated with 5 µg of anti-PC mAbs of either the IgG3 subclass or IgM isotype. A total of 5 µl was administered per nare. Indicated are the CFU in 500 µl nasal wash respectively 9 and 12 hours after application. Indicated are the mean±SD of five mice per group.

Inhibition of Nasal Colonization of *S. Pneumoniae* by Anti-Phosphocholine-Specific Monoclonal Antibodies after Nasal Challenge A total of $1 \times 10^6$ CFU of the TIGR4 strain were incubated with 5 µg of anti-phosphocholine monoclonal antibodies of either the IgG3 subclass or IgM isotype. A total of 5 µl was administered per nare. Indicated are the CFUs in 500 ml nasal wash respectively 9 and 12 hours after application. A significant over 80% decrease was observed for both monoclonal antibodies. Indicated are the mean±SD of five mice per group. The data are shown in FIG. 10.

Example 8

Neuronal Damage and Inflammation after Nasal *S. Pneumoniae* Application

The ON/E, OB, and brain are isolated from treated mice at days 1, 3, 7, and 14 after nasal application of *S. pneumoniae* strain EF3030 and analyzed histologically for inflammatory responses. The D39 or TIGR4 strains are compared to their nanA mutant strains for their ability to generate inflammatory responses. At sacrifice, the mice are perfused with PBS at 25° C., followed by perfusion with 10 ml of Zamboni's fixative (4% paraformaldehyde, 15% picric acid in 0.1 M phosphate buffer. The OB and ON/E are removed and then placed in fresh 4% paraformaldehyde (PFA) at 4° C. overnight. The tissue is then transferred to a 30% sucrose solution at 4° C. for 48 hr to cryoprotect it prior to sectioning. The tissues are then frozen in OCT and sections (6 µm) are placed on previously coated microscope slides (10% BSA in saline). Initially, hematoxylin and eosin (H&E) staining are performed to detect any inflammatory cell infiltrates in the OB, trigeminal ganglia and ON/E during this time period. In order to assess neuronal damage, nerve growth factor β1 (NGF-β1) is stained for. NGF-β1 is produced after neuronal damage and functions to prevent apoptosis and to stimulate new growth of nerve cells. Trigeminal ganglia and OB sections are stained with a biotinylated rabbit anti-human NGF-β1 Ab at a concentration 0.2 µg/ml. The Ab-stained sections are incubated at 4° C. overnight. The slides are rinsed with PBS and then reacted with avidin-biotin-complex (ABC) Vectastain (Vector Laboratories, Burlingame, Calif.) for 30 min at 25° C. The tissue is rinsed 3 times with PBS and then reacted with diaminobenzidene (DAB) for 5-10 min as previously reported. The slides are rinsed 3 more times and sections counterstained with C. S. hematoxylin for 30 sec. After washing in $H_2O$, the slides are dehydrated in 100% alcohol and xylene. An increase in NGF-β1 provides an indication of the degree of damage in neuronal tissues. Another indicator for neuronal involvement is the activation of microglia. Activated microglia display an amoeboid, spherical shape while resting cells (in $G_o/G_1$) have an arborized, ramified appearance. This change upon activation allows one to distinguish resting and activated microglia. For microglia, F4/80 antibody or anti-MAC-1 (MI/70) are used to address the activation state after *S. pneumoniae* challenge. In addition to neuronal damage and microglia activation, the induction of apoptosis in OB is assessed. To this end, the induction of active Caspase 3, an Asp-Glu-Val-Asp specific protease, is analyzed because it is important in the initiation of apoptotic pathways. An Ab specific for active Caspase 3 (Cell Signaling Technology, Inc., Beverly, Mass.) can be used in immunohistochemistry for detection of apoptosis. If Caspase 3 activity is detected in neuronal tissues by immunohistochemistry, activity is quantified using a Caspase-3 Assay kit (Molecular probes, Eugene, Oreg.) based on a fluorescent signal induced after proteolysis of the substrate.

Example 9

Ability of *S. Pneumoniae* to Target Olfactory Bulbs by Retrograde Axonal Transport First, accumulation of pneumococci in the neuronal tissues, OB and brain, of treated mice following nasal and i.v. inoculation is assessed. Following i.v. inoculation, any pneumococci in the neuronal tissues has entered through the blood. Tissues at 1, 4, 11 and 18 days following nasal challenge are collected. In that case the numbers of bacteria per gram of brain and OB should be similar at all time points post injection. In contrast, for bacteria entering through the nasal tract following intranasal inoculation, an accumulation in the OB (expressed per weight of tissue) precedes and in general remains ahead the accumulation observed in the brain.

Second, in vivo imaging of pneumococci after nasal application is performed. Technetium-99 (Tc-99m)-labeled TIGR4, stable opaque and transparent variants, EF3030, and TIGR4 mutants lacking nanA and/or nanB are used to visualize their presence in mice using gamma camera imaging as previously performed with adenovirus using a strategy originally described by Waibel et al. (1999) Nature Biotechnol. 17:897-901. This allows imaging for approximately the first 24 hrs following nasal application due to the short half live (6 hrs) of this isotope and allows analysis of the early events taking place in the nasal tract. For long term imaging of the pneumococci, a luciferase- or GFP-expressing pneumococcal EF3030 (or TIGR4) strain are used to visualize the bioluminescence in vivo. A luciferase-expressing pneumococci strain EF3030, commercially available from the Xenogen corporation (Alameda, Calif.), is used. Successful in vivo imaging with this pneumococcal strain has been previously reported. The mice are imaged using a bioluminescence imaging system (IVIS system, Xenogen, Inc.) to detect luciferase expression. Images are collected on mice oriented in the same position and always at 10 min after i.p. injection of 2.5 mg luciferin. During imaging the mice are maintained under enflurane anesthesia at 37° C. Imaging is performed several times on each mouse, beginning at 2 days to 18 days after nasal challenge with luciferase-expressing pneumococci. Image acquisition times for imaging are in the range of 20 sec to 10 min. Data acquisition software insures that no pixels are saturated during image collection. Light emission from the regions of interest (relative photons/sec) are quantitated using software provided by Xenogen. The intensity of light emission is represented with a pseudocolor scaling of the bioluminescent images. The bioluminescent images are typically over-layed on black and white photographs of the mice that are collected at the same time. This in vivo imaging focuses on analyzing the ability of pneumococci to enter the OBs from the nasal tract. This bioluminescence studies extend to the nanA TIGR4 mutant after successful transfer of the luciferase gene.

Example 10

In vivo Protection Following Immunization with NanA Fragments

Three NanA fragments were constructed. The fragments constructed were NanA571 SEQ ID NO:19, NanA215 SEQ ID NO:21, and NanA186 SEQ ID NO:23. The relative position of these fragments within the NanA sequences of SEQ ID NO:30 is shown in Table 5.

TABLE 5

The relative positions of the fragments within the TIGR4 coding region.

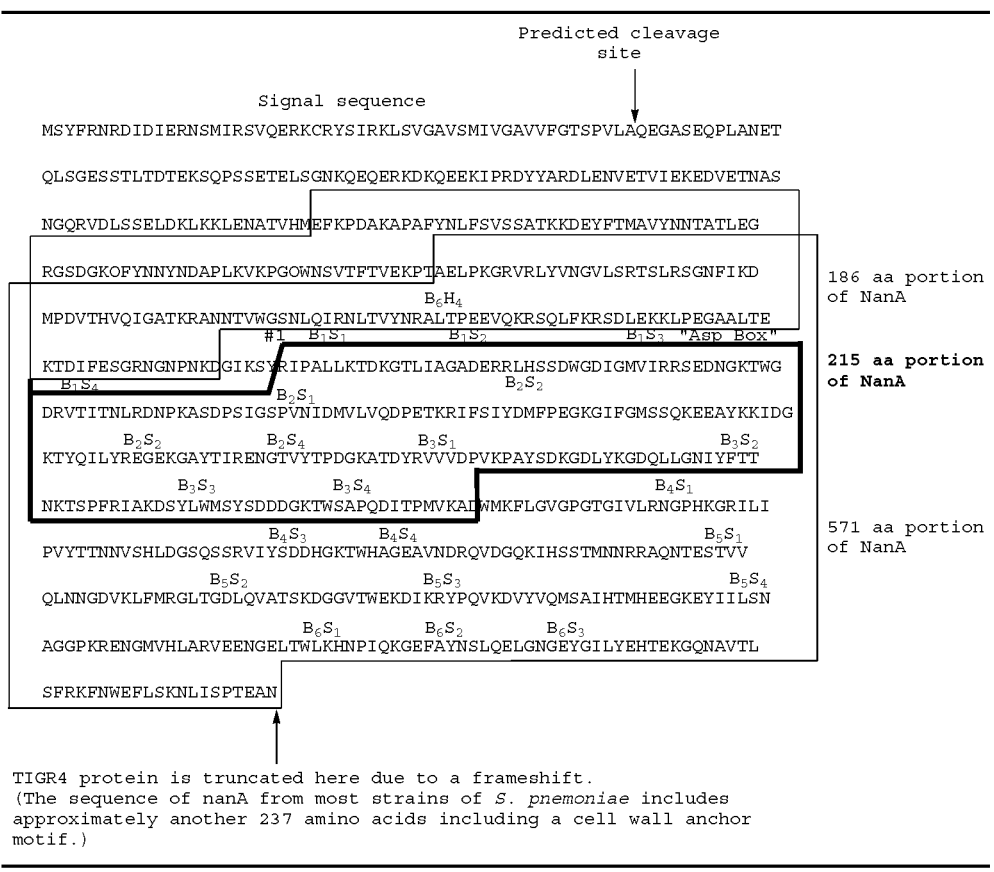

Figure 11:
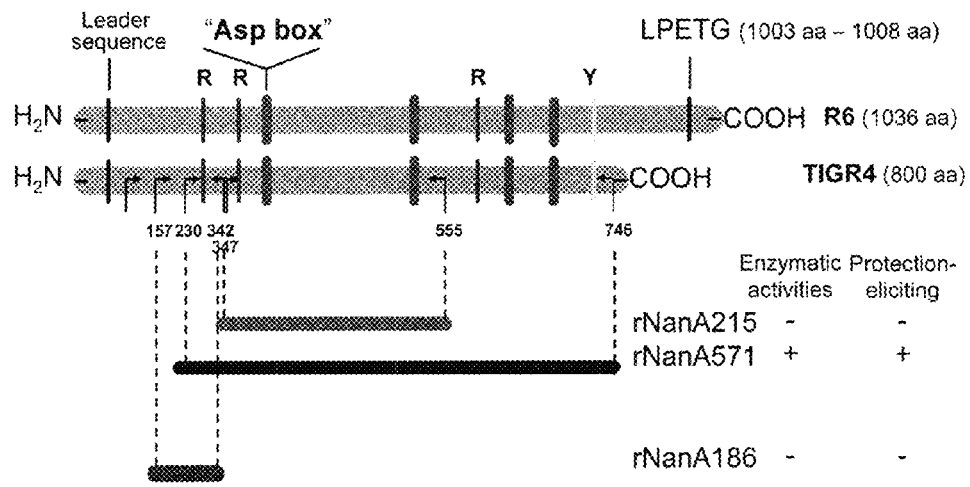
FIG. 11 shows alignment of R6 NanA and TIGR4 NanA and of fragments of TIGR4 NanA. rNanA571 elicited in vivo protection to *S. pneumoniae* challenge.

FIG. 11 shows alignment of the fragments relative to R6 NanA and TIGR4 NanA. NanA571 is a recombinant protein named for its number of amino acids. This recombinant protein contains a large central segment of NanA from TIGR4, corresponding to amino acids #230-#800 of R6 NanA, see Table 1 (counting from the start of the signal peptide) or #173-747 of the mature protein. It has the same truncated C-terminus that is present in TIGR4 strain. The central portion covers all 4 "Asp" boxes and also includes the tyrosine and the glutamate that are part of active site residues. The recombinant protein is active for sialidase activity. The molecular weight of NanA571 calculated with leader is about 66,735 daltons pI 8.88. The molecular weight of the streptococcal portion only is about 63,986 daltons pI 8.87.

The sequence of the NanA571 recombinant protein is as follows:

SEQ ID NO: 18
MGHHHHHHHHHHSSGHIEGRHMPTAELPKGRVRLYVNGVLSRTSLRSGN

FIKDMPDVTHVQIGATKRANNTVWGSNLQIRNLTVYNRALTPEEVQKRS

QLFKRSDLEKKLPEGAALTEKTDIFESGRNGNPNKDGIKSYRIPALLKT

DKGTLIAGADERRLHSSDWGDIGMVIRRSEDNGKTWGDRVTITNLRDNP

KASDPSIGSPVNIDMVLVQDPETKRIFSIYDMFPEGKGIFGMSSQKEEA

YKKIDGKTYQILYREGEKGAYTIRENGTVYTPDGKATDYRVVVDPVKPA

YSDKGDLYKGDQLLGNIYFTTNKTSPFRIAKDSYLWMSYSDDDGKTWSA

-continued

PQDITPMVKADWMKFLGVGPGTGIVLRNGPHKGRILIPVYTTNNVSHLD

GSQSSRVIYSDDHGKTWHAGEAVNDNRQVDGQKIHSSTMNNRRAQNTES

TVVQLNNGDVKLFMRGLTGDLQVATSKDGGVTWEKDIKRYPQVKDVYVQ

MSAIHTMHEGKEYIILSNAGGPKRENGMVHLARVEENGELTWLKHNPIQ

KGEFAYNSLQELGNGEYGILYEHTEKGQNAYTLSFRKFNWEFLSKNLIS

PTEAN

The italicized amino acids are derived from the cloning vector.

To construct the vector, an internal gene fragment of the SP1693_TIGR4 gene encoding NanA, was amplified by polymerase chain reaction from the *Streptococcus pneumoniae* strain TIGR4 using the oligonucleotides

```
                                        SEQ ID NO: 24
5'-GGAATTCCATATGCCGACAGCAGAACTACCTAAAGGC-3'
Forward (N2N_1844_Nde1)
and SEQ ID NO: 25
5'-CGCGGATCCTCATACTGGGTTAGGAAAGTCGCT-3'
(N2N402_BamH1).
```

Reactions were carried out for 30 cycles in a total volume of 50 µl in a cocktail containing 3.0 mM MgCl2, 125 µM dNTPs, 50 picomole of each primer, and 2.5 units of Taq DNA Polymerase. The cycle was 94° C., 1 min.; 55° C., 1 min; 72° C., 5 minutes. This ~1725 bp amplified gene fragment was cloned into Topo 4 vector using the T-tailed version. Positive clones were identified by PCR, then sequenced, plasmid DNA was purified and then digested with NdeI and BamHI, and the ~~1845 bp nanA gene fragment was then incorporated between NdeI and BamHI sites of a vector. pET16b, was used (Novagen, Inc. Darmstadt, Germany), which has a strong T7 promoter and translation signals. In this vector, there is an N-terminal His-tag and a factor Xa cloning site. DNA sequencing confirmed that the recombinant plasmid pNanA571 contained the expected gene fragment inserted in vector pET16b.

pNanA571 was transformed into the *E. coli* strain Rosetta Blue (pLysS) (DE3) for protein production. The expression strain contains a chromosomal copy of the T7 promoter under control of the inducible UV5 promoter. It also contains extra tRNAs for infrequent codons and the pLysS (T7 lysozyme) for easier lysis. Upon induction with IPTG, a truncated protein containing amino acids #230 to #800 of the wild type NanA protein was expressed. The six histidine residues present on the N-terminus of the recombinant protein simplified its purification by nickel chromatography. If desired, they can be removed with factor Xa cleavage.

pNanA215 was cloned and NanA215 was purified. The protein is called NanA215. This recombinant protein contains a near-N-terminal segment of NanA from the strain TIGR4 (SP1693), which includes amino acid residues 347-561 (numbers include SP). This corresponds to 294-508 of the mature protein. The included region covers 2 of the 4 "Asp" boxes, but does not include the actual active site residues. The recombinant protein made has no sialidase activity. The rNanA protein includes 215 amino acids from NanA and others from the vector as shown below. The molecular weight calculated with leader was 27,062 daltons pI 6.74. The molecular weight for the strep portion only was 24,152 daltons pI 5.87.

A NanA215 vector was constructed. An internal gene fragment of the nana_TIGR4 gene encoding NanA, was amplified by polymerase chain reaction from the *Streptococcus pneumoniae* strain TIGR4 using the oligonucleotides 5'-GGAATTCCATATGCGTATTCCA-3' SEQ ID NO:26 (JW1A_Nde1 Forward) and 5'-CGCGGATCCATCG-GCTTTGACCATCGGAG-3' SEQ ID NO:27 (JW1A_BamH1 Reverse). Reactions were carried out for 30 cycles in a total volume of 50 µl in a cocktail containing 3.0 mM MgCl2, 125 µM dNTPs, 50 picomole of each primer, and 2.5 units of Taq DNA Polymerase. The cycle was 94° C., 1 min.; 55° C., 1 min; 72° C., 5 minutes. This 645 bp amplified gene fragment was cloned into Topo 4 vector using the T-tailed version. Positive clones were identified by PCR and sequencing. Plasmid DNA was purified and then digested with NdeI and BamHI, and the ~645 bp nanA gene fragment was incorporated between NdeI and BamHI sites of a vector, pET16b (Novagen, Inc., Darmstadt, Germany).

The pET16b vector has a strong T7 promoter and translation signal. In this vector, there is an N-terminal His-tag and a factor Xa cloning site. DNA sequencing confirmed that the recombinant plasmid pNanA216 contained the expected gene fragment inserted in vector pET16b.

pNanA216 was transformed into the *E. coli* strain Rosetta Blue (pLysS) (DE3) for protein production. This strain contains a chromosomal copy of the T7 promoter under control of the inducible UV5 promoter. Upon induction with IPTG, a truncated protein containing approximately amino acids #347 through #561 of the wild type NanA protein was expressed. The six histidine residues present on the N-terminus of the recombinant protein simplified its purification by nickel chromatography. If desired, they can be removed with factor Xa cleavage.

The sequence of the NanA215 recombinant protein is as follows:

```
                                        SEQ ID NO: 20
MGHHHHHHHHHHSSGHIEGRHMRIPALLKTDKGTLIAGADERRLHSSDW

GDIGMVIRRSEDNGKTWGDRVTITNLRDNPKASDPSIGSPVNIDMVLVQ

DPETKRIFSIYDMFPEGKGIFGMSSQKEEAYKKIDGKTYQILYREGEKG

AYTIRENGTVYTPDGKATDYRVVVDPVKPAYSDKGDLYKGDQLLGNIYF

TTNKTSPFRIAKDSYLWMSYSDDDGKTWSAPQDITPMVKADPGC
```

The italicized amino acids are from the vector.

The NanA571 and NanA215 proteins were purified. To purify the proteins from the constructs pNanA571 and pNanA218 a Novagen (Darmstadt, Germany) system of binding buffers for the affinity nickel chromatography step was used. The protein was initially released in the following buffer: 20 mM Tris-HCl pH 7.9, 500 mM NaCl, 200 mM M imidazole. Screening by Coomassie Blue staining only showed primarily a single band for NanA571 that was estimated to have above 90% purity.

pNanA186 was constructed and NanA186 was purified. The protein was called NanA186. This recombinant protein contains a "near-N-terminal" segment of NanA from the strain TIGR4 (SP1693), which includes amino acid residues 157-342 (numbers include SP). The included region covers none of the 4 "Asp" boxes or active site residues. The recombinant protein made has no sialidase activity. The molecular weight calculated with leader was 23,580 daltons pI 9.49. The molecular weight for the strep portion only was 20,855 daltons pI 9.55.

The sequence of the NanA186 recombinant protein is as follows:

```
                                        SEQ ID NO: 22
MGHHHHHHHHHHSSGHIEGRHMEFKPDAKAPAFYNLFSVSSATKKDEYF

TMAVYNNTATLEGRGSDGKQFYNNYNDAPLKVKPGQWNSVTFTVEKPTA

ELPKGRVRLYVNGVLSRTSLRSGNFIKDMPDVTHVQIGATKRANNTVWG

SNLQIRNLTVYNRALTPEEVQKRSQLFKRSDLEKKLPEGAALTEKTDIF

ESGRNGNPNKDGSGC
```

Italicized amino acids are derived from the vector.

A vector for NanA186 was constructed. An internal gene fragment of the SP1693_TIGR4 gene1 encoding NanA, was amplified by polymerase chain reaction from the *Streptococcus pneumoniae* strain TIGR4 using the oligonucleotides 5'-GGAATTCCATATGGAGTTTAAGCCAGATG-3' SEQ ID NO:28 (nanA_sanofi_F) and 5'-CGCAGTGGATCCATCTTTATTTGGGTTACCGT-3' SEQ ID NO:29 (nanA_sanofi_R). Reactions were carried out for 30 cycles in a total volume of 50 µl in a cocktail containing 3.0 mM MgCl2, 125 µM dNTPs, 50 picomole of each primer, and 2.5 units of Taq DNA Polymerase. The cycle was 94° C., 1 min.; 55° C., 1 min; 72° C., 5 minutes. This 556 bp amplified gene fragment was cloned into Topo 4 vector using the T-tailed version. Positive clones were identified by PCR and were sequenced. Plasmid DNA was then purified and digested with NdeI and BamHI, and the ~556 bp nanA gene fragment was incorporated of the pET16b vector (Novagen, Inc., Darmstadt, Germany) The vector has a strong T7 promoter and translation signals. In this vector, there is an N-terminal His-tag and a factor Xa cloning site. DNA sequence confirmed that pNanA_186 contained the expected gene fragment.

pNanA186 was transformed into the *E. coli* strain Rosetta Blue (pLysS) (DE3) for protein production. This strain contains a chromosomal copy of the T7 promoter under control of the inducible UV5 promoter. Upon induction with IPTG, a truncated protein containing approximately amino acids #157 to #342 of the wild type NanA protein was expressed. The six histidine residues present on the N-terminus simplified purification by metal affinity chromatography. If desired, they can be removed with factor Xa cleavage.

Figure 12:
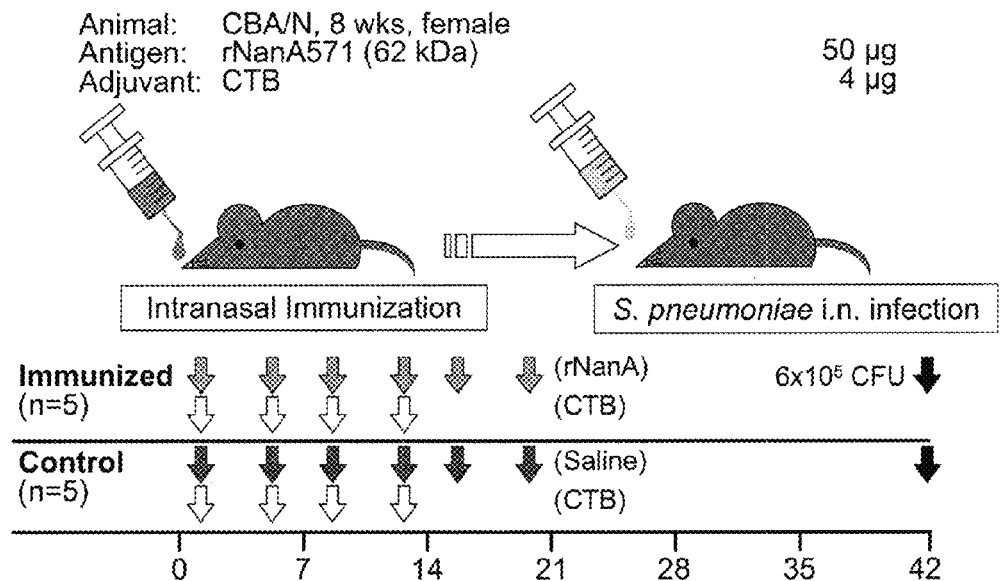
FIG. 12 is a schematic diagram showing an exemplary immunization protocol with rNanA571 and a control.

Purified proteins were used to immunize CBA/CAHN-XID (CBA/N) mice. Mice were immunized intranasally by instilling 10 µl containing 50 µg of recombinant neuraminidase A (NanA) into the single naris of a mouse in 10 µl twice a week (Monday and Thursday) for 3 weeks. During the first two weeks the inoculation included 4 micrograms of Cholera Toxin B subunit (Sigma, St. Louis, Mo.) as an adjuvant. The diluent for the immunization was lactated Ringers injection solution (Abbot Labs, Abbot Park, Ill.). This adjuvant was not administered during the last week of immunization to avoid non-specific stimulation of innate immunity. Control animals received the same 6 immunizations except with the CTB and lactated Ringers but without recombinant NanA. An exemplary immunization protocol is shown in FIG. 12.

Each experimental group of mice also received a Mock immunization which consisted of an irrelevant protein (cloned thioredoxin from the PET32A vector of Novagen, Darmstadt, Germany). In all isolations of proteins from *E. coli* there is a certain contamination with LPS. To control for any non-specific stimulation of the innate immune response by this LPS the amount of Mock protein was adjusted so that the preparation contained the same amount of LPS as was present in the immunogen. In all other respects this immunization was identical to that with the recombinant NanA fragments.

Three weeks after the last immunization (42 days after the start) the mice were challenged with 6×10$^5$ CFU of TIGR4 *Streptococcus pneumoniae*. This strain has been used previously in colonization studies. See Briles et al., Infect. Immunol. 73:6945-6951 (2005) and van Ginkel et al., Proc Natl Acad Sci USA 100:13263-13267 (2003). Seven days post colonization the mice were euthanized with an overdose of $CO_2$.

From each mouse a nasal wash, nasal tissue, all lung tissue, olfactory lobes, and the remaining brain were removed. A blood sample was also collected. These procedures have been described previously. See Briles et al., Infect. Immunol. 73:6945-6951 (2005) and van Ginkel et al., Proc Natl Acad Sci USA 100:13263-13267 (2003). The blood and nasal wash were serially diluted and plated on blood agar plates to detect pneumococci. The tissues were each homogenized, serially diluted and plated. Numbers of colony forming units were determined and the number of colony forming units in the total nasal wash, total nasal tissue, total lung samples, total olfactory lobes, and total brain were calculated based on the numbers of CFU counted and the dilutions plated.

In FIGS. 13-18, bacteremic mice calculated values are represented by solid black squares to differentiate them from colonized mice. In FIGS. 19-24 the bacteremic mice are indicated by a + and dead mice are indicated by an x. CFU determinations were not made for blood or tissues of dead mice. Rather a data point was plotted equal to or slightly above the highest data value for any mice in that group.

FIGS. 13-18 show the protection elicited by immunization with NanA571, mock immunogen and control. FIGS. 19-24 repeat the same data for NanA571 and its associated mock and control immunized mice. FIGS. 19-24 also include immunization data for NanA186 and NanA215. The mock and control immunization for all fragments is pooled in the data shown in FIGS. 19-24.

Figure 13:
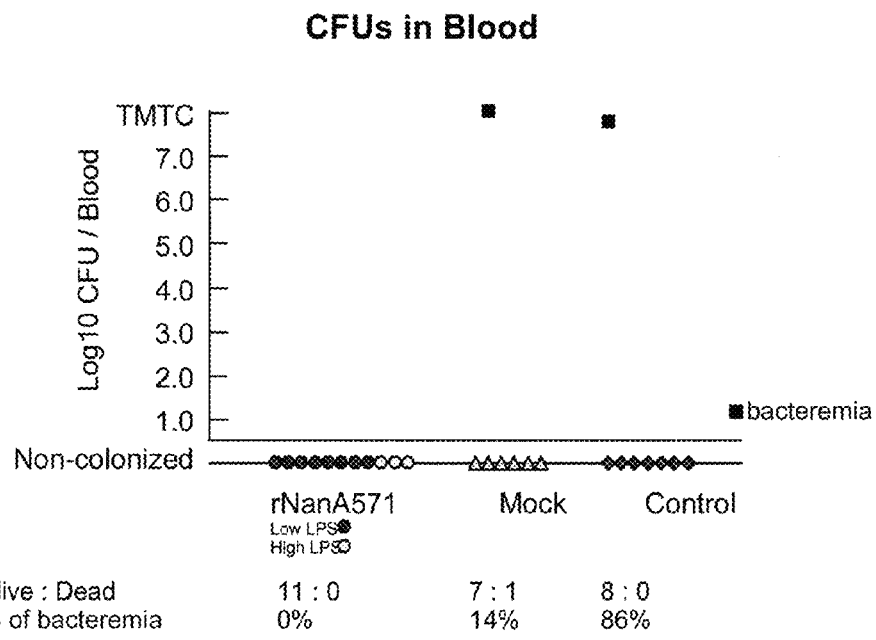
FIG. 13 shows the colony forming units (CFUs) of *S. pneumoniae* in the blood of animals immunized with rNanA571 versus mock and control animals. The black squares represent bacteremic animals. Mock animals received an irrelevant cloned protein whose concentration was adjusted so that mice received the same amount of LPS detected by the *limulus* lysates assay as was present in rNanA571. Control animals received the alum adjuvant but not rNanA571.
Figure 14:
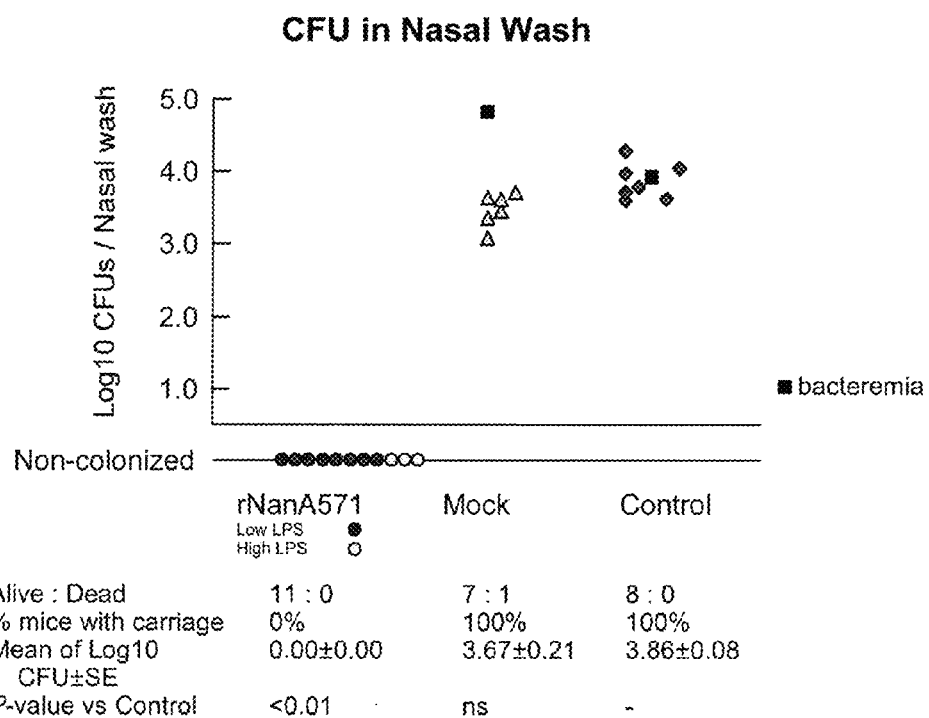
FIG. 14 shows the colony forming units (CFUs) of *S. pneumoniae* in the nasal wash of animals immunized with rNanA571 versus mock and control animals. The black squares represent bacteremic animals. The triangles represent animals given mock immunization protocol and having CFUs in their nasal wash. The diamonds represent animals given a control immunization protocol and having CFUs in their nasal wash. The circles represent animals immunized with rNanA571.
Figure 19:
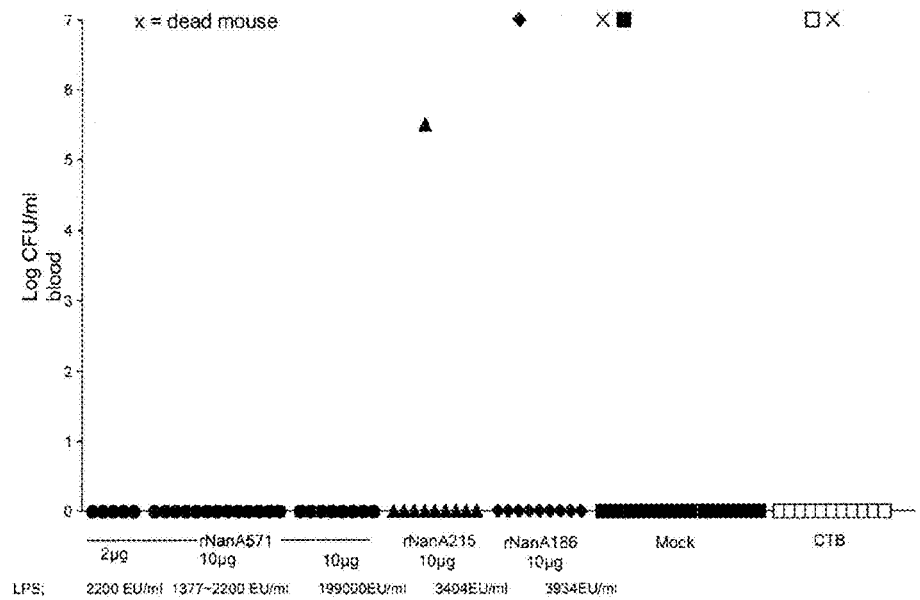
FIG. 19 shows the colony forming units (CFUs) of *S. pneumoniae* in the blood of animals immunized with rNanA571, rNanA215, rNanA186 versus mock and control animals. The triangles represent animals immunized with rNanA215. The diamonds represent animals immunized with rNanA186. The circles represent animals immunized with rNanA571. The filled in black squares represent animals given a mock immunization protocol. The empty squares represent animals given a control immunization protocol. The x's represent dead animals.

It was observed that in colonization of the CBA/N mice with TIGR4 that only a very few mice were bacteremic or died. Most mice had colonization at day 7 with no bacteremia. Some mock immunized mice or control mice had bacteremia and a few died, but the numbers were so small that there is no statistical protection against bacteremia or death in these studies (FIGS. 13 and 19). The model did yield colonization in virtually all mice, thus providing an opportunity to examine protection against colonization. Invasion of pneumococci into the lung and brain was observed in most control mice. It was determined whether immunization with NanA could protect against the invasion that occurs subsequent to colonization.

Figure 15:
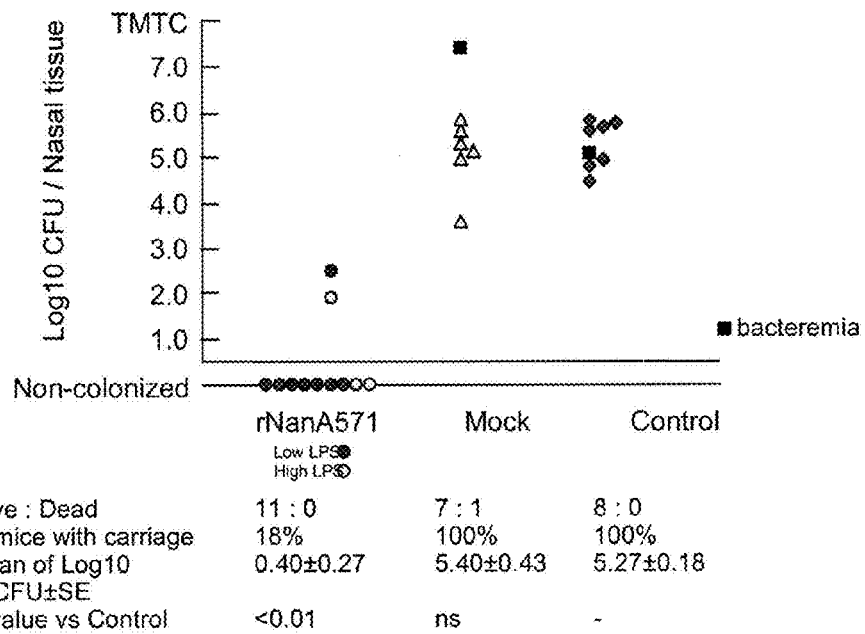
FIG. 15 shows the colony forming units (CFUs) of *S. pneumoniae* in the nasal tissue of animals immunized with rNanA571 versus mock and control animals. The black squares represent bacteremic animals. The triangles represent animals given mock immunization protocol and having CFUs in their nasal tissue. The diamonds represent animals given a control immunization protocol and having CFUs in their nasal tissue. The circles represent animals immunized with rNanA571.
Figure 16:
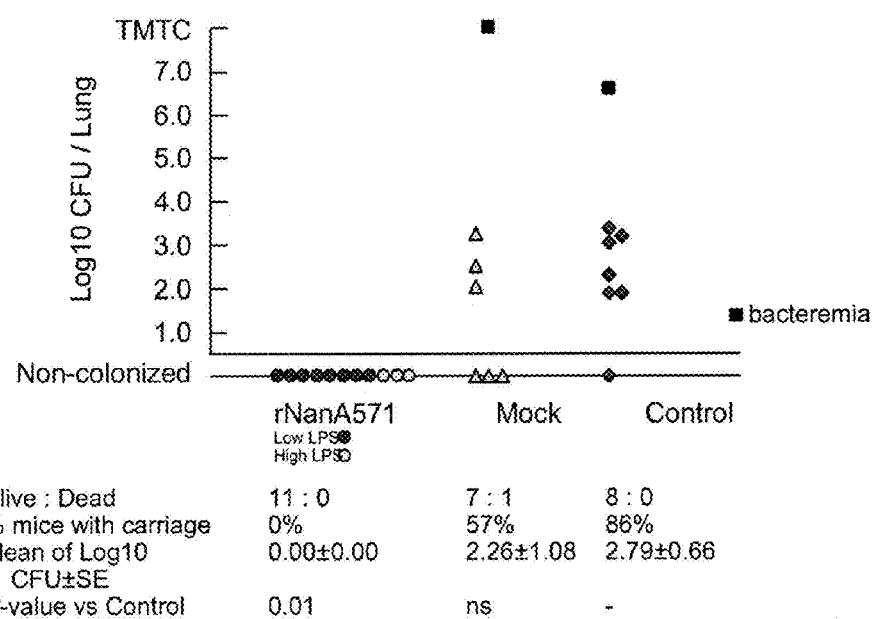
FIG. 16 shows the colony forming units (CFUs) of *S. pneumoniae* in the lung tissue of animals immunized with rNanA571 versus mock and control animals. The black squares represent bacteremic animals. The triangles represent animals given mock immunization protocol. The diamonds represent animals given a control immunization protocol. The circles represent animals immunized with rNanA571.
Figure 17:
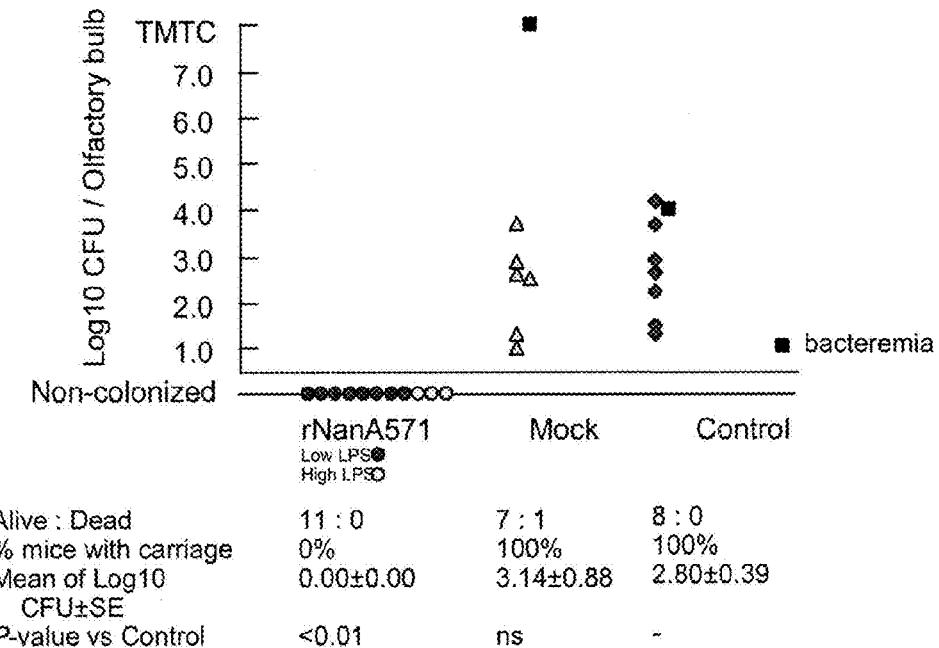
FIG. 17 shows the colony forming units (CFUs) of *S. pneumoniae* in the olfactory bulb of animals immunized with rNanA571 versus mock and control animals. The black squares represent bacteremic animals. The triangles represent animals given mock immunization protocol. The diamonds represent animals given a control immunization protocol. The circles represent animals immunized with rNanA571.
Figure 18:
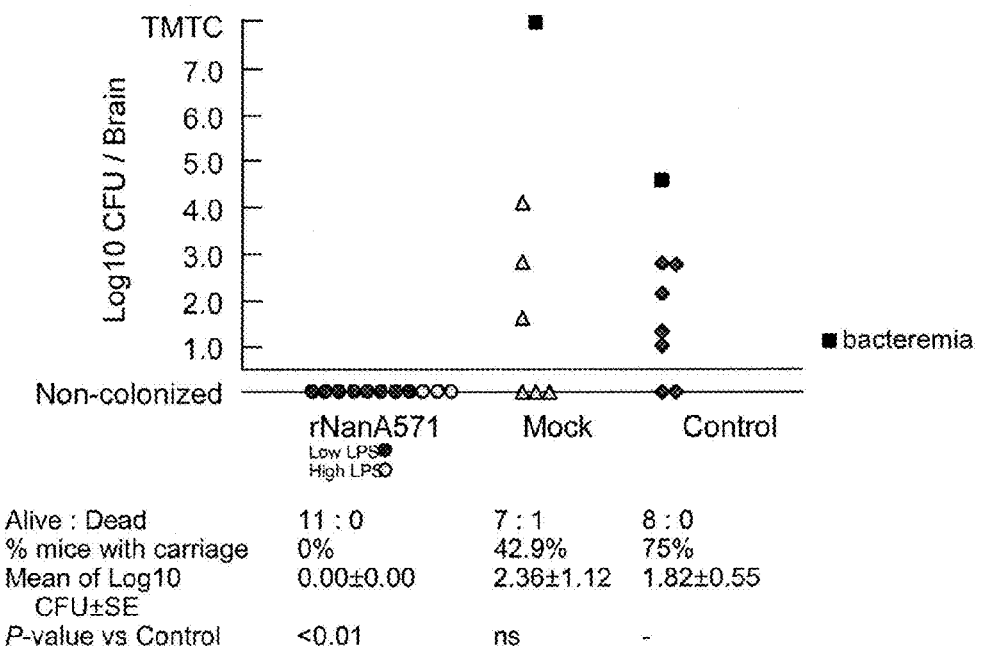
FIG. 18 shows the colony forming units (CFUs) of *S. pneumoniae* in the brain of animals immunized with rNanA571 versus mock and control animals. The black squares represent bacteremic animals. The triangles represent animals given mock immunization protocol. The diamonds represent animals given a control immunization protocol. The circles represent animals immunized with rNanA571.

Immunization with NanA571 yielded solid protection against nasal carriage as measured by detecting pneumococci in the nasal wash (FIG. 14) and nasal tissue (FIG. 15). Likewise, immunization with NanA gave complete protection from pneumococci reaching the lungs, olfactory bulb, or brain (FIG. 16, 17, or 18).

Figure 20:
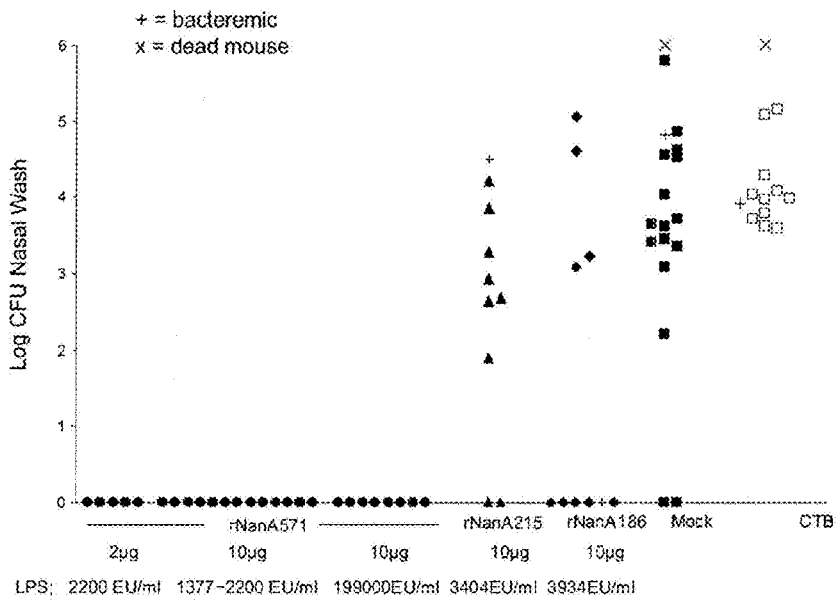
FIG. 20 shows the colony forming units (CFUs) of *S. pneumoniae* in the nasal wash of animals immunized with rNanA571, rNanA215, rNanA186 versus mock and control animals. The triangles represent animals immunized with rNanA215. The diamonds represent animals immunized with rNanA186. The circles represent animals immunized with rNanA571. The filled in black squares represent animals given a mock immunization protocol. The empty squares represent animals given a control immunization protocol. The x's represent dead animals.
Figure 21:
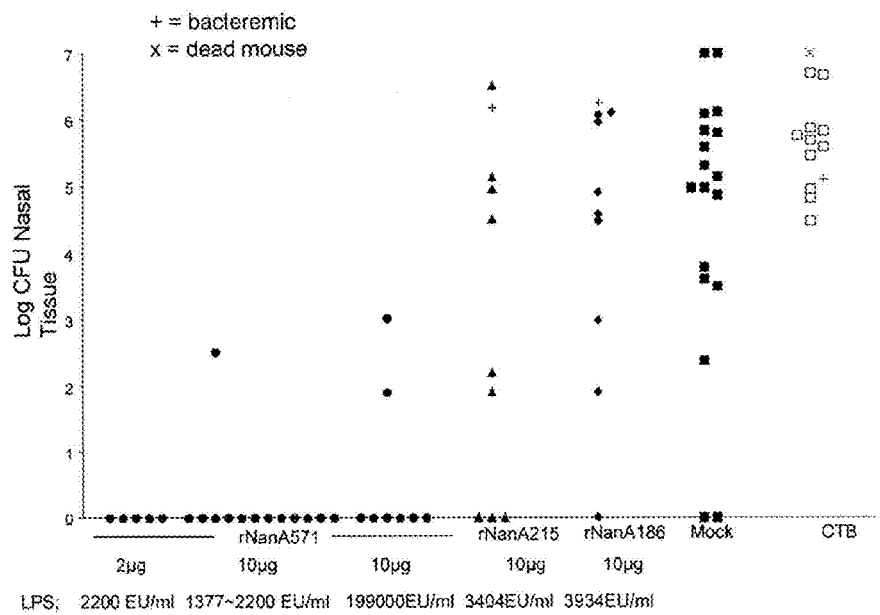
FIG. 21 shows the colony forming units (CFUs) of *S. pneumoniae* in the nasal tissue of animals immunized with rNanA571, rNanA215, rNanA186 versus mock and control animals. The triangles represent animals immunized with rNanA215. The diamonds represent animals immunized with rNanA186. The circles represent animals immunized with rNanA571. The filled in black squares represent animals give a mock immunization protocol. The empty squares represent animals given a control immunization protocol. The x's represent dead animals.
Figure 22:
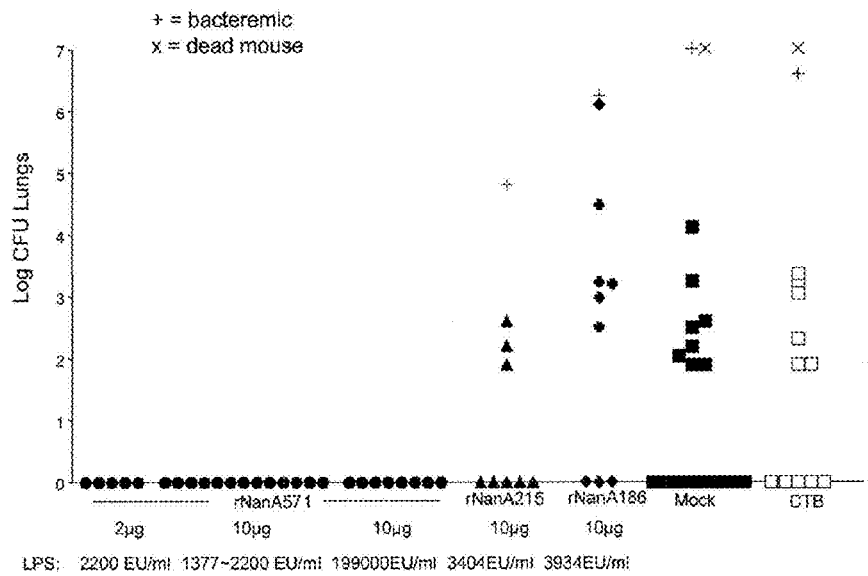
FIG. 22 shows the colony forming units (CFUs) of *S. pneumoniae* in the lungs of animals immunized with rNanA571, rNanA215, rNanA186 versus mock and control animals. The triangles represent animals immunized with rNanA215. The diamonds represent animals immunized with rNanA186. The circles represent animals immunized with rNanA571. The filled in black squares represent animals give a mock immunization protocol. The empty squares represent animals given a control immunization protocol. The x's represent dead animals.
Figure 23:
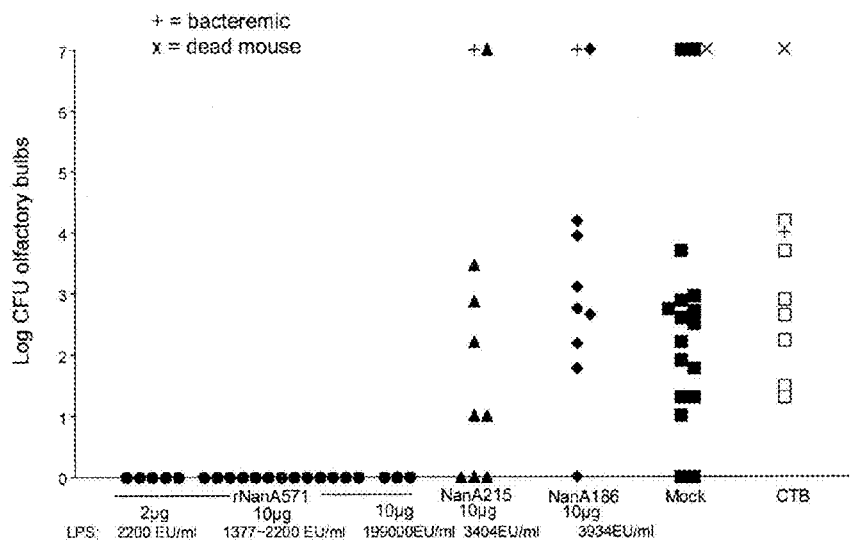
FIG. 23 shows the colony forming units (CFUs) of *S. pneumoniae* in the olfactory bulb of animals immunized with rNanA571, rNanA215, rNanA186 versus mock and control animals. The triangles represent animals immunized with rNanA215. The diamonds represent animals immunized with rNanA186. The circles represent animals immunized with rNanA571. The filled in black squares represent animals give a mock immunization protocol. The empty squares represent animals given a control immunization protocol. The x's represent dead animals.
Figure 24:
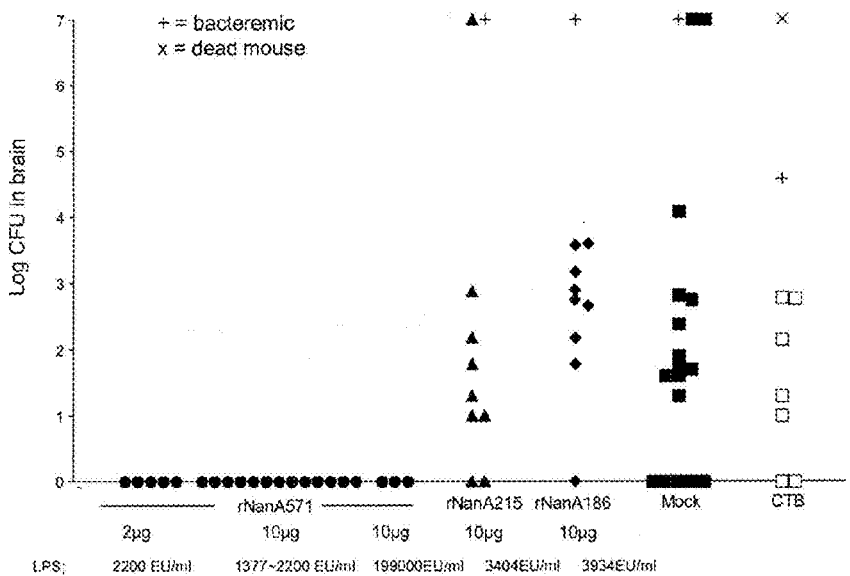
FIG. 24 shows the colony forming units (CFUs) of *S. pneumoniae* in the brain of animals immunized with rNanA571, rNanA215, rNanA186 versus mock and control animals. The triangles represent animals immunized with rNanA215. The diamonds represent animals immunized with rNanA186. The circles represent animals immunized with rNanA571. The filled in black squares represent animals give a mock immunization protocol. The empty squares represent animals given a control immunization protocol. The x's represent dead animals.

The smaller fragments neuraminidase, NanA186 and NanA215, however produced no observed statistically significant protection against colonization (FIGS. 20 and 21). These two fragments of NanA also did not elicit protection against invasion into the lung, olfactory bulbs, or brain (FIGS. 22, 23, and 24).

The fragment having 571 amino acids did not contain the N-terminus of the molecule or the C-terminus, but it covered all of the amino acids predicted to be important for enzymatic activity based on other bacterial neuraminidases. The rNanA571 fragment elicited protection against colonization. This fragment was also found to be enzymatically active using an assay for neuraminidase activity. Such an assay is described in Berry et al., J. Bacteriol 178:4854-4860 (1996).

Example 11

Site Specific Mutations in pNanA571

In order to produce a detoxified neuraminidase, two sites within the protein were targeted for site-specific mutation. The sites to mutagenize were based upon the fugue alignment given in FIG. 25 and its comparison with the sites of previous mutations made in the neuraminidases of *Salmonella typhimurium* or *Vibrio cholerae*. The first site chosen was E647, which was converted to threonine, and the second site was Y752, which was converted to phenylalanine By analogy to other neuraminidases for which the structures have been solved, Y752 is proposed to lie at the bottom of a crevice that forms the active site where it possibly interacts with the ring structure of the substrate. The glutamate residue, E647, is proposed to be involved in catalysis through the donation of a proton.

The site-specific mutations were introduced into pNanA571, creating NanA571_E647T and NanA571_Y752F. Recombinant proteins with each of these two mutations were purified and tested for neuraminidase activity using the MUAN assay at 37° C. at pH 7.0. Neither mutation exhibited any detectable neuraminidase activity with this assay under conditions in which the wild-type NanA571 protein activity was 3.9 Tmol/min/mg. The total abolishment of activity is consistent with the proposed activities as based on the alignment with structures previously known.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A method of reducing pneumococcal nasal carriage in a subject comprising administering to the subject a polypeptide comprising the amino acid sequence of SEQ ID NO:19, a polypeptide comprising the amino acid sequence of SEQ ID NO:35, or a polypeptide comprising the amino acid sequence of SEQ ID NO:36, wherein the polypeptide elicits an anti-neuraminidase immune response in the subject, wherein the polypeptide is administered under conditions that reduce or prevent the nasal carriage, and wherein the polypeptide does not consist of SEQ ID NO:15 or SEQ ID NO:16.

* * * * *

SEQUENCE LISTING

```
<160> NUMBER OF SEQ ID NOS: 41

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
atttctgtaa cagctaccaa cga                                              23

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gaattccctg tcttttcaaa gtc                                              23

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ccgatacact ctcttcccga                                                  20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
acagttggtg ctaaggaggc                                                  20

<210> SEQ ID NO 5
<211> LENGTH: 15
<212> TYPE: PRT
<213> ORGANISM: Artificial Sequence
<220> FEATURE:
<223> OTHER INFORMATION: Syntheticaly generated peptide
```

-continued

<400> SEQUENCE: 5

Val Trp Arg Leu Leu Ala Pro Pro Phe Ser Asn Arg Leu Leu Pro
1               5                   10                  15

<210> SEQ ID NO 6
<211> LENGTH: 34
<212> TYPE: DNA
<213> ORGANISM: Artificial Sequence
<220> FEATURE:
<223> OTHER INFORMATION: Primer

<400> SEQUENCE: 6
cgcggatcct catactgggt taggaaagtc gtcg                                    34

<210> SEQ ID NO 7
<211> LENGTH: 37
<212> TYPE: DNA
<213> ORGANISM: Artificial Sequence
<220> FEATURE:
<223> OTHER INFORMATION: Primer

<400> SEQUENCE: 7
ggaattccat atgccgacag cagaactacc taaaggc                                 37

<210> SEQ ID NO 8
<211> LENGTH: 41
<212> TYPE: DNA
<213> ORGANISM: Artificial Sequence
<220> FEATURE:
<223> OTHER INFORMATION: Primer

<400> SEQUENCE: 8
ggaattccat atgctggcaa atgaaactca actttcgggg g                            41

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
cgcggatcca tcggctttga ccatcggag                                          29

<210> SEQ ID NO 10
<211> LENGTH: 38
<212> TYPE: DNA
<213> ORGANISM: Artificial Sequence
<220> FEATURE:
<223> OTHER INFORMATION: Primer

<400> SEQUENCE: 10
ggaattccat atgcgtattc cagcacttct caagacag                                38

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ggaacattac ctcgcaaaag g                                                  21

-continued

```
<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
tacccgcagg cataacatc                                                    19

<210> SEQ ID NO 13
<211> LENGTH: 5
<212> TYPE: PRT
<213> ORGANISM: Artificial Sequence
<220> FEATURE:
<223> OTHER INFORMATION: Exemplary motif

<400> SEQUENCE: 13

Leu Pro Glu Thr Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 3
<223> OTHER INFORMATION: Xaa = any amino acid.

<400> SEQUENCE: 14

Leu Pro Xaa Thr Gly
1               5

<210> SEQ ID NO 15
<211> LENGTH: 1035
<212> TYPE: PRT
<213> ORGANISM: Streptococcus pneumoniae

<400> SEQUENCE: 15

Met Ser Tyr Phe Arg Asn Arg Asp Ile Asp Ile Glu Arg Asn Ser Met
1               5                   10                  15

Asn Arg Ser Val Gln Glu Arg Lys Cys Arg Tyr Ser Ile Arg Lys Leu
                20                  25                  30

Ser Val Gly Ala Val Ser Met Ile Val Gly Ala Val Val Phe Gly Thr
            35                  40                  45

Ser Pro Val Leu Ala Gln Glu Gly Ala Ser Glu Gln Pro Leu Ala Asn
        50                  55                  60

Glu Thr Gln Leu Ser Gly Glu Ser Ser Thr Leu Thr Asp Thr Glu Lys
65                  70                  75                  80

Ser Gln Pro Ser Ser Glu Thr Glu Leu Ser Gly Asn Lys Gln Glu Gln
                85                  90                  95

Glu Arg Lys Asp Lys Gln Glu Lys Ile Pro Arg Asp Tyr Tyr Ala
                100                 105                 110

Arg Asp Leu Glu Asn Val Glu Thr Val Ile Glu Lys Glu Asp Val Glu
            115                 120                 125

Thr Asn Ala Ser Asn Gly Gln Arg Val Asp Leu Ser Ser Glu Leu Asp
        130                 135                 140

Lys Leu Lys Lys Leu Glu Asn Ala Thr Val His Met Glu Phe Lys Pro
145                 150                 155                 160
```

```
Asp Ala Lys Ala Pro Ala Phe Tyr Asn Leu Phe Ser Val Ser Ser Ala
            165                 170                 175

Thr Lys Lys Asp Glu Tyr Phe Thr Met Ala Val Tyr Asn Asn Thr Ala
        180                 185                 190

Thr Leu Glu Gly Arg Gly Ser Asp Gly Lys Gln Phe Tyr Asn Asn Tyr
        195                 200                 205

Asn Asp Ala Pro Leu Lys Val Lys Pro Gly Gln Trp Asn Ser Val Thr
210                 215                 220

Phe Thr Val Glu Lys Pro Thr Ala Glu Leu Pro Lys Gly Arg Val Arg
225                 230                 235                 240

Leu Tyr Val Asn Gly Val Leu Ser Arg Thr Ser Leu Arg Ser Gly Asn
            245                 250                 255

Phe Ile Lys Asp Met Pro Asp Val Thr His Val Gln Ile Gly Ala Thr
        260                 265                 270

Lys Arg Ala Asn Asn Thr Val Trp Gly Ser Asn Leu Gln Ile Arg Asn
        275                 280                 285

Leu Thr Val Tyr Asn Arg Ala Leu Thr Pro Glu Glu Val Gln Lys Arg
        290                 295                 300

Ser Gln Leu Phe Lys Arg Ser Asp Leu Glu Lys Lys Leu Pro Glu Gly
305                 310                 315                 320

Ala Ala Leu Thr Glu Lys Thr Asp Ile Phe Glu Ser Gly Arg Asn Gly
            325                 330                 335

Lys Pro Asn Lys Asp Gly Ile Lys Ser Tyr Arg Ile Pro Ala Leu Leu
        340                 345                 350

Lys Thr Asp Lys Gly Thr Leu Ile Ala Gly Ala Asp Glu Arg Arg Leu
        355                 360                 365

His Ser Ser Asp Trp Gly Asp Ile Gly Met Val Ile Arg Arg Ser Glu
        370                 375                 380

Asp Asn Gly Lys Thr Trp Gly Asp Arg Val Thr Ile Thr Asn Leu Arg
385                 390                 395                 400

Asp Asn Pro Lys Ala Ser Asp Pro Ser Ile Gly Ser Pro Val Asn Ile
            405                 410                 415

Asp Met Val Leu Val Gln Asp Pro Glu Thr Lys Arg Ile Phe Ser Ile
        420                 425                 430

Tyr Asp Met Phe Pro Glu Gly Lys Gly Ile Phe Gly Met Ser Ser Gln
        435                 440                 445

Lys Glu Glu Ala Tyr Lys Lys Ile Asp Gly Lys Thr Tyr Gln Ile Leu
        450                 455                 460

Tyr Arg Glu Gly Glu Lys Gly Ala Tyr Thr Ile Arg Glu Asn Gly Thr
465                 470                 475                 480

Val Tyr Thr Pro Asp Gly Lys Ala Thr Asp Tyr Arg Val Val Val Asp
            485                 490                 495

Pro Val Lys Pro Ala Tyr Ser Asp Lys Gly Asp Leu Tyr Lys Gly Asn
        500                 505                 510

Gln Leu Leu Gly Asn Ile Tyr Phe Thr Thr Asn Lys Thr Ser Pro Phe
        515                 520                 525

Arg Ile Ala Lys Asp Ser Tyr Leu Trp Met Ser Tyr Ser Asp Asp Asp
        530                 535                 540

Gly Lys Thr Trp Ser Ala Pro Gln Asp Ile Thr Pro Met Val Lys Ala
545                 550                 555                 560

Asp Trp Met Lys Phe Leu Gly Val Gly Pro Gly Thr Gly Ile Val Leu
            565                 570                 575
```

```
Arg Asn Gly Pro His Lys Gly Arg Ile Leu Ile Pro Val Tyr Thr Thr
            580                 585                 590
Asn Asn Val Ser His Leu Asn Gly Ser Gln Ser Ser Arg Ile Ile Tyr
        595                 600                 605
Ser Asp Asp His Gly Lys Thr Trp His Ala Gly Glu Ala Val Asn Asp
    610                 615                 620
Asn Arg Gln Val Asp Gly Gln Lys Ile His Ser Ser Thr Met Asn Asn
625                 630                 635                 640
Arg Arg Ala Gln Asn Thr Glu Ser Thr Val Val Gln Leu Asn Asn Gly
                645                 650                 655
Asp Val Lys Leu Phe Met Arg Gly Leu Thr Gly Asp Leu Gln Val Ala
            660                 665                 670
Thr Ser Lys Asp Gly Gly Val Thr Trp Glu Lys Asp Ile Lys Arg Tyr
        675                 680                 685
Pro Gln Val Lys Asp Val Tyr Val Gln Met Ser Ala Ile His Thr Met
    690                 695                 700
His Glu Gly Lys Glu Tyr Ile Ile Leu Ser Asn Ala Gly Gly Pro Lys
705                 710                 715                 720
Arg Glu Asn Gly Met Val His Leu Ala Arg Val Glu Glu Asn Gly Glu
                725                 730                 735
Leu Thr Trp Leu Lys His Asn Pro Ile Gln Lys Gly Glu Phe Ala Tyr
            740                 745                 750
Asn Ser Leu Gln Glu Leu Gly Asn Gly Glu Tyr Gly Ile Leu Tyr Glu
        755                 760                 765
His Thr Glu Lys Gly Gln Asn Ala Tyr Thr Leu Ser Phe Arg Lys Phe
    770                 775                 780
Asn Trp Asp Phe Leu Ser Lys Asp Leu Ile Ser Pro Thr Glu Ala Lys
785                 790                 795                 800
Val Lys Arg Thr Arg Glu Met Gly Lys Gly Val Ile Gly Leu Glu Phe
                805                 810                 815
Asp Ser Glu Val Leu Val Asn Lys Ala Pro Thr Leu Gln Leu Ala Asn
            820                 825                 830
Gly Lys Thr Ala Arg Phe Met Thr Gln Tyr Asp Thr Lys Thr Leu Leu
        835                 840                 845
Phe Thr Val Asp Ser Glu Asp Met Gly Gln Lys Val Thr Gly Leu Ala
    850                 855                 860
Glu Gly Ala Ile Glu Ser Met His Asn Leu Pro Val Ser Val Ala Gly
865                 870                 875                 880
Thr Lys Leu Ser Asn Gly Met Asn Gly Ser Glu Ala Ala Val His Glu
                885                 890                 895
Val Pro Glu Tyr Thr Gly Pro Leu Gly Thr Ser Gly Glu Glu Pro Ala
            900                 905                 910
Pro Thr Val Glu Lys Pro Glu Tyr Thr Gly Pro Leu Gly Thr Ser Gly
        915                 920                 925
Glu Glu Pro Ala Pro Thr Val Glu Lys Pro Glu Tyr Thr Gly Pro Leu
    930                 935                 940
Gly Thr Ala Gly Glu Glu Ala Pro Thr Val Glu Lys Pro Glu Phe
945                 950                 955                 960
Thr Gly Gly Val Asn Gly Thr Glu Pro Ala Val His Glu Ile Ala Glu
                965                 970                 975
Tyr Lys Gly Ser Asp Ser Leu Val Thr Leu Thr Thr Lys Glu Asp Tyr
            980                 985                 990
```

Thr Tyr Lys Ala Pro Leu Ala Gln Gln Ala Leu Pro Glu Thr Gly Asn
            995                1000                1005

Lys Glu Ser Asp Leu Leu Ala Ser Leu Gly Leu Thr Ala Phe Phe Leu
        1010                1015                1020

Gly Leu Phe Thr Leu Gly Lys Lys Arg Glu Gln
1025                1030

<210> SEQ ID NO 16
<211> LENGTH: 962
<212> TYPE: PRT
<213> ORGANISM: Streptococcus pneumoniae

<400> SEQUENCE: 16

Met Asn Arg Ser Val Gln Glu Arg Lys Cys Arg Tyr Ser Ile Arg Lys
1               5                   10                  15

Leu Ser Val Gly Ala Val Ser Met Ile Val Gly Ala Val Val Asn Gly
            20                  25                  30

Thr Ser Pro Val Leu Ala Gln Glu Gly Ala Ser Glu Gln Pro Leu Ala
        35                  40                  45

Asn Glu Thr Gln Leu Ser Gly Glu Ser Ser Thr Leu Thr Asp Thr Glu
    50                  55                  60

Lys Ser Gln Pro Ser Ser Glu Thr Glu Leu Ser Gly Asn Lys Gln Glu
65                  70                  75                  80

Gln Glu Arg Lys Asp Lys Gln Glu Glu Lys Ile Pro Arg Asp Tyr Tyr
                85                  90                  95

Ala Arg Asp Leu Glu Asn Val Glu Thr Val Ile Glu Lys Glu Asp Val
            100                 105                 110

Glu Thr Asn Ala Ser Asn Gly Gln Arg Val Asp Leu Ser Ser Glu Leu
        115                 120                 125

Asp Lys Leu Lys Lys Leu Glu Asn Ala Thr Val His Met Glu Asn Lys
    130                 135                 140

Pro Asp Ala Lys Ala Pro Ala Phe Tyr Asn Leu Asn Ser Val Ser Ser
145                 150                 155                 160

Ala Thr Lys Lys Asp Glu Tyr Phe Thr Met Ala Val Tyr Asn Asn Thr
                165                 170                 175

Ala Thr Leu Glu Gly Arg Gly Ser Asp Gly Lys Gln Asn Tyr Asn Asn
            180                 185                 190

Tyr Asn Asp Ala Pro Leu Lys Val Lys Pro Gly Gln Trp Asn Ser Val
        195                 200                 205

Thr Phe Thr Val Glu Lys Pro Thr Ala Glu Leu Pro Lys Gly Arg Val
    210                 215                 220

Arg Leu Tyr Val Asn Gly Val Leu Ser Arg Thr Ser Leu Arg Ser Gly
225                 230                 235                 240

Asn Phe Ile Lys Asp Met Pro Asp Val Thr His Val Gln Ile Gly Ala
                245                 250                 255

Thr Lys Arg Ala Asn Asn Thr Val Trp Gly Ser Asn Leu Gln Ile Arg
            260                 265                 270

Asn Leu Thr Val Tyr Asn Arg Ala Leu Thr Pro Glu Glu Val Gln Lys
        275                 280                 285

Arg Ser Gln Leu Asn Lys Arg Ser Asp Leu Glu Lys Lys Leu Pro Glu
    290                 295                 300

Gly Ala Ala Leu Thr Glu Lys Thr Asp Ile Phe Glu Ser Gly Arg Asn
305                 310                 315                 320

Gly Asn Pro Asn Lys Asp Gly Ile Lys Ser Tyr Arg Ile Pro Ala Leu
                325                 330                 335

```
Leu Lys Thr Asp Lys Gly Thr Leu Ile Ala Gly Ala Asp Glu Arg Arg
                340                 345                 350

Leu His Ser Ser Asp Trp Gly Asp Ile Gly Met Val Ile Arg Arg Ser
            355                 360                 365

Glu Asp Asn Gly Lys Thr Trp Gly Asp Arg Val Thr Ile Thr Asn Leu
        370                 375                 380

Arg Asp Asn Pro Lys Ala Ser Asp Pro Ser Ile Gly Ser Pro Val Asn
385                 390                 395                 400

Ile Asp Met Val Leu Val Gln Asp Pro Glu Thr Lys Arg Ile Asn Ser
                405                 410                 415

Ile Tyr Asp Met Phe Pro Glu Gly Lys Gly Ile Asn Gly Met Ser Ser
            420                 425                 430

Gln Lys Glu Glu Ala Tyr Lys Lys Ile Asp Gly Lys Thr Tyr Gln Ile
        435                 440                 445

Leu Tyr Arg Glu Gly Glu Lys Gly Ala Tyr Thr Ile Arg Glu Asn Gly
    450                 455                 460

Thr Val Tyr Thr Pro Asp Gly Lys Ala Thr Asp Tyr Arg Val Val Val
465                 470                 475                 480

Asp Pro Val Lys Pro Ala Tyr Ser Asp Lys Gly Asp Leu Tyr Lys Gly
                485                 490                 495

Asp Gln Leu Leu Gly Asn Ile Tyr Phe Thr Thr Asn Lys Thr Ser Pro
            500                 505                 510

Asn Arg Ile Ala Lys Asp Ser Tyr Leu Trp Met Ser Tyr Ser Asp Asp
        515                 520                 525

Asp Gly Lys Thr Trp Ser Ala Pro Gln Asp Ile Thr Pro Met Val Lys
    530                 535                 540

Ala Asp Trp Met Lys Phe Leu Gly Val Gly Pro Gly Thr Gly Ile Val
545                 550                 555                 560

Leu Arg Asn Gly Pro His Lys Gly Arg Ile Leu Ile Pro Val Tyr Thr
                565                 570                 575

Thr Asn Asn Val Ser His Leu Asp Gly Ser Gln Ser Ser Arg Val Ile
            580                 585                 590

Tyr Ser Asp Asp His Gly Lys Thr Trp His Ala Gly Glu Ala Val Asn
        595                 600                 605

Asp Asn Arg Gln Val Asp Gly Gln Lys Ile His Ser Ser Thr Met Asn
    610                 615                 620

Asn Arg Arg Ala Gln Asn Thr Glu Ser Thr Val Val Gln Leu Asn Asn
625                 630                 635                 640

Gly Asp Val Lys Leu Asn Met Arg Gly Leu Thr Gly Asp Leu Gln Val
                645                 650                 655

Ala Thr Ser Lys Asp Gly Gly Val Thr Trp Glu Lys Asp Ile Lys Arg
            660                 665                 670

Tyr Pro Gln Val Lys Asp Val Tyr Val Gln Met Ser Ala Ile His Thr
        675                 680                 685

Met His Glu Gly Lys Glu Tyr Ile Ile Leu Ser Asn Ala Gly Gly Pro
    690                 695                 700

Lys Arg Glu Asn Gly Met Val His Leu Ala Arg Val Glu Glu Asn Gly
705                 710                 715                 720

Glu Leu Thr Trp Leu Lys His Asn Pro Ile Gln Lys Gly Glu Asn Ala
                725                 730                 735

Tyr Asn Ser Leu Gln Glu Leu Gly Asn Gly Glu Tyr Gly Ile Leu Tyr
            740                 745                 750
```

```
Glu His Thr Glu Lys Gly Gln Asn Ala Tyr Thr Leu Ser Asn Arg Lys
            755                 760                 765

Asn Asn Trp Glu Asn Leu Ser Lys Asn Leu Ile Ser Pro Thr Glu Ala
    770                 775                 780

Asn Asn Arg Asp Gly Gln Arg Asp Gly Gln Arg Ser Tyr Trp Leu
785                 790                 795                 800

Gly Val Arg Leu Arg Ser Ile Gly Gln Gln Gly Ser Asn Pro Ser Ile
                805                 810                 815

Gly Lys Trp Asn Asn Ser Asp Asn Pro Asn Pro Val Asn Asn Gln Asp
            820                 825                 830

Leu Val Val Cys Ser Arg Asn Gly Arg Tyr Arg Thr Gly Asn Tyr Trp
                835                 840                 845

Tyr Ser Asn Arg Lys His Arg Lys Tyr Ala Asn Ser Ser Cys Lys Ser
850                 855                 860

Ser Arg Cys Gln Ser Ser Trp Arg Ser Lys Trp Asn Gln Ser Ser Gly
865                 870                 875                 880

Ala Asn Ser Ser Arg Ile Tyr Arg Gly Ser Asn Trp Tyr Arg Ala Ser
                885                 890                 895

Cys Ser Asn Asn Arg Arg Val Asn Gly Ile Asn Phe Ala Cys Asn Ser
                900                 905                 910

Tyr Tyr Lys Lys Arg Leu Tyr Leu Gln Ser Ser Ser Cys Ser Ala Gly
            915                 920                 925

Thr Ser Asn Asn Arg Lys Gln Gly Glu Asn Pro Pro Ser Phe Thr Arg
            930                 935                 940

Thr Asn Ser Asn Leu Pro Trp Ser Val Tyr Ala Arg Glu Lys Glu Arg
945                 950                 955                 960

Thr Ile

<210> SEQ ID NO 17
<211> LENGTH: 382
<212> TYPE: PRT
<213> ORGANISM: Streptococcus typhimirium

<400> SEQUENCE: 17

Met Thr Val Glu Lys Ser Val Val Phe Lys Ala Glu Gly Glu His Phe
 1               5                  10                  15

Thr Asp Gln Lys Gly Asn Thr Ile Val Gly Ser Gly Ser Gly Gly Thr
            20                  25                  30

Thr Lys Tyr Phe Arg Ile Pro Ala Met Cys Thr Thr Ser Lys Gly Thr
        35                  40                  45

Ile Val Val Phe Ala Asp Ala Arg His Asn Thr Ala Ser Asp Gln Ser
 50                  55                  60

Phe Ile Asp Thr Ala Ala Arg Ser Thr Asp Gly Gly Lys Thr Trp
65                  70                  75                  80

Asn Lys Lys Ile Ala Ile Tyr Asn Asp Arg Val Asn Ser Lys Leu Ser
                85                  90                  95

Arg Val Met Asp Pro Thr Cys Ile Val Ala Asn Ile Gln Gly Arg Glu
            100                 105                 110

Thr Ile Leu Val Met Val Gly Lys Trp Asn Asn Asn Asp Lys Thr Trp
        115                 120                 125

Gly Ala Tyr Arg Asp Lys Ala Pro Asp Thr Asp Trp Asp Leu Val Leu
    130                 135                 140

Tyr Lys Ser Thr Asp Asp Gly Val Thr Phe Ser Lys Val Glu Thr Asn
145                 150                 155                 160
```

```
Ile His Asp Ile Val Thr Lys Asn Gly Thr Ile Ser Ala Met Leu Gly
                165                 170                 175

Gly Val Gly Ser Gly Leu Gln Leu Asn Asp Gly Lys Leu Val Phe Pro
            180                 185                 190

Val Gln Met Val Arg Thr Lys Asn Ile Thr Thr Val Leu Asn Thr Ser
        195                 200                 205

Phe Ile Tyr Ser Thr Asp Gly Ile Thr Trp Ser Leu Pro Ser Gly Tyr
    210                 215                 220

Cys Glu Gly Phe Gly Ser Glu Asn Asn Ile Glu Phe Asn Ala Ser
225                 230                 235                 240

Leu Val Asn Asn Ile Arg Asn Ser Gly Leu Arg Arg Ser Phe Glu Thr
                245                 250                 255

Lys Asp Phe Gly Lys Thr Trp Thr Glu Phe Pro Pro Met Asp Lys Lys
            260                 265                 270

Val Asp Asn Arg Asn His Gly Val Gln Gly Ser Thr Ile Thr Ile Pro
        275                 280                 285

Ser Gly Asn Lys Leu Val Ala Ala His Ser Ser Ala Gln Asn Lys Asn
    290                 295                 300

Asn Asp Tyr Thr Arg Ser Asp Ile Ser Leu Tyr Ala His Asn Leu Tyr
305                 310                 315                 320

Ser Gly Glu Val Lys Leu Ile Asp Asp Phe Tyr Pro Lys Val Gly Asn
                325                 330                 335

Ala Ser Gly Ala Gly Tyr Ser Cys Leu Ser Tyr Arg Lys Asn Val Asp
            340                 345                 350

Lys Glu Thr Leu Tyr Val Val Tyr Glu Ala Asn Gly Ser Ile Glu Phe
        355                 360                 365

Gln Asp Leu Ser Arg His Leu Pro Val Ile Lys Ser Tyr Asn
    370                 375                 380

<210> SEQ ID NO 18
<211> LENGTH: 593
<212> TYPE: PRT
<213> ORGANISM: Artificial Sequence
<220> FEATURE:
<223> OTHER INFORMATION: Synthetic construct

<400> SEQUENCE: 18

Met Gly His His His His His His His His Ser Ser Gly His
1               5                   10                  15

Ile Glu Gly Arg His Met Pro Thr Ala Glu Leu Pro Lys Gly Arg Val
            20                  25                  30

Arg Leu Tyr Val Asn Gly Val Leu Ser Arg Thr Ser Leu Arg Ser Gly
        35                  40                  45

Asn Phe Ile Lys Asp Met Pro Asp Val Thr His Val Gln Ile Gly Ala
    50                  55                  60

Thr Lys Arg Ala Asn Asn Thr Val Trp Gly Ser Asn Leu Gln Ile Arg
65                  70                  75                  80

Asn Leu Thr Val Tyr Asn Arg Ala Leu Thr Pro Glu Val Gln Lys
                85                  90                  95

Arg Ser Gln Leu Phe Lys Arg Ser Asp Leu Glu Lys Lys Leu Pro Glu
            100                 105                 110

Gly Ala Ala Leu Thr Glu Lys Thr Asp Ile Phe Glu Ser Gly Arg Asn
        115                 120                 125

Gly Asn Pro Asn Lys Asp Gly Ile Lys Ser Tyr Arg Ile Pro Ala Leu
    130                 135                 140
```

-continued

Leu Lys Thr Asp Lys Gly Thr Leu Ile Ala Gly Ala Asp Glu Arg Arg
145                 150                 155                 160

Leu His Ser Ser Asp Trp Gly Asp Ile Gly Met Val Ile Arg Arg Ser
                165                 170                 175

Glu Asp Asn Gly Lys Thr Trp Gly Asp Arg Val Thr Ile Thr Asn Leu
            180                 185                 190

Arg Asp Asn Pro Lys Ala Ser Asp Pro Ser Ile Gly Ser Pro Val Asn
        195                 200                 205

Ile Asp Met Val Leu Val Gln Asp Pro Glu Thr Lys Arg Ile Phe Ser
    210                 215                 220

Ile Tyr Asp Met Phe Pro Glu Gly Lys Gly Ile Phe Gly Met Ser Ser
225                 230                 235                 240

Gln Lys Glu Glu Ala Tyr Lys Lys Ile Asp Gly Lys Thr Tyr Gln Ile
                245                 250                 255

Leu Tyr Arg Glu Gly Glu Lys Gly Ala Tyr Thr Ile Arg Glu Asn Gly
            260                 265                 270

Thr Val Tyr Thr Pro Asp Gly Lys Ala Thr Asp Tyr Arg Val Val Val
        275                 280                 285

Asp Pro Val Lys Pro Ala Tyr Ser Asp Lys Gly Asp Leu Tyr Lys Gly
    290                 295                 300

Asp Gln Leu Leu Gly Asn Ile Tyr Phe Thr Thr Asn Lys Thr Ser Pro
305                 310                 315                 320

Phe Arg Ile Ala Lys Asp Ser Tyr Leu Trp Met Ser Tyr Ser Asp Asp
                325                 330                 335

Asp Gly Lys Thr Trp Ser Ala Pro Gln Asp Ile Thr Pro Met Val Lys
            340                 345                 350

Ala Asp Trp Met Lys Phe Leu Gly Val Gly Pro Gly Thr Gly Ile Val
        355                 360                 365

Leu Arg Asn Gly Pro His Lys Gly Arg Ile Leu Ile Pro Val Tyr Thr
    370                 375                 380

Thr Asn Asn Val Ser His Leu Asp Gly Ser Gln Ser Ser Arg Val Ile
385                 390                 395                 400

Tyr Ser Asp Asp His Gly Lys Thr Trp His Ala Gly Glu Ala Val Asn
                405                 410                 415

Asp Asn Arg Gln Val Asp Gly Gln Lys Ile His Ser Ser Thr Met Asn
            420                 425                 430

Asn Arg Arg Ala Gln Asn Thr Glu Ser Thr Val Val Gln Leu Asn Asn
        435                 440                 445

Gly Asp Val Lys Leu Phe Met Arg Gly Leu Thr Gly Asp Leu Gln Val
    450                 455                 460

Ala Thr Ser Lys Asp Gly Gly Val Thr Trp Glu Lys Asp Ile Lys Arg
465                 470                 475                 480

Tyr Pro Gln Val Lys Asp Val Tyr Val Gln Met Ser Ala Ile His Thr
                485                 490                 495

Met His Glu Gly Lys Glu Tyr Ile Ile Leu Ser Asn Ala Gly Gly Pro
            500                 505                 510

Lys Arg Glu Asn Gly Met Val His Leu Ala Arg Val Glu Glu Asn Gly
        515                 520                 525

Glu Leu Thr Trp Leu Lys His Asn Pro Ile Gln Lys Gly Glu Phe Ala
    530                 535                 540

Tyr Asn Ser Leu Gln Glu Leu Gly Asn Gly Glu Tyr Gly Ile Leu Tyr
545                 550                 555                 560

```
Glu His Thr Glu Lys Gly Gln Asn Ala Tyr Thr Leu Ser Phe Arg Lys
            565                 570                 575

Phe Asn Trp Glu Phe Leu Ser Lys Asn Leu Ile Ser Pro Thr Glu Ala
            580                 585                 590

Asn

<210> SEQ ID NO 19
<211> LENGTH: 571
<212> TYPE: PRT
<213> ORGANISM: Streptococcus pneumoniae

<400> SEQUENCE: 19

Pro Thr Ala Glu Leu Pro Lys Gly Arg Val Arg Leu Tyr Val Asn Gly
  1               5                  10                  15

Val Leu Ser Arg Thr Ser Leu Arg Ser Gly Asn Phe Ile Lys Asp Met
             20                  25                  30

Pro Asp Val Thr His Val Gln Ile Gly Ala Thr Lys Arg Ala Asn Asn
         35                  40                  45

Thr Val Trp Gly Ser Asn Leu Gln Ile Arg Asn Leu Thr Val Tyr Asn
 50                  55                  60

Arg Ala Leu Thr Pro Glu Val Gln Lys Arg Ser Gln Leu Phe Lys
 65                  70                  75                  80

Arg Ser Asp Leu Glu Lys Lys Leu Pro Glu Gly Ala Ala Leu Thr Glu
                 85                  90                  95

Lys Thr Asp Ile Phe Glu Ser Gly Arg Asn Gly Asn Pro Asn Lys Asp
            100                 105                 110

Gly Ile Lys Ser Tyr Arg Ile Pro Ala Leu Leu Lys Thr Asp Lys Gly
        115                 120                 125

Thr Leu Ile Ala Gly Ala Asp Glu Arg Arg Leu His Ser Ser Asp Trp
130                 135                 140

Gly Asp Ile Gly Met Val Ile Arg Arg Ser Glu Asp Asn Gly Lys Thr
145                 150                 155                 160

Trp Gly Asp Arg Val Thr Ile Thr Asn Leu Arg Asp Asn Pro Lys Ala
                165                 170                 175

Ser Asp Pro Ser Ile Gly Ser Pro Val Asn Ile Asp Met Val Leu Val
            180                 185                 190

Gln Asp Pro Glu Thr Lys Arg Ile Phe Ser Ile Tyr Asp Met Phe Pro
        195                 200                 205

Glu Gly Lys Gly Ile Phe Gly Met Ser Ser Gln Lys Glu Glu Ala Tyr
    210                 215                 220

Lys Lys Ile Asp Gly Lys Thr Tyr Gln Ile Leu Tyr Arg Glu Gly Glu
225                 230                 235                 240

Lys Gly Ala Tyr Thr Ile Arg Glu Asn Gly Thr Val Tyr Thr Pro Asp
                245                 250                 255

Gly Lys Ala Thr Asp Tyr Arg Val Val Val Asp Pro Val Lys Pro Ala
            260                 265                 270

Tyr Ser Asp Lys Gly Asp Leu Tyr Lys Gly Asp Gln Leu Leu Gly Asn
        275                 280                 285

Ile Tyr Phe Thr Thr Asn Lys Thr Ser Pro Phe Arg Ile Ala Lys Asp
    290                 295                 300

Ser Tyr Leu Trp Met Ser Tyr Ser Asp Asp Asp Gly Lys Thr Trp Ser
305                 310                 315                 320

Ala Pro Gln Asp Ile Thr Pro Met Val Lys Ala Asp Trp Met Lys Phe
                325                 330                 335
```

Leu Gly Val Gly Pro Gly Thr Gly Ile Val Leu Arg Asn Gly Pro His
              340                 345                 350

Lys Gly Arg Ile Leu Ile Pro Val Tyr Thr Thr Asn Asn Val Ser His
          355                 360                 365

Leu Asp Gly Ser Gln Ser Ser Arg Val Ile Tyr Ser Asp Asp His Gly
      370                 375                 380

Lys Thr Trp His Ala Gly Glu Ala Val Asn Asp Asn Arg Gln Val Asp
385                 390                 395                 400

Gly Gln Lys Ile His Ser Ser Thr Met Asn Asn Arg Arg Ala Gln Asn
                405                 410                 415

Thr Glu Ser Thr Val Val Gln Leu Asn Asn Gly Asp Val Lys Leu Phe
            420                 425                 430

Met Arg Gly Leu Thr Gly Asp Leu Gln Val Ala Thr Ser Lys Asp Gly
        435                 440                 445

Gly Val Thr Trp Glu Lys Asp Ile Lys Arg Tyr Pro Gln Val Lys Asp
    450                 455                 460

Val Tyr Val Gln Met Ser Ala Ile His Thr Met His Glu Gly Lys Glu
465                 470                 475                 480

Tyr Ile Ile Leu Ser Asn Ala Gly Gly Pro Lys Arg Glu Asn Gly Met
                485                 490                 495

Val His Leu Ala Arg Val Glu Glu Asn Gly Glu Leu Thr Trp Leu Lys
            500                 505                 510

His Asn Pro Ile Gln Lys Gly Glu Phe Ala Tyr Asn Ser Leu Gln Glu
        515                 520                 525

Leu Gly Asn Gly Glu Tyr Gly Ile Leu Tyr Glu His Thr Glu Lys Gly
    530                 535                 540

Gln Asn Ala Tyr Thr Leu Ser Phe Arg Lys Phe Asn Trp Glu Phe Leu
545                 550                 555                 560

Ser Lys Asn Leu Ile Ser Pro Thr Glu Ala Asn
                565                 570

<210> SEQ ID NO 20
<211> LENGTH: 240
<212> TYPE: PRT
<213> ORGANISM: Artificial Sequence
<220> FEATURE:
<223> OTHER INFORMATION: Synthetic construct

<400> SEQUENCE: 20

Met Gly His His His His His His His His Ser Ser Gly His
 1               5                  10                  15

Ile Glu Gly Arg His Met Arg Ile Pro Ala Leu Leu Lys Thr Asp Lys
            20                  25                  30

Gly Thr Leu Ile Ala Gly Ala Asp Glu Arg Arg Leu His Ser Ser Asp
        35                  40                  45

Trp Gly Asp Ile Gly Met Val Ile Arg Arg Ser Glu Asp Asn Gly Lys
    50                  55                  60

Thr Trp Gly Asp Arg Val Thr Ile Thr Asn Leu Arg Asp Asn Pro Lys
65                  70                  75                  80

Ala Ser Asp Pro Ser Ile Gly Ser Pro Val Asn Ile Asp Met Val Leu
                85                  90                  95

Val Gln Asp Pro Glu Thr Lys Arg Ile Phe Ser Ile Tyr Asp Met Phe
            100                 105                 110

Pro Glu Gly Lys Gly Ile Phe Gly Met Ser Ser Gln Lys Glu Glu Ala
        115                 120                 125

```
Tyr Lys Lys Ile Asp Gly Lys Thr Tyr Gln Ile Leu Tyr Arg Glu Gly
            130                 135                 140

Glu Lys Gly Ala Tyr Thr Ile Arg Glu Asn Gly Thr Val Tyr Thr Pro
145                 150                 155                 160

Asp Gly Lys Ala Thr Asp Tyr Arg Val Val Asp Pro Val Lys Pro
                165                 170                 175

Ala Tyr Ser Asp Lys Gly Asp Leu Tyr Lys Gly Asp Gln Leu Leu Gly
            180                 185                 190

Asn Ile Tyr Phe Thr Thr Asn Lys Thr Ser Pro Phe Arg Ile Ala Lys
            195                 200                 205

Asp Ser Tyr Leu Trp Met Ser Tyr Ser Asp Asp Gly Lys Thr Trp
210                 215                 220

Ser Ala Pro Gln Asp Ile Thr Pro Met Val Lys Ala Asp Pro Gly Cys
225                 230                 235                 240
```

<210> SEQ ID NO 21
<211> LENGTH: 215
<212> TYPE: PRT
<213> ORGANISM: Artificial Sequence
<220> FEATURE:
<223> OTHER INFORMATION: Synthetic construct

<400> SEQUENCE: 21

```
Arg Ile Pro Ala Leu Leu Lys Thr Asp Lys Gly Thr Leu Ile Ala Gly
1               5                   10                  15

Ala Asp Glu Arg Arg Leu His Ser Ser Asp Trp Gly Asp Ile Gly Met
            20                  25                  30

Val Ile Arg Arg Ser Glu Asp Asn Gly Lys Thr Trp Gly Asp Arg Val
            35                  40                  45

Thr Ile Thr Asn Leu Arg Asp Asn Pro Lys Ala Ser Asp Pro Ser Ile
50                  55                  60

Gly Ser Pro Val Asn Ile Asp Met Val Leu Val Gln Asp Pro Glu Thr
65                  70                  75                  80

Lys Arg Ile Phe Ser Ile Tyr Asp Met Phe Pro Glu Gly Lys Gly Ile
                85                  90                  95

Phe Gly Met Ser Ser Gln Lys Glu Glu Ala Tyr Lys Lys Ile Asp Gly
            100                 105                 110

Lys Thr Tyr Gln Ile Leu Tyr Arg Glu Gly Glu Lys Gly Ala Tyr Thr
            115                 120                 125

Ile Arg Glu Asn Gly Thr Val Tyr Thr Pro Asp Gly Lys Ala Thr Asp
            130                 135                 140

Tyr Arg Val Val Asp Pro Val Lys Pro Ala Tyr Ser Asp Lys Gly
145                 150                 155                 160

Asp Leu Tyr Lys Gly Asp Gln Leu Leu Gly Asn Ile Tyr Phe Thr Thr
                165                 170                 175

Asn Lys Thr Ser Pro Phe Arg Ile Ala Lys Asp Ser Tyr Leu Trp Met
            180                 185                 190

Ser Tyr Ser Asp Asp Asp Gly Lys Thr Trp Ser Ala Pro Gln Asp Ile
            195                 200                 205

Thr Pro Met Val Lys Ala Asp
            210                 215
```

<210> SEQ ID NO 22
<211> LENGTH: 211
<212> TYPE: PRT
<213> ORGANISM: Artificial Sequence
<220> FEATURE:
<223> OTHER INFORMATION: Description of Artificial Sequence; note = synthetic construct

<400> SEQUENCE: 22

```
Met Gly His His His His His His His His Ser Ser Gly His
1               5                   10                  15

Ile Glu Gly Arg His Met Glu Phe Lys Pro Asp Ala Lys Ala Pro Ala
            20                  25                  30

Phe Tyr Asn Leu Phe Ser Val Ser Ala Thr Lys Lys Asp Glu Tyr
        35                  40                  45

Phe Thr Met Ala Val Tyr Asn Asn Thr Ala Thr Leu Glu Gly Arg Gly
50                  55                  60

Ser Asp Gly Lys Gln Phe Tyr Asn Asn Tyr Asn Asp Ala Pro Leu Lys
65                  70                  75                  80

Val Lys Pro Gly Gln Trp Asn Ser Val Thr Phe Thr Val Glu Lys Pro
                85                  90                  95

Thr Ala Glu Leu Pro Lys Gly Arg Val Arg Leu Tyr Val Asn Gly Val
            100                 105                 110

Leu Ser Arg Thr Ser Leu Arg Ser Gly Asn Phe Ile Lys Asp Met Pro
        115                 120                 125

Asp Val Thr His Val Gln Ile Gly Ala Thr Lys Arg Ala Asn Asn Thr
130                 135                 140

Val Trp Gly Ser Asn Leu Gln Ile Arg Asn Leu Thr Val Tyr Asn Arg
145                 150                 155                 160

Ala Leu Thr Pro Glu Glu Val Gln Lys Arg Ser Gln Leu Phe Lys Arg
                165                 170                 175

Ser Asp Leu Glu Lys Lys Leu Pro Glu Gly Ala Ala Leu Thr Glu Lys
            180                 185                 190

Thr Asp Ile Phe Glu Ser Gly Arg Asn Gly Asn Pro Asn Lys Asp Gly
        195                 200                 205

Ser Gly Cys
    210
```

<210> SEQ ID NO 23
<211> LENGTH: 186
<212> TYPE: PRT
<213> ORGANISM: Artificial Sequence
<220> FEATURE:
<223> OTHER INFORMATION: Synthetic construct

<400> SEQUENCE: 23

```
Glu Phe Lys Pro Asp Ala Lys Ala Pro Ala Phe Tyr Asn Leu Phe Ser
1               5                   10                  15

Val Ser Ser Ala Thr Lys Lys Asp Glu Tyr Phe Thr Met Ala Val Tyr
            20                  25                  30

Asn Asn Thr Ala Thr Leu Glu Gly Arg Gly Ser Asp Gly Lys Gln Phe
        35                  40                  45

Tyr Asn Asn Tyr Asn Asp Ala Pro Leu Lys Val Lys Pro Gly Gln Trp
50                  55                  60

Asn Ser Val Thr Phe Thr Val Glu Lys Pro Thr Ala Glu Leu Pro Lys
65                  70                  75                  80

Gly Arg Val Arg Leu Tyr Val Asn Gly Val Leu Ser Arg Thr Ser Leu
                85                  90                  95

Arg Ser Gly Asn Phe Ile Lys Asp Met Pro Asp Val Thr His Val Gln
            100                 105                 110
```

```
Ile Gly Ala Thr Lys Arg Ala Asn Asn Thr Val Trp Gly Ser Asn Leu
        115                 120                 125

Gln Ile Arg Asn Leu Thr Val Tyr Asn Arg Ala Leu Thr Pro Glu Glu
        130                 135                 140

Val Gln Lys Arg Ser Gln Leu Phe Lys Arg Ser Asp Leu Glu Lys Lys
145                 150                 155                 160

Leu Pro Glu Gly Ala Ala Leu Thr Glu Lys Thr Asp Ile Phe Glu Ser
                165                 170                 175

Gly Arg Asn Gly Asn Pro Asn Lys Asp Gly
                180                 185

<210> SEQ ID NO 24
<211> LENGTH: 37
<212> TYPE: DNA
<213> ORGANISM: Artificial Sequence
<220> FEATURE:
<223> OTHER INFORMATION: Primer

<400> SEQUENCE: 24
ggaattccat atgccgacag cagaactacc taaaggc                              37

<210> SEQ ID NO 25
<211> LENGTH: 33
<212> TYPE: DNA
<213> ORGANISM: Artificial Sequence
<220> FEATURE:
<223> OTHER INFORMATION: Primer

<400> SEQUENCE: 25
cgcggatcct catactgggt taggaaagtc gct                                  33

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ggaattccat atgcgtattc ca                                              22

<210> SEQ ID NO 27
<211> LENGTH: 29
<212> TYPE: DNA
<213> ORGANISM: Artificial Sequence
<220> FEATURE:
<223> OTHER INFORMATION: Primer

<400> SEQUENCE: 27
cgcggatcca tcggctttga ccatcggag                                       29

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
ggaattccat atggagttta agccagatg                                       29
```

<210> SEQ ID NO 29
<211> LENGTH: 32
<212> TYPE: DNA
<213> ORGANISM: Artificial Sequence
<220> FEATURE:
<223> OTHER INFORMATION: Primer

<400> SEQUENCE: 29
cgcagtggat ccatctttat ttgggttacc gt                                32

<210> SEQ ID NO 30
<211> LENGTH: 800
<212> TYPE: PRT
<213> ORGANISM: Artificial Sequence
<220> FEATURE:
<223> OTHER INFORMATION: Synthetic construct

<400> SEQUENCE: 30

Met Ser Tyr Phe Arg Asn Arg Asp Ile Asp Ile Glu Arg Asn Ser Met
1               5                   10                  15

Ile Arg Ser Val Gln Glu Arg Lys Cys Arg Tyr Ser Ile Arg Lys Leu
            20                  25                  30

Ser Val Gly Ala Val Ser Met Ile Val Gly Ala Val Val Phe Gly Thr
        35                  40                  45

Ser Pro Val Leu Ala Gln Gly Ala Ser Glu Gln Pro Leu Ala Asn
    50                  55                  60

Glu Thr Gln Leu Ser Gly Glu Ser Ser Thr Leu Thr Asp Thr Glu Lys
65                  70                  75                  80

Ser Gln Pro Ser Ser Glu Thr Glu Leu Ser Gly Asn Lys Gln Glu Gln
                85                  90                  95

Glu Arg Lys Asp Lys Gln Glu Lys Ile Pro Arg Asp Tyr Tyr Ala
            100                 105                 110

Arg Asp Leu Glu Asn Val Glu Thr Val Ile Glu Lys Glu Asp Val Glu
        115                 120                 125

Thr Asn Ala Ser Asn Gly Gln Arg Val Asp Leu Ser Ser Glu Leu Asp
    130                 135                 140

Lys Leu Lys Lys Leu Glu Asn Ala Thr Val His Met Glu Phe Lys Pro
145                 150                 155                 160

Asp Ala Lys Ala Pro Ala Phe Tyr Asn Leu Phe Ser Val Ser Ser Ala
                165                 170                 175

Thr Lys Lys Asp Glu Tyr Phe Thr Met Ala Val Tyr Asn Asn Thr Ala
            180                 185                 190

Thr Leu Glu Gly Arg Gly Ser Asp Gly Lys Gln Phe Tyr Asn Asn Tyr
        195                 200                 205

Asn Asp Ala Pro Leu Lys Val Lys Pro Gly Gln Trp Asn Ser Val Thr
    210                 215                 220

Phe Thr Val Glu Lys Pro Thr Ala Glu Leu Pro Lys Gly Arg Val Arg
225                 230                 235                 240

Leu Tyr Val Asn Gly Val Leu Ser Arg Thr Ser Leu Arg Ser Gly Asn
                245                 250                 255

Phe Ile Lys Asp Met Pro Asp Val Thr His Val Gln Ile Gly Ala Thr
            260                 265                 270

Lys Arg Ala Asn Asn Thr Val Trp Gly Ser Asn Leu Gln Ile Arg Asn
        275                 280                 285

Leu Thr Val Tyr Asn Arg Ala Leu Thr Pro Glu Glu Val Gln Lys Arg
    290                 295                 300

```
Ser Gln Leu Phe Lys Arg Ser Asp Leu Glu Lys Leu Pro Glu Gly
305                 310                 315                 320

Ala Ala Leu Thr Glu Lys Thr Asp Ile Phe Glu Ser Gly Arg Asn Gly
                325                 330                 335

Asn Pro Asn Lys Asp Gly Ile Lys Ser Tyr Arg Ile Pro Ala Leu Leu
            340                 345                 350

Lys Thr Asp Lys Gly Thr Leu Ile Ala Gly Ala Asp Glu Arg Arg Leu
        355                 360                 365

His Ser Ser Asp Trp Gly Asp Ile Gly Met Val Ile Arg Arg Ser Glu
    370                 375                 380

Asp Asn Gly Lys Thr Trp Gly Asp Arg Val Thr Ile Thr Asn Leu Arg
385                 390                 395                 400

Asp Asn Pro Lys Ala Ser Asp Pro Ser Ile Gly Ser Pro Val Asn Ile
                405                 410                 415

Asp Met Val Leu Val Gln Asp Pro Glu Thr Lys Arg Ile Phe Ser Ile
            420                 425                 430

Tyr Asp Met Phe Pro Glu Gly Lys Gly Ile Phe Gly Met Ser Ser Gln
        435                 440                 445

Lys Glu Glu Ala Tyr Lys Lys Ile Asp Gly Lys Thr Tyr Gln Ile Leu
    450                 455                 460

Tyr Arg Glu Gly Glu Lys Gly Ala Tyr Thr Ile Arg Glu Asn Gly Thr
465                 470                 475                 480

Val Tyr Thr Pro Asp Gly Lys Ala Thr Asp Tyr Arg Val Val Val Asp
                485                 490                 495

Pro Val Lys Pro Ala Tyr Ser Asp Lys Gly Asp Leu Tyr Lys Gly Asp
            500                 505                 510

Gln Leu Leu Gly Asn Ile Tyr Phe Thr Thr Asn Lys Thr Ser Pro Phe
        515                 520                 525

Arg Ile Ala Lys Asp Ser Tyr Leu Trp Met Ser Tyr Ser Asp Asp Asp
    530                 535                 540

Gly Lys Thr Trp Ser Ala Pro Gln Asp Ile Thr Pro Met Val Lys Ala
545                 550                 555                 560

Asp Trp Met Lys Phe Leu Gly Val Gly Pro Gly Thr Gly Ile Val Leu
                565                 570                 575

Arg Asn Gly Pro His Lys Gly Arg Ile Leu Ile Pro Val Tyr Thr Thr
            580                 585                 590

Asn Asn Val Ser His Leu Asp Gly Ser Gln Ser Ser Arg Val Ile Tyr
        595                 600                 605

Ser Asp Asp His Gly Lys Thr Trp His Ala Gly Glu Ala Val Asn Asp
    610                 615                 620

Asn Arg Gln Val Asp Gly Gln Lys Ile His Ser Ser Thr Met Asn Asn
625                 630                 635                 640

Arg Arg Ala Gln Asn Thr Glu Ser Thr Val Val Gln Leu Asn Asn Gly
                645                 650                 655

Asp Val Lys Leu Phe Met Arg Gly Leu Thr Gly Asp Leu Gln Val Ala
            660                 665                 670

Thr Ser Lys Asp Gly Gly Val Thr Trp Glu Lys Asp Ile Lys Arg Tyr
        675                 680                 685

Pro Gln Val Lys Asp Val Tyr Val Gln Met Ser Ala Ile His Thr Met
    690                 695                 700

His Glu Gly Lys Glu Tyr Ile Ile Leu Ser Asn Ala Gly Gly Pro Lys
705                 710                 715                 720
```

```
Arg Glu Asn Gly Met Val His Leu Ala Arg Val Glu Glu Asn Gly Glu
            725                 730                 735

Leu Thr Trp Leu Lys His Asn Pro Ile Gln Lys Gly Glu Phe Ala Tyr
        740                 745                 750

Asn Ser Leu Gln Glu Leu Gly Asn Gly Glu Tyr Gly Ile Leu Tyr Glu
    755                 760                 765

His Thr Glu Lys Gly Gln Asn Ala Tyr Thr Leu Ser Phe Arg Lys Phe
770                 775                 780

Asn Trp Glu Phe Leu Ser Lys Asn Leu Ile Ser Pro Thr Glu Ala Asn
785                 790                 795                 800
```

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
cgcaaaatac aacctcaacg gtggtac                                27

<210> SEQ ID NO 32
<211> LENGTH: 27
<212> TYPE: DNA
<213> ORGANISM: Artificial Sequence
<220> FEATURE:
<223> OTHER INFORMATION: Primer

<400> SEQUENCE: 32
gtaccaccgt tgaggttgta ttttgcg                                27

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
aaggagagtt tgcctttaat tcgctccaag                             30

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
cttggagcga attaaaggca aactctcctt                             30

<210> SEQ ID NO 35
<211> LENGTH: 571
<212> TYPE: PRT
<213> ORGANISM: Artificial Sequence
<220> FEATURE:
<223> OTHER INFORMATION: Synthetic construct

<400> SEQUENCE: 35

```
Pro Thr Ala Glu Leu Pro Lys Gly Arg Val Arg Leu Tyr Val Asn Gly
1               5                   10                  15

Val Leu Ser Arg Thr Ser Leu Arg Ser Gly Asn Phe Ile Lys Asp Met
            20                  25                  30
```

```
Pro Asp Val Thr His Val Gln Ile Gly Ala Thr Lys Arg Ala Asn Asn
         35                  40                  45

Thr Val Trp Gly Ser Asn Leu Gln Ile Arg Asn Leu Thr Val Tyr Asn
 50                  55                  60

Arg Ala Leu Thr Pro Glu Val Gln Lys Arg Ser Gln Leu Phe Lys
 65                  70                  75                  80

Arg Ser Asp Leu Glu Lys Lys Leu Pro Glu Ala Ala Leu Thr Glu
                 85                  90                  95

Lys Thr Asp Ile Phe Glu Ser Gly Arg Asn Gly Asn Pro Asn Lys Asp
                100                 105                 110

Gly Ile Lys Ser Tyr Arg Ile Pro Ala Leu Leu Lys Thr Asp Lys Gly
                115                 120                 125

Thr Leu Ile Ala Gly Ala Asp Glu Arg Arg Leu His Ser Ser Asp Trp
130                 135                 140

Gly Asp Ile Gly Met Val Ile Arg Ser Glu Asp Asn Gly Lys Thr
145                 150                 155                 160

Trp Gly Asp Arg Val Thr Ile Thr Asn Leu Arg Asp Asn Pro Lys Ala
                165                 170                 175

Ser Asp Pro Ser Ile Gly Ser Pro Val Asn Ile Asp Met Val Leu Val
                180                 185                 190

Gln Asp Pro Glu Thr Lys Arg Ile Phe Ser Ile Tyr Asp Met Phe Pro
                195                 200                 205

Glu Gly Lys Gly Ile Phe Gly Met Ser Ser Gln Lys Glu Glu Ala Tyr
                210                 215                 220

Lys Lys Ile Asp Gly Lys Thr Tyr Gln Ile Leu Tyr Arg Glu Gly Glu
225                 230                 235                 240

Lys Gly Ala Tyr Thr Ile Arg Glu Asn Gly Thr Val Tyr Thr Pro Asp
                245                 250                 255

Gly Lys Ala Thr Asp Tyr Arg Val Val Val Asp Pro Val Lys Pro Ala
                260                 265                 270

Tyr Ser Asp Lys Gly Asp Leu Tyr Lys Gly Asp Gln Leu Leu Gly Asn
                275                 280                 285

Ile Tyr Phe Thr Thr Asn Lys Thr Ser Pro Phe Arg Ile Ala Lys Asp
                290                 295                 300

Ser Tyr Leu Trp Met Ser Tyr Ser Asp Asp Asp Gly Lys Thr Trp Ser
305                 310                 315                 320

Ala Pro Gln Asp Ile Thr Pro Met Val Lys Ala Asp Trp Met Lys Phe
                325                 330                 335

Leu Gly Val Gly Pro Gly Thr Gly Ile Val Leu Arg Asn Gly Pro His
                340                 345                 350

Lys Gly Arg Ile Leu Ile Pro Val Tyr Thr Thr Asn Asn Val Ser His
                355                 360                 365

Leu Asp Gly Ser Gln Ser Ser Arg Val Ile Tyr Ser Asp Asp His Gly
                370                 375                 380

Lys Thr Trp His Ala Gly Glu Ala Val Asn Asp Asn Arg Gln Val Asp
385                 390                 395                 400

Gly Gln Lys Ile His Ser Ser Thr Met Asn Asn Arg Arg Ala Gln Asn
                405                 410                 415

Thr Thr Ser Thr Val Val Gln Leu Asn Asn Gly Asp Val Lys Leu Phe
                420                 425                 430

Met Arg Gly Leu Thr Gly Asp Leu Gln Val Ala Thr Ser Lys Asp Gly
                435                 440                 445
```

```
Gly Val Thr Trp Glu Lys Asp Ile Lys Arg Tyr Pro Gln Val Lys Asp
    450                 455                 460

Val Tyr Val Gln Met Ser Ala Ile His Thr Met His Glu Gly Lys Glu
465                 470                 475                 480

Tyr Ile Ile Leu Ser Asn Ala Gly Gly Pro Lys Arg Glu Asn Gly Met
                485                 490                 495

Val His Leu Ala Arg Val Glu Glu Asn Gly Glu Leu Thr Trp Leu Lys
            500                 505                 510

His Asn Pro Ile Gln Lys Gly Glu Phe Ala Tyr Asn Ser Leu Gln Glu
        515                 520                 525

Leu Gly Asn Gly Glu Tyr Gly Ile Leu Tyr His Thr Glu Lys Gly
    530                 535                 540

Gln Asn Ala Tyr Thr Leu Ser Phe Arg Lys Phe Asn Trp Glu Phe Leu
545                 550                 555                 560

Ser Lys Asn Leu Ile Ser Pro Thr Glu Ala Asn
                565                 570

<210> SEQ ID NO 36
<211> LENGTH: 571
<212> TYPE: PRT
<213> ORGANISM: Artificial Sequence
<220> FEATURE:
<223> OTHER INFORMATION: Synthetic construct

<400> SEQUENCE: 36

Pro Thr Ala Glu Leu Pro Lys Gly Arg Val Arg Leu Tyr Val Asn Gly
1               5                   10                  15

Val Leu Ser Arg Thr Ser Leu Arg Ser Gly Asn Phe Ile Lys Asp Met
            20                  25                  30

Pro Asp Val Thr His Val Gln Ile Gly Ala Thr Lys Arg Ala Asn Asn
        35                  40                  45

Thr Val Trp Gly Ser Asn Leu Gln Ile Arg Asn Leu Thr Val Tyr Asn
    50                  55                  60

Arg Ala Leu Thr Pro Glu Glu Val Gln Lys Arg Ser Gln Leu Phe Lys
65                  70                  75                  80

Arg Ser Asp Leu Glu Lys Lys Leu Pro Glu Gly Ala Ala Leu Thr Glu
                85                  90                  95

Lys Thr Asp Ile Phe Glu Ser Gly Arg Asn Gly Asn Pro Asn Lys Asp
            100                 105                 110

Gly Ile Lys Ser Tyr Arg Ile Pro Ala Leu Leu Lys Thr Asp Lys Gly
        115                 120                 125

Thr Leu Ile Ala Gly Ala Asp Glu Arg Arg Leu His Ser Ser Asp Trp
    130                 135                 140

Gly Asp Ile Gly Met Val Ile Arg Arg Ser Glu Asp Asn Gly Lys Thr
145                 150                 155                 160

Trp Gly Asp Arg Val Thr Ile Thr Asn Leu Arg Asp Asn Pro Lys Ala
                165                 170                 175

Ser Asp Pro Ser Ile Gly Ser Pro Val Asn Ile Asp Met Val Leu Val
            180                 185                 190

Gln Asp Pro Glu Thr Lys Arg Ile Phe Ser Ile Tyr Asp Met Phe Pro
        195                 200                 205

Glu Gly Lys Gly Ile Phe Gly Met Ser Ser Gln Lys Glu Glu Ala Tyr
    210                 215                 220

Lys Lys Ile Asp Gly Lys Thr Tyr Gln Ile Leu Tyr Arg Glu Gly Glu
225                 230                 235                 240
```

```
Lys Gly Ala Tyr Thr Ile Arg Glu Asn Gly Thr Val Tyr Thr Pro Asp
            245                 250                 255

Gly Lys Ala Thr Asp Tyr Arg Val Val Asp Pro Val Lys Pro Ala
            260                 265                 270

Tyr Ser Asp Lys Gly Asp Leu Tyr Lys Gly Asp Gln Leu Leu Gly Asn
            275                 280                 285

Ile Tyr Phe Thr Thr Asn Lys Thr Ser Pro Phe Arg Ile Ala Lys Asp
            290                 295                 300

Ser Tyr Leu Trp Met Ser Tyr Ser Asp Asp Asp Gly Lys Thr Trp Ser
305                 310                 315                 320

Ala Pro Gln Asp Ile Thr Pro Met Val Lys Ala Asp Trp Met Lys Phe
            325                 330                 335

Leu Gly Val Gly Pro Gly Thr Gly Ile Val Leu Arg Asn Gly Pro His
            340                 345                 350

Lys Gly Arg Ile Leu Ile Pro Val Tyr Thr Thr Asn Asn Val Ser His
            355                 360                 365

Leu Asp Gly Ser Gln Ser Ser Arg Val Ile Tyr Ser Asp His Gly
            370                 375                 380

Lys Thr Trp His Ala Gly Glu Ala Val Asn Asp Asn Arg Gln Val Asp
385                 390                 395                 400

Gly Gln Lys Ile His Ser Ser Thr Met Asn Asn Arg Arg Ala Gln Asn
            405                 410                 415

Thr Glu Ser Thr Val Val Gln Leu Asn Asn Gly Asp Val Lys Leu Phe
            420                 425                 430

Met Arg Gly Leu Thr Gly Asp Leu Gln Val Ala Thr Ser Lys Asp Gly
            435                 440                 445

Gly Val Thr Trp Glu Lys Asp Ile Lys Arg Tyr Pro Gln Val Lys Asp
            450                 455                 460

Val Tyr Val Gln Met Ser Ala Ile His Thr Met His Glu Gly Lys Glu
465                 470                 475                 480

Tyr Ile Ile Leu Ser Asn Ala Gly Gly Pro Lys Arg Glu Asn Gly Met
            485                 490                 495

Val His Leu Ala Arg Val Glu Glu Asn Gly Glu Leu Thr Trp Leu Lys
            500                 505                 510

His Asn Pro Ile Gln Lys Gly Glu Phe Ala Phe Asn Ser Leu Gln Glu
            515                 520                 525

Leu Gly Asn Gly Glu Tyr Gly Ile Leu Tyr Glu His Thr Glu Lys Gly
            530                 535                 540

Gln Asn Ala Tyr Thr Leu Ser Phe Arg Lys Phe Asn Trp Glu Phe Leu
545                 550                 555                 560

Ser Lys Asn Leu Ile Ser Pro Thr Glu Ala Asn
            565                 570

<210> SEQ ID NO 37
<211> LENGTH: 483
<212> TYPE: PRT
<213> ORGANISM: Macrobdella decora

<400> SEQUENCE: 37

Gly Glu Asn Ile Phe Tyr Ala Gly Asp Val Thr Glu Ser Asn Tyr Phe
1               5                   10                  15

Arg Ile Pro Ser Leu Leu Thr Leu Ser Thr Gly Thr Val Ile Ser Ala
            20                  25                  30

Ala Asp Ala Arg Tyr Gly Gly Thr His Asp Ser Lys Ser Lys Ile Asn
            35                  40                  45
```

-continued

```
Ile Ala Phe Ala Lys Ser Thr Asp Gly Gly Asn Thr Trp Ser Glu Pro
 50                  55                  60

Thr Leu Pro Leu Lys Phe Asp Asp Tyr Ile Ala Lys Asn Ile Asp Trp
 65                  70                  75                  80

Pro Arg Asp Ser Val Gly Lys Asn Val Gln Ile Gln Gly Ser Ala Ser
                 85                  90                  95

Tyr Ile Asp Pro Val Leu Leu Glu Asp Lys Leu Thr Lys Arg Ile Phe
                100                 105                 110

Leu Phe Ala Asp Leu Met Pro Ala Gly Ile Gly Ser Ser Asn Ala Ser
                115                 120                 125

Val Gly Ser Gly Phe Lys Glu Val Asn Gly Lys Lys Tyr Leu Lys Leu
130                 135                 140

Arg Trp His Lys Asp Ala Gly Arg Ala Tyr Asp Tyr Thr Ile Arg Glu
145                 150                 155                 160

Lys Gly Val Ile Tyr Asn Asp Ala Thr Asn Gln Pro Thr Glu Phe Arg
                165                 170                 175

Val Asp Gly Glu Tyr Asn Leu Tyr Gln His Asp Thr Asn Leu Thr Cys
                180                 185                 190

Lys Gln Tyr Asp Tyr Asn Phe Ser Gly Asn Asn Leu Ile Glu Ser Lys
                195                 200                 205

Thr Asp Val Asp Val Asn Met Asn Ile Phe Tyr Lys Asn Ser Val Phe
                210                 215                 220

Lys Ala Phe Pro Thr Asn Tyr Leu Ala Met Arg Tyr Ser Asp Asp Glu
225                 230                 235                 240

Gly Ala Ser Trp Ser Asp Leu Asp Ile Val Ser Ser Phe Lys Pro Glu
                245                 250                 255

Val Ser Lys Phe Leu Val Val Gly Pro Gly Ile Gly Lys Gln Ile Ser
                260                 265                 270

Thr Gly Glu Asn Ala Gly Arg Leu Leu Val Pro Leu Tyr Ser Lys Ser
                275                 280                 285

Ser Ala Glu Leu Gly Phe Met Tyr Ser Asp Asp His Gly Asp Asn Trp
                290                 295                 300

Thr Tyr Val Glu Ala Asp Asn Leu Thr Gly Gly Ala Thr Ala Glu Ala
305                 310                 315                 320

Gln Ile Val Glu Met Pro Asp Gly Ser Leu Lys Thr Tyr Leu Arg Thr
                325                 330                 335

Gly Ser Asn Cys Ile Ala Glu Val Thr Ser Ile Asp Gly Gly Glu Thr
                340                 345                 350

Trp Ser Asp Arg Val Pro Leu Gln Gly Ile Ser Thr Thr Ser Tyr Gly
                355                 360                 365

Thr Gln Leu Ser Val Ile Asn Tyr Ser Gln Pro Ile Asp Gly Lys Pro
                370                 375                 380

Ala Ile Ile Leu Ser Ser Pro Asn Ala Thr Asn Gly Arg Lys Asn Gly
385                 390                 395                 400

Lys Ile Trp Ile Gly Leu Val Asn Asp Thr Gly Asn Thr Gly Ile Asp
                405                 410                 415

Lys Tyr Ser Val Glu Trp Lys Tyr Ser Tyr Ala Val Asp Thr Pro Gln
                420                 425                 430

Met Gly Tyr Ser Tyr Ser Cys Leu Ala Glu Leu Pro Asp Gly Gln Val
                435                 440                 445

Gly Leu Leu Tyr Glu Lys Tyr Asp Ser Trp Ser Arg Asn Glu Leu His
450                 455                 460
```

```
Leu Lys Asp Ile Leu Lys Phe Glu Lys Tyr Ser Ile Ser Glu Leu Thr
465                 470                 475                 480

Gly Gln Ala
```

<210> SEQ ID NO 38
<211> LENGTH: 361
<212> TYPE: PRT
<213> ORGANISM: Micromonospora viridifaciens

<400> SEQUENCE: 38

```
Gly Glu Pro Leu Tyr Thr Glu Gln Asp Leu Ala Val Asn Gly Arg Glu
1               5                   10                  15

Gly Phe Pro Asn Tyr Arg Ile Pro Ala Leu Thr Val Thr Pro Asp Gly
            20                  25                  30

Asp Leu Leu Ala Ser Tyr Asp Gly Arg Pro Thr Gly Ile Asp Ala Pro
        35                  40                  45

Gly Pro Asn Ser Ile Leu Gln Arg Arg Ser Thr Asp Gly Gly Arg Thr
    50                  55                  60

Trp Gly Glu Gln Gln Val Val Ser Ala Gly Thr Thr Ala Pro Ile
65                  70                  75                  80

Lys Gly Phe Ser Asp Pro Ser Tyr Leu Val Asp Arg Glu Thr Gly Thr
                85                  90                  95

Ile Phe Asn Phe His Val Tyr Ser Gln Arg Gln Gly Phe Ala Gly Ser
                100                 105                 110

Arg Pro Gly Thr Asp Pro Ala Asp Pro Asn Val Leu His Ala Asn Val
            115                 120                 125

Ala Thr Ser Thr Asp Gly Gly Leu Thr Trp Ser His Arg Thr Ile Thr
130                 135                 140

Ala Asp Ile Thr Pro Asp Pro Gly Trp Arg Ser Arg Phe Ala Ala Ser
145                 150                 155                 160

Gly Glu Gly Ile Gln Leu Arg Tyr Gly Pro His Ala Gly Arg Leu Ile
                165                 170                 175

Gln Gln Tyr Thr Ile Ile Asn Ala Ala Gly Ala Phe Gln Ala Val Ser
            180                 185                 190

Val Tyr Ser Asp Asp His Gly Arg Thr Trp Arg Ala Gly Glu Ala Val
        195                 200                 205

Gly Val Gly Met Asp Glu Asn Lys Thr Val Glu Leu Ser Asp Gly Arg
    210                 215                 220

Val Leu Leu Asn Ser Arg Asp Ser Ala Arg Ser Gly Tyr Arg Lys Val
225                 230                 235                 240

Ala Val Ser Thr Asp Gly Gly His Ser Tyr Gly Pro Val Thr Ile Asp
                245                 250                 255

Arg Asp Leu Pro Asp Pro Thr Asn Asn Ala Ser Ile Ile Arg Ala Phe
            260                 265                 270

Pro Asp Ala Pro Ala Gly Ser Ala Arg Ala Lys Val Leu Leu Phe Ser
        275                 280                 285

Asn Ala Ala Ser Gln Thr Ser Arg Ser Gln Gly Thr Ile Arg Met Ser
    290                 295                 300

Cys Asp Asp Gly Gln Thr Trp Pro Val Ser Lys Val Phe Gln Pro Gly
305                 310                 315                 320

Ser Met Ser Tyr Ser Thr Leu Thr Ala Leu Pro Asp Gly Thr Tyr Gly
                325                 330                 335
```

Leu Leu Tyr Glu Pro Gly Thr Gly Ile Arg Tyr Ala Asn Phe Asn Leu
                340                 345                 350

Ala Trp Leu Gly Gly Ile Cys Ala Pro
        355                 360

<210> SEQ ID NO 39
<211> LENGTH: 379
<212> TYPE: PRT
<213> ORGANISM: Salmonella typhimurium

<400> SEQUENCE: 39

Glu Lys Ser Val Val Phe Lys Ala Glu Gly Glu His Phe Thr Asp Gln
  1               5                  10                  15

Lys Gly Asn Thr Ile Val Gly Ser Gly Ser Gly Thr Thr Lys Tyr
             20                  25                  30

Phe Arg Ile Pro Ala Met Cys Thr Thr Ser Lys Gly Thr Ile Val Val
             35                  40                  45

Phe Ala Asp Ala Arg His Asn Thr Ala Ser Asp Gln Ser Phe Ile Asp
 50                  55                  60

Thr Ala Ala Arg Ser Thr Asp Gly Gly Lys Thr Trp Asn Lys Lys
 65                  70                  75                  80

Ile Ala Ile Tyr Asn Asp Arg Val Asn Ser Lys Leu Ser Arg Val Met
                 85                  90                  95

Asp Pro Thr Cys Ile Val Ala Asn Ile Gln Gly Arg Glu Thr Ile Leu
            100                 105                 110

Val Met Val Gly Lys Trp Asn Asn Asn Asp Lys Thr Trp Gly Ala Tyr
            115                 120                 125

Arg Asp Lys Ala Pro Asp Thr Asp Trp Asp Leu Val Leu Tyr Lys Ser
            130                 135                 140

Thr Asp Asp Gly Val Thr Phe Ser Lys Val Glu Thr Asn Ile His Asp
145                 150                 155                 160

Ile Val Thr Lys Asn Gly Thr Ile Ser Ala Met Leu Gly Gly Val Gly
                165                 170                 175

Ser Gly Leu Gln Leu Asn Asp Gly Lys Leu Val Phe Pro Val Gln Met
            180                 185                 190

Val Arg Thr Lys Asn Ile Thr Thr Val Leu Asn Thr Ser Phe Ile Tyr
            195                 200                 205

Ser Thr Asp Gly Ile Thr Trp Ser Leu Pro Ser Gly Tyr Cys Glu Gly
            210                 215                 220

Phe Gly Ser Glu Asn Asn Ile Ile Glu Phe Asn Ala Ser Leu Val Asn
225                 230                 235                 240

Asn Ile Arg Asn Ser Gly Leu Arg Arg Ser Phe Glu Thr Lys Asp Phe
                245                 250                 255

Gly Lys Thr Trp Thr Glu Phe Pro Pro Met Asp Lys Lys Val Asp Asn
            260                 265                 270

Arg Asn His Gly Val Gln Gly Ser Thr Ile Thr Ile Pro Ser Gly Asn
            275                 280                 285

Lys Leu Val Ala Ala His Ser Ser Ala Gln Asn Lys Asn Asn Asp Tyr
            290                 295                 300

Thr Arg Ser Asp Ile Ser Leu Tyr Ala His Asn Leu Tyr Ser Gly Glu
305                 310                 315                 320

Val Lys Leu Ile Asp Asp Phe Tyr Pro Lys Val Gly Asn Ala Ser Gly
                325                 330                 335

Ala Gly Tyr Ser Cys Leu Ser Tyr Arg Lys Asn Val Asp Lys Glu Thr
            340                 345                 350

Leu Tyr Val Val Tyr Glu Ala Asn Gly Ser Ile Glu Phe Gln Asp Leu
            355                 360                 365

Ser Arg His Leu Pro Val Ile Lys Ser Tyr Asn
    370                 375

<210> SEQ ID NO 40
<211> LENGTH: 565
<212> TYPE: PRT
<213> ORGANISM: Vibrio cholerae

<400> SEQUENCE: 40

Val Ile Phe Arg Gly Pro Asp Arg Ile Pro Ser Ile Val Ala Ser Ser
1               5                   10                  15

Val Thr Pro Gly Val Val Thr Ala Phe Ala Glu Lys Arg Val Gly Gly
            20                  25                  30

Gly Asp Pro Gly Ala Leu Ser Asn Thr Asn Asp Ile Ile Thr Arg Thr
        35                  40                  45

Ser Arg Asp Gly Gly Ile Thr Trp Asp Thr Glu Leu Asn Leu Thr Glu
    50                  55                  60

Gln Ile Asn Val Ser Asp Glu Phe Asp Phe Ser Asp Pro Arg Pro Ile
65                  70                  75                  80

Tyr Asp Pro Ser Ser Asn Thr Val Leu Val Ser Tyr Ala Arg Trp Pro
                85                  90                  95

Thr Asp Ala Ala Gln Asn Gly Asp Arg Ile Lys Pro Trp Met Pro Asn
            100                 105                 110

Gly Ile Phe Tyr Ser Val Tyr Asp Val Ala Ser Gly Asn Trp Gln Ala
        115                 120                 125

Pro Ile Asp Val Thr Asp Gln Val Lys Glu Arg Ser Phe Gln Ile Ala
    130                 135                 140

Gly Trp Gly Gly Ser Glu Leu Tyr Arg Arg Asn Thr Ser Leu Asn Ser
145                 150                 155                 160

Gln Gln Asp Trp Gln Ser Asn Ala Lys Ile Arg Ile Val Asp Gly Ala
                165                 170                 175

Ala Asn Gln Ile Gln Val Ala Asp Gly Ser Arg Lys Tyr Val Val Thr
            180                 185                 190

Leu Ser Ile Asp Glu Ser Gly Gly Leu Val Ala Asn Leu Asn Gly Val
        195                 200                 205

Ser Ala Pro Ile Ile Leu Gln Ser Glu His Ala Lys Val His Ser Phe
    210                 215                 220

His Asp Tyr Glu Leu Gln Tyr Ser Ala Leu Asn His Thr Thr Thr Leu
225                 230                 235                 240

Phe Val Asp Gly Gln Gln Ile Thr Thr Trp Ala Gly Glu Val Ser Gln
                245                 250                 255

Glu Asn Asn Ile Gln Phe Gly Asn Ala Asp Ala Gln Ile Asp Gly Arg
            260                 265                 270

Leu His Val Gln Lys Ile Val Leu Thr Gln Gln Gly His Asn Leu Val
        275                 280                 285

Glu Phe Asp Ala Phe Tyr Leu Ala Gln Gln Thr Pro Glu Val Glu Lys
    290                 295                 300

Asp Leu Glu Lys Leu Gly Trp Thr Lys Ile Lys Thr Gly Asn Thr Met
305                 310                 315                 320

Ser Leu Tyr Gly Asn Ala Ser Val Asn Pro Gly Pro His Gly Ile
                325                 330                 335

Thr Leu Thr Arg Gln Gln Asn Ile Ser Gly Ser Gln Asn Gly Arg Leu
            340                 345                 350

```
Ile Tyr Pro Ala Ile Val Leu Asp Arg Phe Phe Leu Asn Val Met Ser
        355                 360                 365

Ile Tyr Ser Asp Asp Gly Gly Ser Asn Trp Gln Thr Gly Ser Thr Leu
    370                 375                 380

Pro Ile Pro Phe Arg Trp Lys Ser Ser Ile Leu Glu Thr Leu Glu
385                 390                 395                 400

Pro Ser Glu Ala Asp Met Val Glu Leu Gln Asn Gly Asp Leu Leu Leu
                    405                 410                 415

Thr Ala Arg Leu Asp Phe Asn Gln Ile Val Asn Gly Val Asn Tyr Ser
                420                 425                 430

Pro Arg Gln Gln Phe Leu Ser Lys Asp Gly Gly Ile Thr Trp Ser Leu
            435                 440                 445

Leu Glu Ala Asn Asn Ala Asn Val Phe Ser Asn Ile Ser Thr Gly Thr
    450                 455                 460

Val Asp Ala Ser Ile Thr Arg Phe Glu Gln Ser Asp Gly Ser His Phe
465                 470                 475                 480

Leu Leu Phe Thr Asn Pro Gln Gly Asn Pro Ala Gly Thr Asn Gly Arg
                    485                 490                 495

Gln Asn Leu Gly Leu Trp Phe Ser Phe Asp Glu Gly Val Thr Trp Lys
                500                 505                 510

Gly Pro Ile Gln Leu Val Asn Gly Ala Ser Ala Tyr Ser Asp Ile Tyr
            515                 520                 525

Gln Leu Asp Ser Glu Asn Ala Ile Val Ile Val Glu Thr Asp Asn Ser
    530                 535                 540

Asn Met Arg Ile Leu Arg Met Pro Ile Thr Leu Leu Lys Gln Lys Leu
545                 550                 555                 560

Thr Leu Ser Gln Asn
                565

<210> SEQ ID NO 41
<211> LENGTH: 570
<212> TYPE: PRT
<213> ORGANISM: Streptococcus pneumoniae

<400> SEQUENCE: 41

Thr Ala Glu Leu Pro Lys Gly Arg Val Arg Leu Tyr Val Asn Gly Val
1               5                   10                  15

Leu Ser Arg Thr Ser Leu Arg Ser Gly Asn Phe Ile Lys Asp Met Pro
                20                  25                  30

Asp Val Thr His Val Gln Ile Gly Ala Thr Lys Arg Ala Asn Asn Thr
            35                  40                  45

Val Trp Gly Ser Asn Leu Gln Ile Arg Asn Leu Thr Val Tyr Asn Arg
    50                  55                  60

Ala Leu Thr Pro Glu Glu Val Gln Lys Arg Ser Gln Leu Phe Lys Arg
65                  70                  75                  80

Ser Asp Leu Glu Lys Lys Leu Pro Glu Gly Ala Ala Leu Thr Glu Lys
                85                  90                  95

Thr Asp Ile Phe Glu Ser Gly Arg Asn Gly Asn Pro Asn Lys Asp Gly
                100                 105                 110

Ile Lys Ser Tyr Arg Ile Pro Ala Leu Leu Lys Thr Asp Lys Gly Thr
            115                 120                 125

Leu Ile Ala Gly Ala Asp Glu Arg Arg Leu His Ser Ser Asp Trp Gly
    130                 135                 140

Asp Ile Gly Met Val Ile Arg Arg Ser Glu Asp Asn Gly Lys Thr Trp
145                 150                 155                 160
```

```
Gly Asp Arg Val Thr Ile Thr Asn Leu Arg Asp Asn Pro Lys Ala Ser
            165                 170                 175

Asp Pro Ser Ile Gly Ser Pro Val Asn Ile Asp Met Val Leu Val Gln
            180                 185                 190

Asp Pro Glu Thr Lys Arg Ile Phe Ser Ile Tyr Asp Met Phe Pro Glu
            195                 200                 205

Gly Lys Gly Ile Phe Gly Met Ser Ser Gln Lys Glu Glu Ala Tyr Lys
            210                 215                 220

Lys Ile Asp Gly Lys Thr Tyr Gln Ile Leu Tyr Arg Glu Gly Glu Lys
225                 230                 235                 240

Gly Ala Tyr Thr Ile Arg Glu Asn Gly Thr Val Tyr Thr Pro Asp Gly
            245                 250                 255

Lys Ala Thr Asp Tyr Arg Val Val Asp Pro Val Lys Pro Ala Tyr
            260                 265                 270

Ser Asp Lys Gly Asp Leu Tyr Lys Gly Asp Gln Leu Leu Gly Asn Ile
            275                 280                 285

Tyr Phe Thr Thr Asn Lys Thr Ser Pro Phe Arg Ile Ala Lys Asp Ser
            290                 295                 300

Tyr Leu Trp Met Ser Tyr Ser Asp Asp Gly Lys Thr Trp Ser Ala
305                 310                 315                 320

Pro Gln Asp Ile Thr Pro Met Val Lys Ala Asp Trp Met Lys Phe Leu
            325                 330                 335

Gly Val Gly Pro Gly Thr Gly Ile Val Leu Arg Asn Gly Pro His Lys
            340                 345                 350

Gly Arg Ile Leu Ile Pro Val Tyr Thr Thr Asn Asn Val Ser His Leu
            355                 360                 365

Asp Gly Ser Gln Ser Ser Arg Val Ile Tyr Ser Asp His Gly Lys
            370                 375                 380

Thr Trp His Ala Gly Glu Ala Val Asn Asp Asn Arg Gln Val Asp Gly
385                 390                 395                 400

Gln Lys Ile His Ser Ser Thr Met Asn Asn Arg Arg Ala Gln Asn Thr
            405                 410                 415

Glu Ser Thr Val Val Gln Leu Asn Asn Gly Asp Val Lys Leu Phe Met
            420                 425                 430

Arg Gly Leu Thr Gly Asp Leu Gln Val Ala Thr Ser Lys Asp Gly Gly
            435                 440                 445

Val Thr Trp Glu Lys Asp Ile Lys Arg Tyr Pro Gln Val Lys Asp Val
            450                 455                 460

Tyr Val Gln Met Ser Ala Ile His Thr Met His Glu Gly Lys Glu Tyr
465                 470                 475                 480

Ile Ile Leu Ser Asn Ala Gly Gly Pro Lys Arg Glu Asn Gly Met Val
            485                 490                 495

His Leu Ala Arg Val Glu Glu Asn Gly Glu Leu Thr Trp Leu Lys His
            500                 505                 510

Asn Pro Ile Gln Lys Gly Glu Phe Ala Tyr Asn Ser Leu Gln Glu Leu
            515                 520                 525

Gly Asn Gly Glu Tyr Gly Ile Leu Tyr Glu His Thr Glu Lys Gly Gln
            530                 535                 540

Asn Ala Tyr Thr Leu Ser Phe Arg Lys Phe Asn Trp Glu Phe Leu Ser
545                 550                 555                 560

Lys Asn Leu Ile Ser Pro Thr Glu Ala Asn
            565                 570
```